(12) United States Patent
Arano et al.

(10) Patent No.: US 11,167,050 B2
(45) Date of Patent: Nov. 9, 2021

(54) METAL COMPLEX FORMING COMPOUND, METAL COMPLEX COMPOUND FORMED THEREOF, RADIOACTIVE DRUG CONTAINING THE METAL COMPLEX COMPOUND, AND METHOD OF USING AND PREPARING THE METAL COMPLEX COMPOUND

(71) Applicant: NATIONAL UNIVERSITY CORPORATION CHIBA UNIVERSITY, Chiba (JP)

(72) Inventors: Yasushi Arano, Chiba (JP); Tomoya Uehara, Chiba (JP); Hiroyuki Suzuki, Chiba (JP)

(73) Assignee: NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

(21) Appl. No.: 16/648,703

(22) PCT Filed: Sep. 26, 2018

(86) PCT No.: PCT/JP2018/035786
§ 371 (c)(1),
(2) Date: Mar. 19, 2020

(87) PCT Pub. No.: WO2019/065774
PCT Pub. Date: Apr. 4, 2019

(65) Prior Publication Data
US 2020/0268913 A1 Aug. 27, 2020

(30) Foreign Application Priority Data
Sep. 26, 2017 (JP) .............................. JP2017-185484

(51) Int. Cl.
*A61K 51/08* (2006.01)
*A61K 51/04* (2006.01)
*C07K 5/087* (2006.01)
*A61K 51/10* (2006.01)

(52) U.S. Cl.
CPC ........ *A61K 51/088* (2013.01); *A61K 51/0482* (2013.01); *C07K 5/0812* (2013.01); *A61K 51/10* (2013.01)

(58) Field of Classification Search
CPC ...... A61K 51/00; A61K 51/08; A61K 51/088; A61K 51/04; A61K 51/0482; A61K 51/10; A61P 35/00; C07K 5/0812; C07K 5/00; C07K 7/00; G01T 1/161
USPC .......... 424/1.11, 1.65, 1.69, 1.81, 1.85, 1.89, 424/9.1, 9.2, 9.3, 9.4, 9.5, 9.6; 514/1, 514/1.1, 11.1, 19.2, 19.3, 19.4, 19.5, 19.6, 514/21.1, 21.7; 530/300, 311, 317, 327, 530/328; 534/7, 10–16
See application file for complete search history.

(56) References Cited

U.S. PATENT DOCUMENTS

2019/0091353 A1 3/2019 Arano et al.

FOREIGN PATENT DOCUMENTS

| JP | 2015086213 | * | 5/2015 |
| JP | 2015086213 A | | 5/2015 |
| WO | 2017150549 A1 | | 9/2017 |

OTHER PUBLICATIONS

Fleuren, et al., "Theranostic applications of antibodies in oncology", Molecular Oncology 8, 2014, pp. 799-812.
International Search Report (PCT/ISA/210) and an English translation thereof, and Written Opinion (PCT/ISA/237) dated Nov. 27, 2018, by the Japanese Patent Office as the International Searching Authority for International Application No. PCT/JP2018/035786.
Zimmermann, et al., "A Triglycine Linker Improves Tumor Uptake and Biodistributions of 67-Cu-Labeled Anti-Neuroblastoma MAb chCE7 F (ab')2 Fragments", Nuclear Medicine & Biology, 1999, vol. 26, pp. 943-950.
Extended European Search Report dated Apr. 12, 2021, issued by the European Patent Office in corresponding European Application No. 18861877.1-1109. (8 pages).
XP55791715A, Display of compounds in JP2015-86213A, May 7, 2015. (19 pages).

* cited by examiner

*Primary Examiner* — D. L. Jones
(74) *Attorney, Agent, or Firm* — Buchanan, Ingersoll & Rooney PC

(57) ABSTRACT

Described are: [1] a compound or the like represented by the formula (1); [2] a compound or the like having a target molecule recognition element bound to the compound or the like described in the above [1]; and [3] a metal complex compound or the like having a metal selected from the group consisting of a radioactive metal and a radioactive atom-labeled metal, and the compound or the like described in the above [1] or [2] coordinated to the metal. Also described are uses of the compound or the like described in the above [1] or [2] or the metal complex compound or the like described in the above [3] in a radioactive drug, a radiotherapeutic agent or a radioactive diagnostic imaging agent.

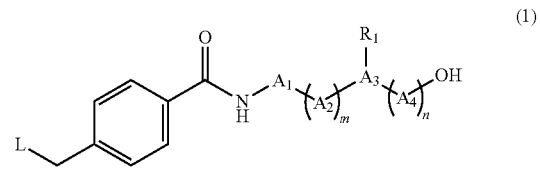

16 Claims, 8 Drawing Sheets

BLOOD (%ID/g)

KIDNEY (%ID/g)

KIDNEY – BLOOD RATIO

BLOOD (%ID/g)

KIDNEY (%ID/g)

KIDNEY - BLOOD RATIO

RESULTS OF SE-HPLC

RESULTS OF RP-HPLC

METAL COMPLEX FORMING COMPOUND, METAL COMPLEX COMPOUND FORMED THEREOF, RADIOACTIVE DRUG CONTAINING THE METAL COMPLEX COMPOUND, AND METHOD OF USING AND PREPARING THE METAL COMPLEX COMPOUND

TECHNICAL FIELD

The present invention relates to a novel compound, a radioactive drug containing the novel compound, a drug for preparing the radioactive drug, and the like.

BACKGROUND ART

A radioactive drug such as a radioactive isotope (RI) labeled antibody can allow the RI to accumulate in a tumor selective manner by virtue of high specificity and affinity of the antibody. For this reason, such a radioactive drug is used for radiation therapy such as isotope therapy, and for imaging diagnosis (Non Patent Literature 1). However, when a radioactive drug is administered to a living body, non-specific accumulation of the radioactive drug in kidney is observed in addition to specific accumulation in a target tissue. The accumulation of radioactivity in the kidney (hereinafter, also referred to as "kidney accumulation") is due to the fact that a RI-labeled low molecular weight peptide is taken into the kidney, and then transported to a lysosome, and after the RI-labeled low molecular peptide is metabolized, the thus-formed radioactive metabolite remains in the kidney.

In this regard, in Patent Literature 1, as a radiolabeled drug capable of reducing the accumulation thereof in the kidney from an early stage of administration, a compound having a polypeptide site bound to a chelating reagent such as NOTA (1,4,7,10-tetraazacyclododecane-1,4,7,10-tetraacetic acid), and a radioactive drug using the compound have been reported.

CITATION LIST

Patent Literature

Patent Literature 1: WO 2017/150549 A

Non Patent Literature

Non Patent Literature 1: Molecular Oncology 8: 799-812, 2014

SUMMARY OF INVENTION

According to the radioactive drug of Patent Literature 1, a radioactive isotope such as gallium-67 or technetium-99m can be used. However, any labeling drug that can be applied to lutetium-177 and yttrium-90 which are generally used as radioactive isotopes for therapeutic purposes, and to a variety of atoms including an atom having a relatively large atomic radius such as indium-111 which is a companion drug of the lutetium-177 and yttrium-90 has not been developed so far.

Therefore, the present invention relates to a compound and the like that can provide a radioactive drug capable of being labeled with a variety of atoms including an atom having a relatively large atomic radius and capable of reducing the accumulation thereof in the kidney.

The present invention relates the following embodiments.

1. A compound represented by the following formula (1), or a pharmacologically acceptable salt thereof:

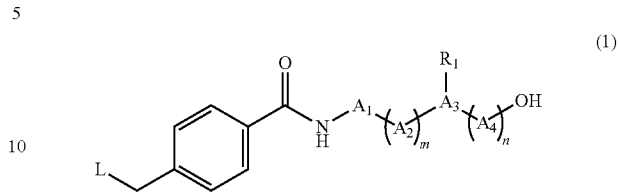

wherein $A_1$ and $A_2$ each independently represent an amino acid residue, m is an integer of 0 to 3, $A_3$ represents an amino acid residue having an amino group or a carboxy group on a side chain thereof, $A_4$ represents an amino acid residue, n is an integer of 0 to 3, $R_1$ represents a group binding to the amino group or the carboxy group on the side chain of $A_3$ and having a functional group capable of binding to a target molecule recognition element or a linking group thereof, or a hydrogen atom of the amino group or the carboxy group on the side chain of $A_3$, provided that $R_1$ may form a heterocyclic group having 3 to 10 carbon atoms including a nitrogen atom of the amino group on the side chain of $A_3$ as a ring-constituting atom, and L represents a group represented by the formula (L1):

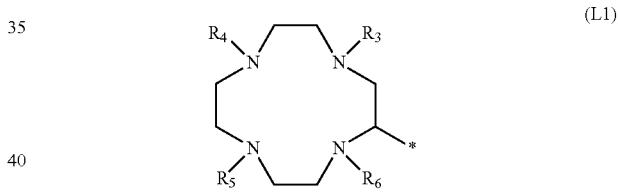

wherein $R_3$, $R_4$, $R_5$, and $R_6$ each independently represent a hydrogen atom, a —$CH_2COOR_{10}$ group, or a hydrocarbon group having 1 to 8 carbon atoms, $R_{10}$ represents a hydrogen atom or a hydrocarbon group having 1 to 8 carbon atoms, and the symbol * represents a binding site, provided that at least three of $R_3$, $R_4$, $R_5$, and $R_6$ each represent a —$CH_2COOH$ group, or a group represented by the formula (L2):

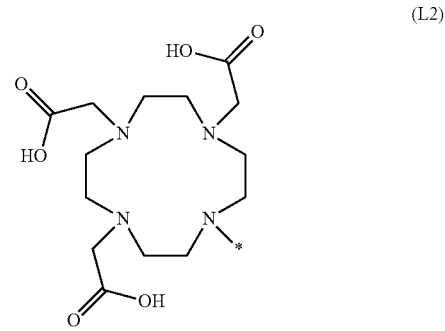

wherein the symbol * represents a binding site.

2. A compound comprising a target molecule recognition element bound to the compound or pharmacologically acceptable salt thereof described in the above item 1, or a pharmacologically acceptable salt thereof.

3. A metal complex compound comprising a metal selected from the group consisting of a radioactive metal and a radioactive atom-labeled metal, and the compound or pharmacologically acceptable salt thereof described in the above item 1 or 2 coordinated to the metal, or a pharmacologically acceptable salt thereof.

4. A drug for preparing a radioactive drug, comprising the compound or pharmacologically acceptable salt thereof described in the above item 1 or 2.

5. Use of the compound or pharmacologically acceptable salt thereof described in the above item 1 or 2, for producing a radioactive drug.

6. A radioactive drug comprising the metal complex compound or pharmacologically acceptable salt thereof described in the above item 3.

7. A radiotherapeutic agent comprising the metal complex compound or pharmacologically acceptable salt thereof described in the above item 3.

8. A radioactive diagnostic imaging agent comprising the metal complex compound or pharmacologically acceptable salt thereof described in the above item 3.

9. The compound or pharmacologically acceptable salt thereof described in the above item 1 or 2, in which the compound or pharmacologically acceptable salt thereof is for preparing a radioactive drug.

10. Use of the metal complex compound or pharmacologically acceptable salt thereof described in the above item 3, for producing a radioactive drug.

11. Use of the metal complex compound or pharmacologically acceptable salt thereof described in the above item 3, for radiation therapy.

12. Use of the metal complex compound or pharmacologically acceptable salt thereof described in the above item 3, for radiological imaging diagnosis.

13. A radiation therapy method comprising administering the metal complex compound or pharmacologically acceptable salt thereof described in the above item 3.

14. A radiological imaging diagnostic method comprising administering the metal complex compound or pharmacologically acceptable salt thereof described in the above item 3.

15. A kit comprising, as separate packaging units, the compound or pharmacologically acceptable salt thereof described in the above item 1, or a compound having a target molecule recognition element bound to the compound or pharmacologically acceptable salt thereof described in the above item 1, or a pharmacologically acceptable salt thereof; and a reagent containing a metal selected from the group consisting of a radioactive metal and a radioactive atom-labeled metal.

According to the present invention, a compound and the like that can give a radioactive drug capable of being labeled with a variety of atoms including an atom having a relatively large atomic radius and capable of reducing the accumulation thereof in the kidney can be provided.

DESCRIPTION OF EMBODIMENTS

Figure 1:
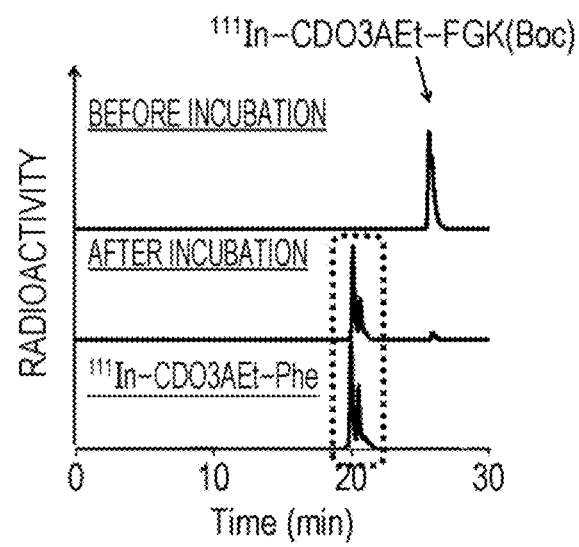
FIG. 1 shows experimental results of incubation of $^{111}$In-CDO3AEt-FGK(Boc) with BBMVs.

Compound and the Like
<Compound (1) or the Like>

The compound or pharmacologically acceptable salt thereof according to the present invention (hereinafter, also simply referred to as "compound (1) or the like") is represented by the following formula (1):

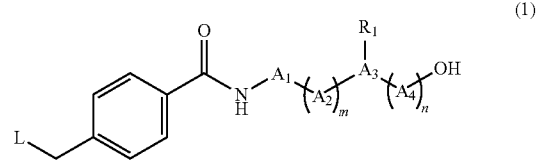

wherein
$A_1$ and $A_2$ each independently represent an amino acid residue,
m is an integer of 0 to 3,
$A_3$ represents an amino acid residue having an amino group or a carboxy group on a side chain thereof,
$A_4$ represents an amino acid residue,
n is an integer of 0 to 3,
$R_1$ represents a group binding to the amino group or the carboxy group on the side chain of $A_3$ and having a functional group capable of binding to a target molecule recognition element or a linking group thereof, or a hydrogen atom of the amino group or the carboxy group on the side chain of $A_3$, provided that $R_1$ may form a heterocyclic group having 3 to 10 carbon atoms including a nitrogen atom of the amino group on the side chain of $A_3$ as a ring-constituting atom, and L represents a group represented by the formula (L1):

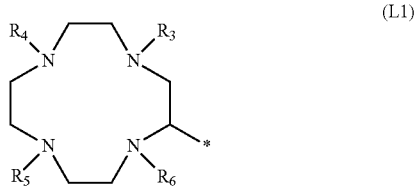

(L1)

wherein $R_3$, $R_4$, $R_5$, and $R_6$ each independently represent a hydrogen atom, a —$CH_2COOR_{10}$ group, or a hydrocarbon group having 1 to 8 carbon atoms, $R_{10}$ represents a hydrogen atom or a hydrocarbon group having 1 to 8 carbon atoms, and the symbol * represents a binding site, provided that at least three of $R_3$, $R_4$, $R_5$, and $R_6$ each represent a —$CH_2COOH$ group, or the formula (L2):

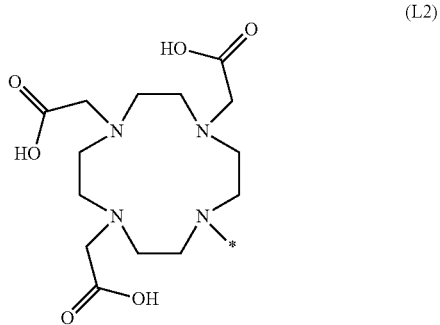 [SMILES: *N1CCN(CC(=O)O)CCN(CC(=O)O)CCN(CC(=O)O)CC1]

(L2)

wherein the symbol * represents a binding site.

According to the present invention, a compound and the like that can give a radioactive drug capable of being labeled with indium-ill and capable of reducing the accumulation thereof in the kidney can be provided. Further, since the radioactive drug according to the present invention has a target molecule recognition element, the radioactive drug can specifically bind to the target site, and therefore, efficiently accumulate in the target site. Because of having such a nature, the radioactive drug according to the present invention specifically accumulates in a tumor site in radiation therapy, and can improve radiological imaging diagnosis in sensitivity and accuracy.

The reason why the effects of the present invention can be obtained is not clear, but is considered as follows.

If an administered radioactive drug is efficiently released as radioactive metabolites that are excretable in urine when the drug is taken into kidney cells, it can be considered that the accumulation of radioactivity in the kidney can be reduced. For this reason, a substrate sequence of a renal brush border membrane enzyme is introduced between a polypeptide and a chelate ligand site so that the chelate ligand site including the radiolabeling element can be efficiently released when a radioactive drug is taken into kidney cells. By doing so, before being taken into kidney cells, the polypeptide and the chelate ligand site are released from each other, and thus it is presumed that a radioactive substance is prevented from being taken into the kidney, and the accumulation of the radioactive substance in the kidney can be reduced from an early stage of administration.

In order to enable the labeling with indium-111, introduction of a group represented by the formula (L1) or (L2) as a chelate ligand site has been examined. In this case, for example, as in the compound described in Patent Literature 1, introduction of a thiourea structure as a structure connecting a chelating chemical agent site and a polypeptide site has also been considered. However, in a case where a compound having a group represented by the formula (L1) or (L2) is used as a chelating chemical agent, it has become apparent from the experiments of the inventors that when a linking group having the thiourea structure is introduced, the degradation by a renal brush border membrane enzyme does not proceed. On the other hand, it has become apparent that by introducing a linking group having a specific structure as in the compound represented by the formula (1), the degradation by a renal brush border membrane enzyme proceeds, and the accumulation of radioactivity in the kidney can be reduced.

As to the compound (1) or the like according to the present invention, in the formula (1), from the viewpoint of reducing the accumulation in the kidney from an early stage of administration, an amino acid sequence of from $A_1$ to $A_4$ (with an amino acid sequence of from $A_1$ to $A_3$ in a case of n=0) is preferably the same as a part of a substrate sequence of a renal brush border membrane enzyme.

From the viewpoint of reducing the accumulation in the kidney from an early stage of administration, $A_1$ is preferably a residue of phenylalanine, methionine, valine, leucine, isoleucine, proline, tyrosine, glycine, alanine, or tryptophan, and more preferably a residue of phenylalanine, glycine, alanine, or methionine, and from the viewpoint of making the effect of reducing the accumulation in the kidney from an early stage of administration more remarkable, $A_1$ is furthermore preferably a residue of phenylalanine.

From the viewpoint of reducing the accumulation in the kidney from an early stage of administration, $A_2$ is preferably a residue of glycine, phenylalanine, methionine, valine, leucine, isoleucine, proline, tyrosine, alanine, or tryptophan, and more preferably a residue of glycine, phenylalanine, alanine, valine, or isoleucine, and from the viewpoint of making the effect of reducing the accumulation in the kidney from an early stage of administration more remarkable, $A_2$ is furthermore preferably a residue of glycine.

In this regard, m is an integer of 0 to 3, and preferably 1.

From the viewpoint of introducing a functional group capable of binding to a polypeptide or a linking group thereof to a side chain of an amino acid sequence, $A_3$ is an amino acid residue having an amino group or a carboxy group on the side chain, preferably a residue of lysine, ornithine, arginine, aspartic acid, or glutamic acid, more preferably a residue of lysine, ornithine, or arginine, and furthermore preferably a residue of lysine.

In this regard, as $A_4$, another amino acid residue may be included. As $A_4$, any amino acid is used.

n is an integer of 0 to 3, and preferably 0.

$R_1$ is a group having a functional group capable of binding to a target molecule recognition element or a linking group thereof, or is a hydrogen atom of an amino group or a carboxy group on a side chain of $A_2$, and binds to an amino group or a carboxy group on a side chain of $A_3$. Meanwhile, $R_1$ may form a heterocyclic group having 3 to 10 carbon atoms including a nitrogen atom of the amino group on the side chain of $A_3$ as a ring-constituting atom.

$R_1$ functions as a spacer, and can bind a target molecule recognition element such as a polypeptide to the compound of the present invention via a functional group. By binding to the amino group or the carboxy group on the side chain of $A_3$, $R_1$ can bind the compound of the present invention to a polypeptide without chemically modifying the amino acid sequence end.

$R_1$ may bind to the nitrogen atom of the amino group on the side chain, or may form an ester bond to the carboxy group on the side chain.

The functional group of $R_1$, which is capable of binding to a target molecule recognition element or a linking group thereof, is not particularly limited, and examples of the functional group include a carboxy group or an active ester thereof; a group having a C=C bond such as a maleimide group, or an acryloyl group; and at least one kind of functional group (hereinafter, also referred to as "functional group a") selected from the group consisting of a carbamoyl group, an isothiocyanate group, and an amino group. Examples of the active ester of a carboxy group include a chloroacetyl group, a bromoacetyl group, and an iodoacetyl group. Among them, as the functional group a, a group having a C=C bond, or a carbamoyl group is preferred. The total number of carbon atoms of $R_1$ is not particularly limited, and is, for example, preferably 1 or more, more preferably 2 or more, and furthermore preferably 3 or more, and further, is preferably 20 or less, more preferably 10 or less, and furthermore preferably 8 or less.

Examples of the $R_1$ include an acyl group having 2 to 20 carbon atoms in total having a functional group a, an alkyl group having 2 to 20 carbon atoms in total having a functional group a, an alkylcarbamoyl group having 2 to 20 carbon atoms in total having a functional group a, and an alkylthiocarbamoyl group having 2 to 20 carbon atoms in total having a functional group a.

In a case where $R_1$ forms a heterocyclic group, the heterocyclic group is preferably a maleimide group.

In a case where $R_1$ forms a heterocyclic group, the number of carbon atoms of the heterocyclic group is preferably 3 to 10, more preferably 3 to 5, and furthermore preferably 4 or 5.

$R_1$ may also be a hydrogen atom of the amino group or the carboxy group on the side chain of $A_3$. That is, the amino group or carboxy group of $A_3$ may be a group that is not modified.

In particular, $R_1$ is preferably a heterocyclic group having 3 to 10 carbon atoms including a nitrogen atom of the amino group on the side chain of $A_3$ as a ring-constituting atom, and more preferably a maleimide group including a nitrogen atom of the amino group on the side chain of $A_3$ as a ring-constituting atom.

L represents a group represented by the formula (L1):

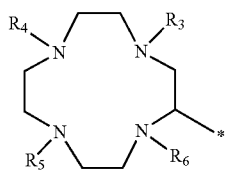
(L1)

or a group represented by the formula (L2):

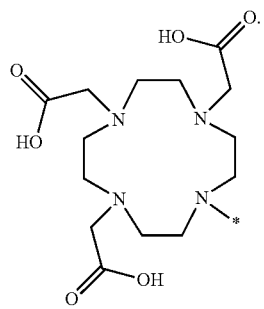
(L2)

With respect to the group represented by the formula (L1), preferably three or more and four or less of $R_3$, $R_4$, $R_5$, and $R_6$ each represent a —$CH_2COOH$ group, and more preferably three of $R_3$, $R_4$, $R_5$, and $R_6$ each represent a —$CH_2COOH$ group.

As the —$CH_2COOR_1$ group, $R_{10}$ represents a hydrogen atom or a hydrocarbon group having 1 to 8 carbon atoms.

Among $R_3$, $R_4$, $R_5$, and $R_6$, a group other than the —$CH_2COOH$ group is preferably a hydrocarbon group having 1 to 8 carbon atoms, and more preferably a hydrocarbon group having 1 to 4 carbon atoms.

From the viewpoint of reducing the accumulation in the kidney, at least one group of $R_3$, $R_4$, $R_5$, and $R_6$ is preferably a hydrocarbon group having 3 to 8 carbon atoms, and more preferably a hydrocarbon group having 4 to 6 carbon atoms.

The hydrocarbon group is preferably an aliphatic hydrocarbon group, and more preferably a branched aliphatic hydrocarbon group.

Examples of the hydrocarbon group include a methyl group, an ethyl group, an n-propyl group, an isopropyl group, an n-butyl group, a sec-butyl group, and an isobutyl group.

Among them, from the viewpoint of reducing the accumulation in the kidney, as the hydrocarbon group, an ethyl group, an n-butyl group, a sec-butyl group, or an isobutyl group is preferred, an n-butyl group, a sec-butyl group, or an isobutyl group is more preferred, and an isobutyl group is furthermore preferred.

Among them, L is preferably a group represented by the formula (L1):

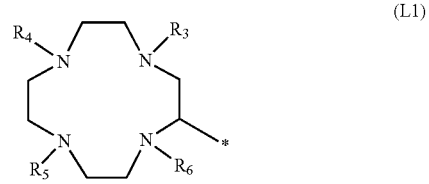
(L1)

wherein $R_3$, $R_4$, $R_5$, and $R_6$ each independently represent a —$CH_2COOH$ group, or a hydrocarbon group having 1 to 8 carbon atoms, and the symbol * represents a binding site, provided that three of $R_3$, $R_4$, $R_5$, and $R_6$ each represent a —$CH_2COOH$ group).

As the L, at least one selected from the group consisting of the formulas (L1-1), (L1-2), (L1-3), (L1-4), (L1-5), (L1-6), (L1-7), (L1-8), (L1-9), and (L2) is preferred.

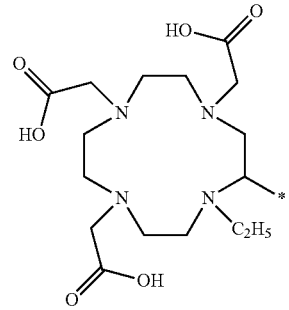
(L1-1)

(L1-2)
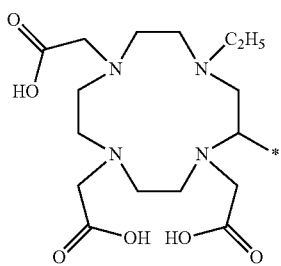

(L1-3)
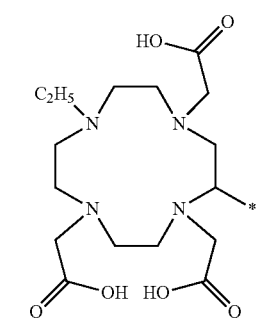

(L1-4)
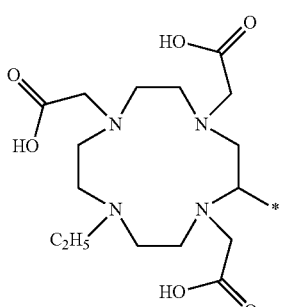

(L1-5)
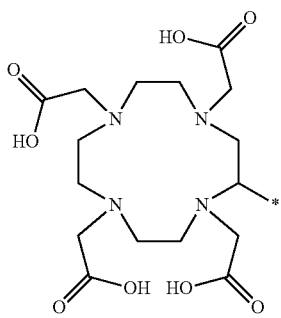

(L1-6)
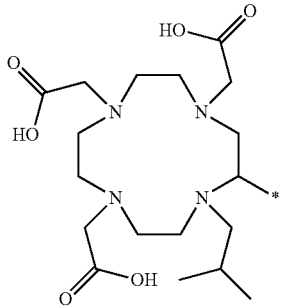

(L1-7)
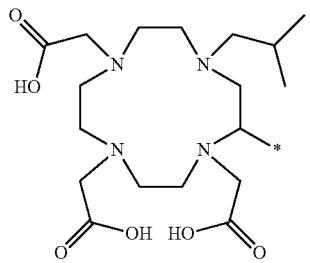

(L1-8)
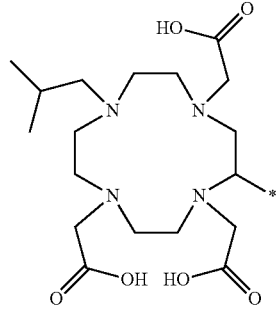

(L1-9)
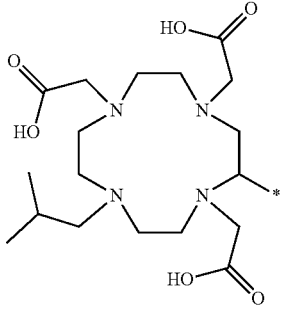

In each of the above formulas, the symbol * represents a binding site.

Among the compounds (1) described above of the present invention, a compound represented by the following formula (1a) is preferred.

(1a)
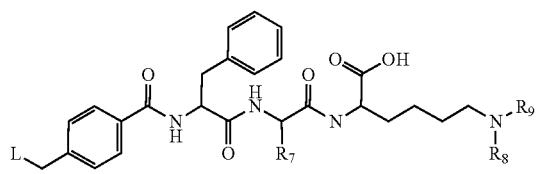

In the formula,
L represents a group represented by the formula (L1):

(L1)
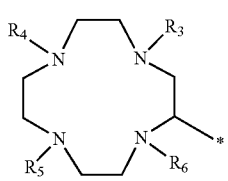

wherein $R_3$, $R_4$, $R_5$, and $R_6$ each independently represent a hydrogen atom, a —$CH_2COOR_{10}$ group, or a hydrocarbon group having 1 to 8 carbon atoms, $R_{10}$ represents a hydrogen atom or a hydrocarbon group having 1 to 8 carbon atoms, and the symbol * represents a binding site, provided that at least three of $R_3$, $R_4$, $R_5$, and $R_6$ each represent a —$CH_2COOH$ group, or a group represented by the formula (L2):

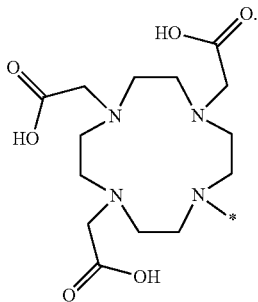

(L2)

wherein the symbol * represents a binding site.

$R_7$ represents a hydrogen atom or a methyl group, $R_8$ and $R_9$ each independently represent a hydrogen atom, or an acyl group having 2 to 20 carbon atoms in total having a functional group a, an alkyl group having 2 to 20 carbon atoms in total having a functional group a, an alkylcarbamoyl group having 2 to 20 carbon atoms in total having a functional group a, or an alkylthiocarbamoyl group having 2 to 20 carbon atoms in total having a functional group a, provided that $R_8$ and $R_9$ may form a heterocyclic ring including an adjacent nitrogen atom, and in that case, a group represented by the formula:

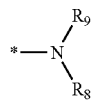

is a group represented by the formula:

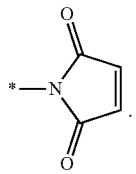 [SMILES: *N1C(=O)C=CC1=O]

$R_8$ and $R_9$ each preferably represent an acyl group having 2 to 20 carbon atoms in total having a functional group a, and more preferably an acyl group having 3 to 6 carbon atoms in total having a carbamoyl group. As the acyl group having 3 to 6 carbon atoms in total having a carbamoyl group, for example, a group represented by the formula: —C(=O)(CH$_2$)$_a$(=O)NH$_2$ wherein a is an integer of 1 to 4 can be mentioned.

In the compound represented by the above formula (1a), preferably, L in the formula represents a group represented by the formula (L1):

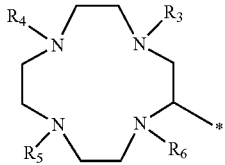

(L1)

wherein $R_3$, $R_4$, $R_5$, and $R_6$ each independently represent a —$CH_2COOH$ group, or a hydrocarbon group having 1 to 8 carbon atoms, and the symbol * represents a binding site, provided that three of $R_3$, $R_4$, $R_5$, and $R_6$ each represent a —$CH_2COOH$ group, and one of $R_3$, $R_4$, $R_5$, and $R_6$ represents a hydrocarbon group having 1 to 8 carbon atoms, more preferably, L in the formula represents a group represented by the formula (L1):

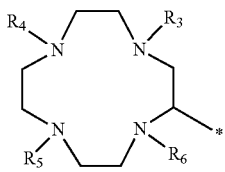

(L1)

wherein $R_3$, $R_4$, $R_5$, and $R_6$ each independently represent a —$CH_2COOH$ group, an ethyl group, or a butyl group, and the symbol * represents a binding site, provided that three of $R_3$, $R_4$, $R_5$, and $R_6$ each represent a —$CH_2COOH$ group, and one of $R_3$, $R_4$, $R_5$, and $R_6$ represents an ethyl group, or a butyl group, and furthermore preferably, L in the formula represents a group represented by the formula (L1):

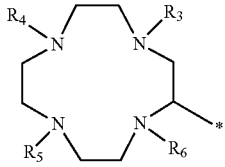

(L1)

wherein $R_3$, $R_4$, $R_5$, and $R_6$ each independently represent a —$CH_2COOH$ group, or an isobutyl group, and the symbol * represents a binding site, provided that three of $R_3$, $R_4$, $R_5$, and $R_6$ each represent a —$CH_2COOH$ group, and one of $R_3$, $R_4$, $R_5$, and $R_6$ represents an isobutyl group.

Preferred specific examples of the above-described compound (1) of the present invention include the following compounds 1-1 to 1-6.

1-1

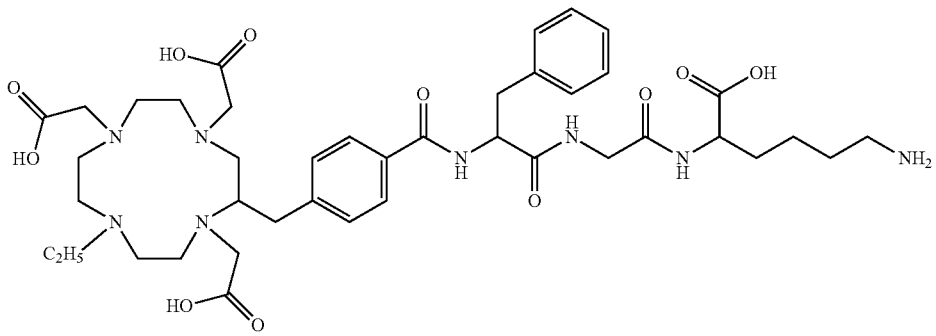

CDO3AEt-FGK

-continued
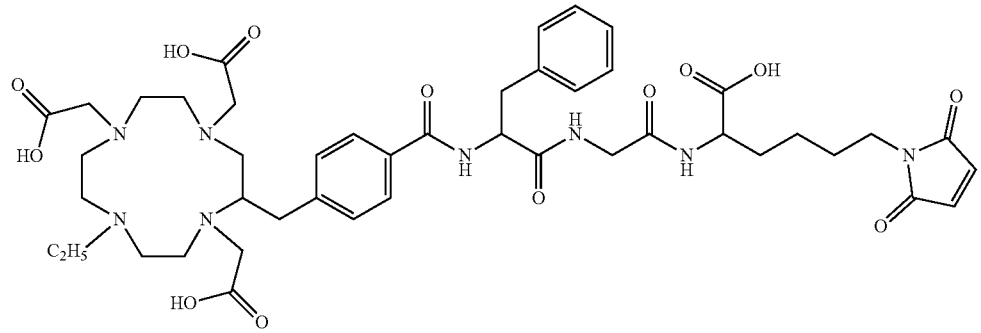
CDO3AEt-FGK(Mal)
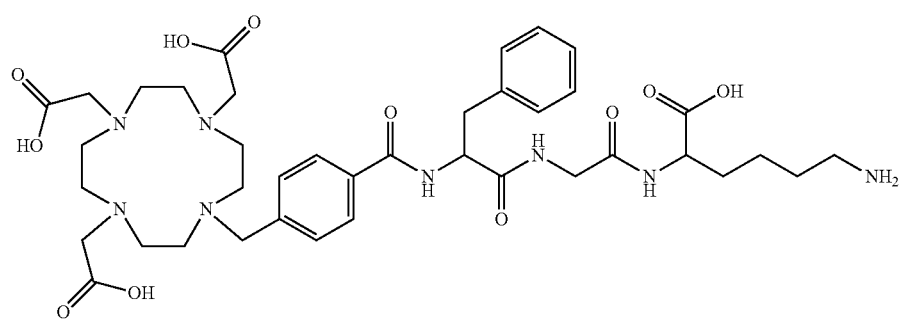
DO3A-Bn-CO-FGK
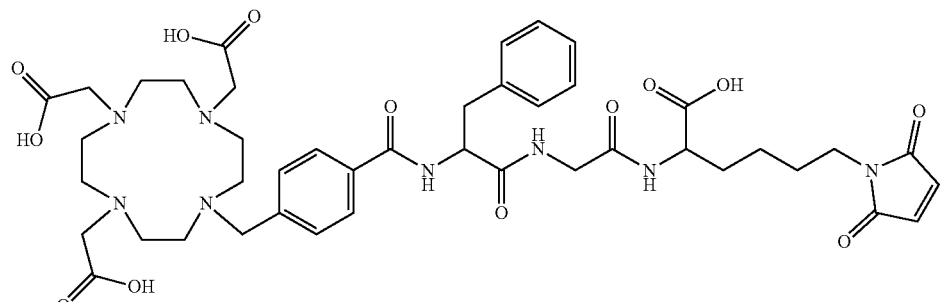
DO3A-Bn-CO-FGK(Mal)
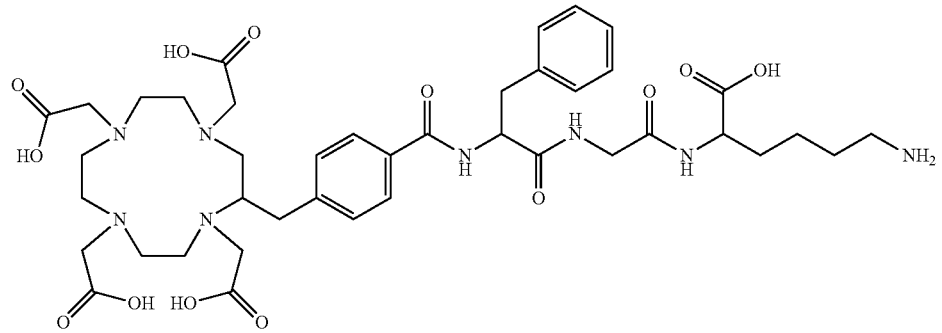
CDOTA-Bn-CO-FGK

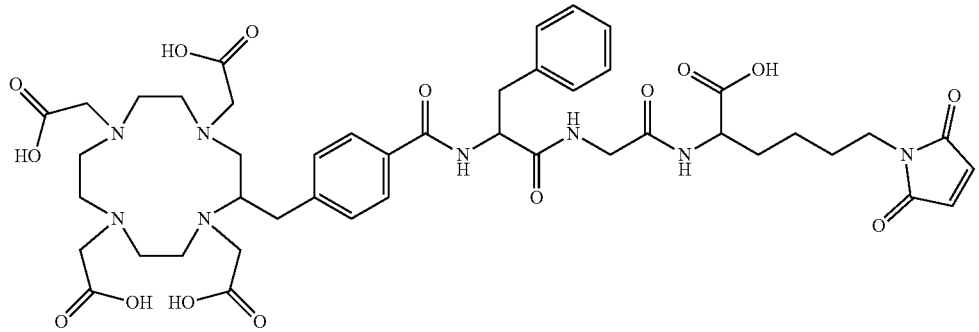

CDOTA-Bn-CO-FGK(Mal)

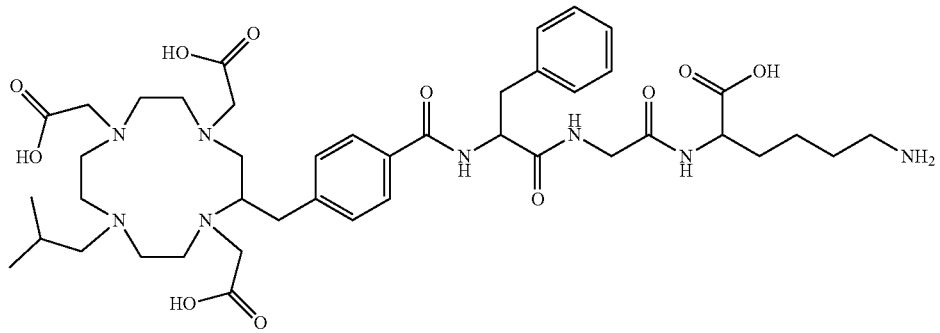

CDO3AiBu-FGK

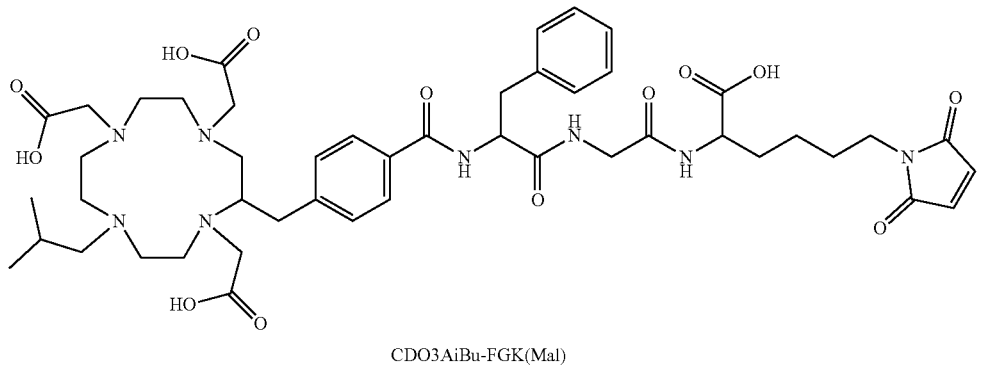

CDO3AiBu-FGK(Mal)

The compound (1) or the like according to the present invention may also be a pharmacologically acceptable salt of each of the above compounds.

Examples of the pharmacologically acceptable salt include an acid addition salt, and a base addition salt.

As the acid addition salt, any of an inorganic acid salt and an organic acid salt may be adopted.

Examples of the inorganic acid salt include a hydrochloride, a hydrobromide, a sulfate, a hydroiodide, a nitrate, and a phosphate.

Examples of the organic acid salt include a citrate, an oxalate, an acetate, a formate, a propionate, a benzoate, a trifluoroacetate, a maleate, a tartrate, a methanesulfonate, a benzenesulfonate, and a p-toluenesulfonate.

As the base addition salt, any of an inorganic base salt and an organic base salt may be adopted.

Examples of the inorganic base salt include a sodium salt, a potassium salt, a calcium salt, a magnesium salt, and an ammonium salt.

Examples of the organic base salt include a triethylammonium salt, a triethanolammonium salt, a pyridinium salt, and a diisopropylammonium salt.

<Compound (2) or the Like>

The compound (2) or the like according to the present invention is a compound having a target molecule recognition element bound to a compound (1) or a pharmacologically acceptable salt of the compound (1), or a pharmacologically acceptable salt thereof. The target molecule recognition element may be bound to the compound (1) or a pharmacologically acceptable salt thereof via a linking group, or may be directly bound to the compound (1) or a pharmacologically acceptable salt thereof. As the linking group, iminothiol derived from 2-iminothiolane can be mentioned.

Target Molecule Recognition Element

The term "target molecule recognition element" is referred to as a molecule, a substituent, a functional group, or an atomic group, which is capable of recognizing a target molecule, for example, binding to a target molecule in a living body.

Examples of the target molecule recognition element include a polypeptide, and in addition, a ligand binding to a target molecule.

The polypeptide is usually a polypeptide binding to a target molecule, and preferably a polypeptide specifically binding to a target molecule. The expression "specifically binding to a target molecule" means that a polypeptide binds to a target molecule, but does not bind or only weakly binds to the other molecules than the target molecule.

The term "target molecule" is referred to as a molecule present in a target site such as a tissue or a cell to be diagnosed by a radioactive drug, and preferably referred to as a molecule that is specifically expressed therein. The expression "specifically expressed" means that a molecule is expressed in a target site, but is not expressed or is only lowly expressed in the other sites than the target site.

Examples of the target molecule recognition element include a ligand binding to a protein that is highly expressed in tissue construction associated with inflammation, tumor cell invasion or the like, or binding to a protein that is specifically expressed in a tumor cell; an antibody; and an antigen-binding domain fragment of an antibody.

As the antibody, for example, a monoclonal antibody such as an anti-CD25 antibody, or an anti-CD20 antibody can be mentioned.

Examples of the antigen-binding domain fragment of an antibody include a Fab fragment (hereinafter, also simply referred to as "Fab"), a F(ab')$_2$ fragment, a F(ab)$_2$ fragment, and a variable region fragment (hereinafter, also referred to as "Fv fragment").

The term "Fab fragment" means a product on the N-terminal side of an antibody, which is generated by papain digestion, and a fragment having a domain structure similar to that of the product.

The term "F(ab')$_2$ fragment" means a fragment obtained by reducing a disulfide bond in a hinge region of F(ab')$_2$ of an antibody, and a fragment having a domain structure similar to that of the fragment above.

The term "F(ab)$_2$ fragment" means a dimer obtained by binding two molecules of Fab fragments to each other by a disulfide bond.

The term "Fv fragment" means a minimal fragment of an antibody, which has a binding activity to an antigen.

Examples of the antigen-binding domain fragment of an antibody include, more specifically, an antibody to a protein that is specifically expressed in a specific cancer cell, and a Fab fragment or Fv fragment of the antibody.

As another target molecule recognition element, a cyclic pentapeptide that has an affinity for integrin highly expressed in a newborn blood vessel of a cancer, for example, cyclo-Arg-Gly-Asp-D-Phe-Lys (hereinafter, also referred to as "c(RGDfK)") can be mentioned. In addition, bisphosphonic acid, oligo-aspartic acid, and oligo-glutamic acid that each have an affinity for hydroxyapatite present in a large amount in an osteoblastic cancer (bonemetastasis), fMet-Leu-Phe (fMLP) that is a peptide having an affinity for a receptor for a scanning factor present on a surface of a macrophage, folic acid binding to a folate receptor that is expressed in a cancer cell and a derivative thereof, and the like can be mentioned.

In this regard, the target molecule recognition element is not limited to these polypeptides described above, and any polypeptide can also be used as long as it binds to a target molecule.

The binding of the target molecule recognition element may be performed by introducing a linking group capable of reacting with a functional group of a compound by using, for example, a thiolation reagent such as 2-iminothiolane. With respect to the introduction of the linking group to a Fab fragment, the reaction of the above-described thiolation reagent under the condition of pH 7 to 9 may be carried out to add a sulfhydryl group to an amino group of the Fab fragment.

As the target molecule recognition element, a ligand having an Asn-urea-Lys site or a Glu-urea-Lys site may be used. The ligand selectively binds to a receptor for a prostate specific membrane antigen which expression is significantly increased in prostate cancer.

The Asn-urea-Lys site is a site represented by the formula:

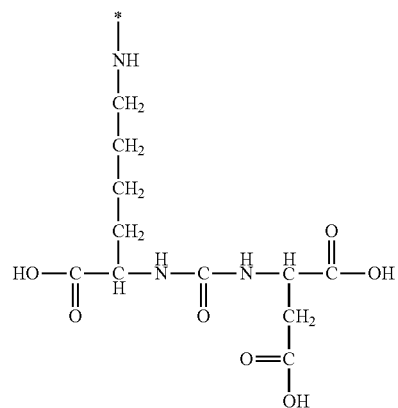 [SMILES: *NCCCCC(NC(=O)NC(CC(=O)O)C(=O)O)C(=O)O]

wherein the symbol * represents a binding site.
The Glu-urea-Lys site is a site represented by the formula:

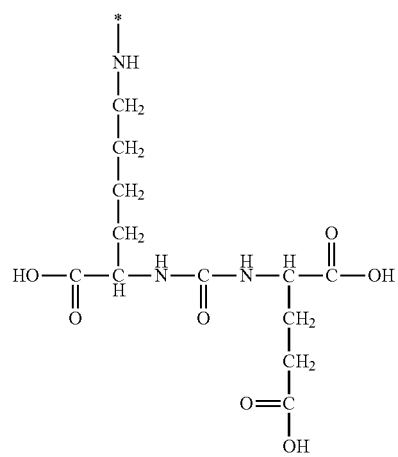 [SMILES: *NCCCCC(NC(=O)NC(CCC(=O)O)C(=O)O)C(=O)O]

wherein the symbol * represents a binding site.

In addition to the above, for example, a method for recognizing a target molecule can be mentioned in which the above-described polypeptide or another ligand binding to a target molecule, into which a specific functional group $f_1$ has been introduced, is allowed to bind to a target molecule for example, a protein that is highly expressed in tissue construction associated with inflammation, tumor cell invasion or the like, or a protein that is specifically expressed in a tumor cell, and a compound (2) or the like having a functional group $f_2$ that reacts with the functional group $f_1$ to form binding is administered as a target molecule recognition element (Chemical Society Reviews 45: 6409-6658, 2016, and Chemical Society Reviews 42: 5131-5142, 2013).

As the functional group $f_1$, for example, a group represented by the following formula ($f_1$-1), ($f_1$-2), or ($f_1$-3) can be mentioned.

$$*-N_3 \qquad (f_1\text{-}1)$$

-continued (f₁-2)

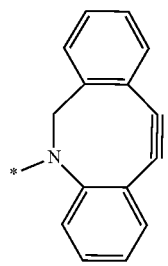

(f₁-3)

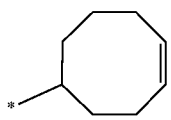

wherein the symbol * represents a binding site.

As the functional group f₂, for example, a group represented by the following formula (f₂-1), (f₂-2), (f₂-3), (f₂-4), or (f₂-5) can be mentioned.

(f₂-1)

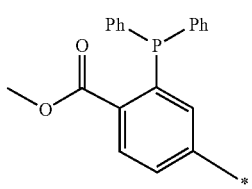

(f₂-2)

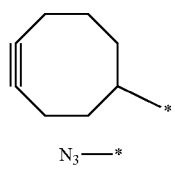

(f₂-3)

$N_3$—*

(f₂-4)

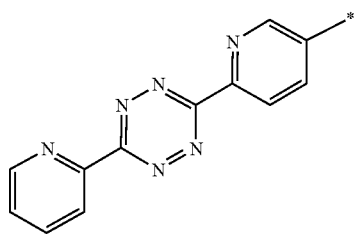

(f₂-5)

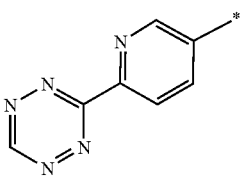

wherein the symbol * represents a binding site.

The compound (2) or the like according to the present invention can be used to provide a drug for preparing a radioactive drug containing the compound.

The drug for preparing a radioactive drug may contain a pH regulator such as an aqueous buffer solution, a stabilizer such as ascorbic acid, or p-aminobenzoic acid, and the like, in addition to the compound.

As the compound (2) or the like according to the present invention, for example, a compound represented by the following formula (2), or a pharmacologically acceptable salt thereof can be mentioned.

(2)

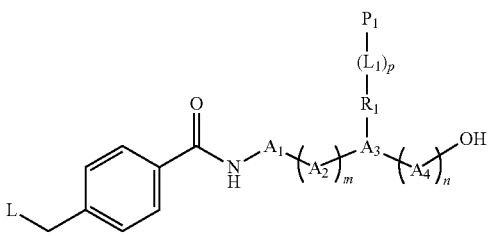

wherein $A_1$, $A_2$, m, $A_3$, $A_4$, n, $R_1$, and L are the same as those in the formula (1), $L_1$ represents a linking group linking $R_1$ and $P_1$, p is 0 or 1, $P_1$ represents a target molecule recognition element.

$L_1$ forms binding with a functional group capable of linking to a linking group of $R_1$, and also forms binding with a target molecule recognition element. $L_1$ is preferably iminothiol derived from 2-iminothiolane, or the like.

p is preferably 1.

$P_1$ represents, for example, the above-described target molecule recognition element, and is preferably a ligand binding to a polypeptide, or other target molecules or a functional group $f_2$ represented by the formula ($f_2$-1), ($f_2$-2), ($f_2$-3), ($f_2$-4), or ($f_2$-5).

Preferred specific examples of the above-described compound (2) according to the present invention include the following compounds 2-1 to 2-4. In this regard, the Fab in each of the following formulas means a Fab fragment site.

2-1

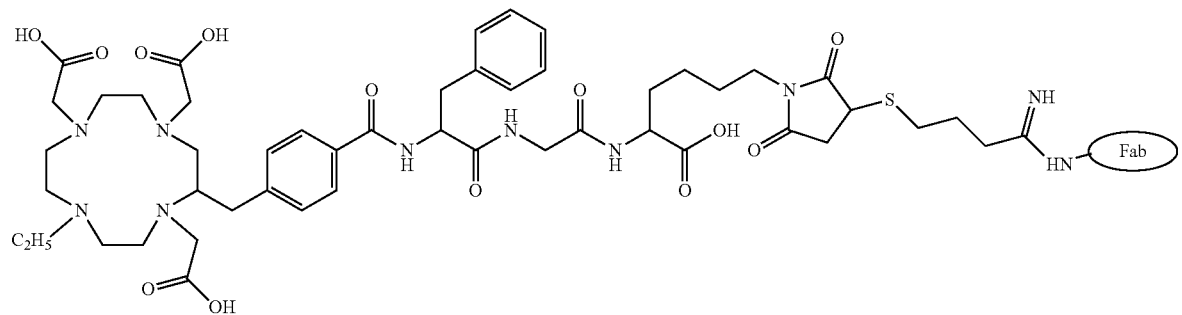

CDO3AEt-FGK-Fab

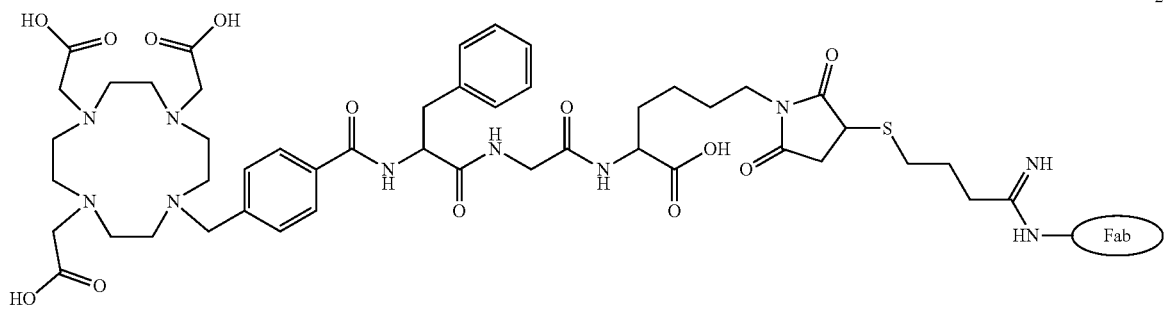

CDO3AEt-FGK-Fab

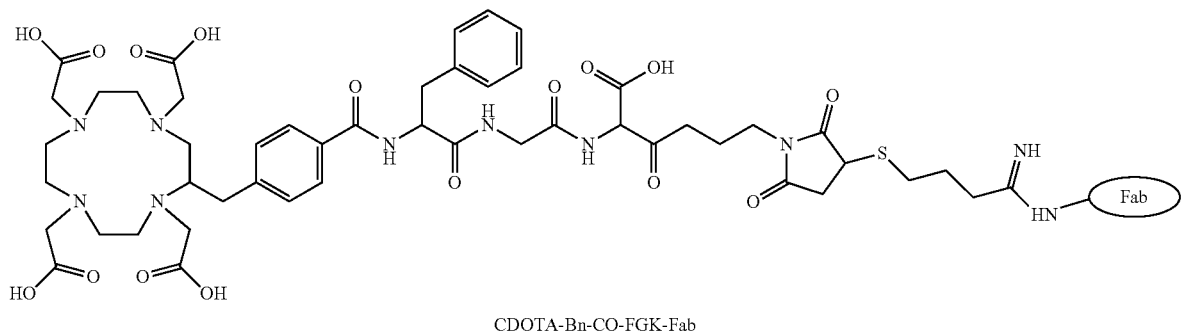

CDOTA-Bn-CO-FGK-Fab

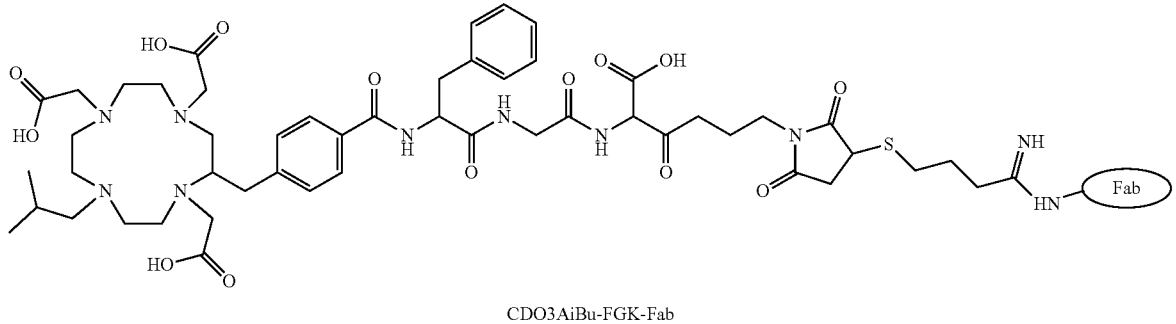

CDO3AiBu-FGK-Fab

<Metal Complex Compound (3) or the Like>

The metal complex compound or pharmacologically acceptable salt thereof according to the present invention (hereinafter, also referred to as "metal complex compound (3) or the like") comprises a metal selected from the group consisting of a radioactive metal, and a radioactive atom-labeled metal, and a compound or pharmacologically acceptable salt thereof of the present invention coordinated to the metal.

The radioactive drug containing the metal complex compound (3) or the like according to the present invention may contain an unreacted material or impurity in addition to the metal complex compound (3) or the like, or may contain a metal complex compound (3) or the like that has been purified by a high performance liquid chromatography (HPLC) method or the like after production.

The term "complex" means a substance in which a ligand is coordinated with an atom or ion of a metal or metal-like element as the center, and is also referred to as a coordination compound. The coordination means that a ligand forms a coordination bond to the metal as the center and is arranged around the central metal. The complex is formed by a coordination bond between a ligand and a metal. The formation of a complex between a ligand and a metal may be referred to as complex formation. The coordination bond means a bond in which two valence electrons participating in one bond are provided from only one atom.

Metal

Examples of the metal include $^{111}$In, $^{223}$Ra, $^{67}$Ga, $^{68}$Ga, $^{44}$Sc, $^{90}$Y, $^{177}$Lu, $^{225}$Ac, $^{212}$Bi, $^{213}$Bi, $^{212}$Pb, $^{227}$Th, $^{64}$Cu, and $^{67}$Cu. The metal is preferably at least one selected from the group consisting of $^{111}$In, $^{223}$Ra, $^{67}$Ga, $^{68}$Ga, $^{90}$Y, $^{177}$Lu, $^{225}$Ac, $^{212}$Bi, $^{213}$Bi, $^{212}$Pb, and $^{227}$Th, more preferably at least one selected from the group consisting of $^{111}$In, $^{90}$Y, $^{177}$Lu, $^{225}$Ac, $^{212}$Bi, $^{213}$Bi, and $^{212}$Pb, and furthermore preferably $^{111}$In, $^{90}$Y, $^{177}$Lu and $^{225}$Ac.

The metal is not limited to these specific examples, and any metal can be used as long as it has a radioactive ray, a radiation dose, and a half-life period, which are suitable for the purpose of, for example, diagnosis using a radiolabeled drug. From the viewpoint of reducing the effect on normal tissues and cells in radiological imaging diagnosis, a short-half-life radioactive isotope of a metal is preferably used.

Production of the metal complex compound (3) or the like can be performed by in vitro complex formation with a radioactive isotope of a metal using the above compound bound to a target molecule recognition element as a ligand. The complex formation can be performed by a simple operation utilizing a conventionally known complex formation reaction.

The metal complex compound (3) according to the present invention may include, for example, a metal complex compound represented by the following formula (3-1) as the case where L of a compound (1) is a group represented by the formula (L1-4), (L1-5), (L1-9), or (L2).

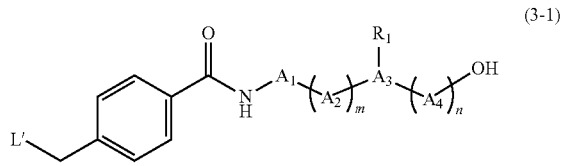
(3-1)

wherein $A_1$, $A_2$, m, $A_3$, $A_4$, n, and $R_1$ are the same as those in the formula (1), and L' is a group represented by the formula (L1'-4), (L1'-5), (L1'-9), or (L2'):

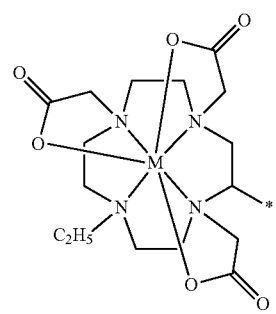
(L1'-4)

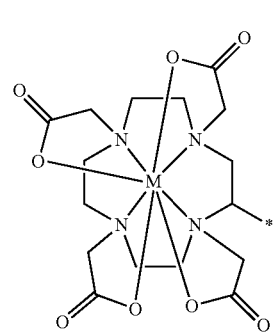
(L1'-5)

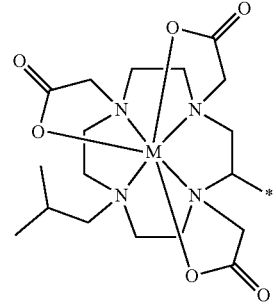
(L1'-9)

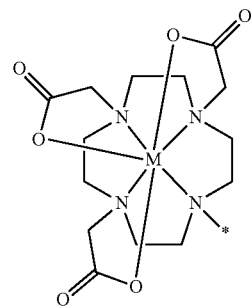
(L2')

wherein M is $^{111}$In, $^{223}$Ra, $^{67}$Ga, $^{68}$Ga, $^{44}$Sc, $^{90}$Y, $^{177}$Lu, $^{225}$Ac, $^{212}$Bi, $^{213}$Bi, $^{212}$Pb, $^{227}$Th, $^{64}$Cu, or $^{67}$Cu.

The metal complex compound (3) according to the present invention may include, for example, a metal complex compound represented by the following formula (3-2) as the case where L of a compound (2) is a group represented by the formula (L1-4), (L1-5), (L1-9), or (L2)

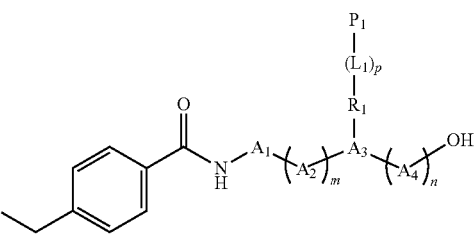
(3-2)

wherein $A_1$, $A_2$, m, $A_3$, $A_4$, n, and $R_1$ are the same as those in the formula (1), $L_1$, p, and $P_1$ are the same as those in the formula (2), and L' is a group represented by the formula (L1'-4), (L1'-5), (L1'-9), or (L2'):

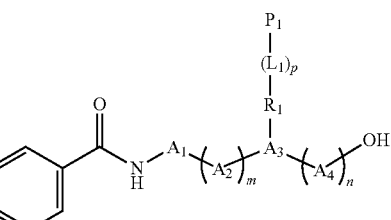
(L1'-4)

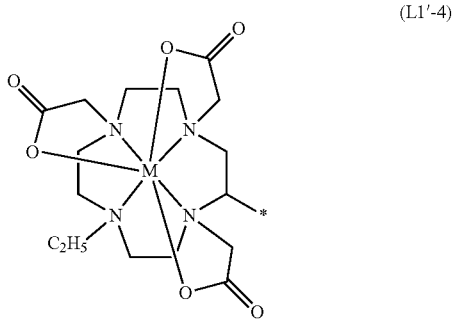
(L1'-5)

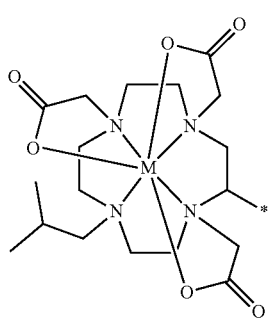

(L1'-9)

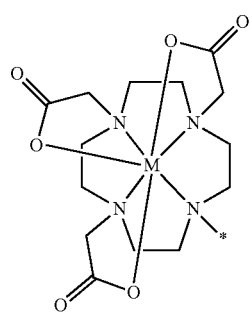

(L2')

wherein M is $^{111}$In, $^{223}$Ra, $^{67}$Ga, $^{68}$Ga, $^{44}$Sc, $^{90}$Y, $^{177}$Lu, $^{225}$Ac, $^{212}$Bi, $^{213}$Bi, $^{212}$Pb, $^{227}$Th, $^{64}$Cu, or $^{67}$Cu.

The radioactive drug according to the present invention can be prepared as a pharmaceutical composition containing the above-described radiolabeled polypeptide as an active component, and further containing one kind or two or more kinds of pharmaceutically acceptable carriers (pharmaceutical carriers) as needed. Examples of the pharmaceutical carrier include a pH regulator such as an aqueous buffer solution, an acid or a base, a stabilizer such as ascorbic acid or p-aminobenzoic acid, an excipient such as D-mannitol, an isotonizing agent, and a preservative. Further, into the radioactive drug, a compound such as citric acid, tartaric acid, malonic acid, sodium gluconate or sodium glucoheptonate, which is helpful in improving radiochemical purity, may be added. The radioactive drug according to the present invention can be provided in any form of an aqueous solution, a frozen solution, and a freeze-dried product.

The kit of the present invention includes the above compound, and a reagent containing the above metal, as separate packaging units.

Examples of the kit of the present invention include a kit including a compound (1) or the like, a reagent containing a target molecule recognition element, and a reagent containing a metal selected from the group consisting of a radioactive metal and a radioactive atom-labeled metal, as separate packaging units; and a kit including a compound (2) or the like having a target molecule recognition element bound to a compound (1) or the like, and a reagent containing a metal selected from the group consisting of a radioactive metal and a radioactive atom-labeled metal, as separate packaging units.

In each of the compounds and reagents included in the kits, one kind or two or more kinds of pharmaceutically acceptable carriers (pharmaceutical carriers) as described above can be contained as needed.

Production method A compound (1) or the like according to the present invention, and a compound (2) or the like having a target molecule recognition element bound to the compound (1) or the like can be synthesized using a known method, and can be produced, for example, by a method described in Examples of the present specification.

A metal complex compound (3) or the like according to the present invention can be produced by forming a complex in vitro with a radioactive metal or a radioactive atom-labeled metal using a compound (2) or the like as a ligand. The complex formation can be performed by a known method.

Usage and Dosage

The metal complex compound or the like according to the present invention is used as, for example, a radioactive drug that is used for radiation therapy or radiological imaging diagnosis.

The metal complex compound or the like according to the present invention can be used for radiation therapy for suppressing a cancer by administering an effective amount thereof to a mammal including a human. In a case where the metal complex compound or the like is used as an anticancer agent, the radiation therapy has the broadest meaning including both of, for example, a prophylactic action of preventing the development, metastasis and implantation, and recurrence of a cancer, and a therapeutic action of suppressing the growth of cancer cells, of blocking the progress of a cancer by shrinking the cancer, and of improving the symptoms, and should not be construed as being limited in any case.

Examples of a metal selected from the group consisting of a radioactive metal and a radioactive atom-labeled metal, used as a radiotherapeutic agent include an alpha-ray emitting nuclide, a beta-ray emitting nuclide, a gamma-ray emitting nuclide, and a positron emitting nuclide. Among them, for use in radiation therapy, a beta-ray emitting nuclide (that is, a nuclide that emits β rays) is preferred.

Examples of the radiological imaging diagnosis include single photon emission computed tomography (hereinafter also simply referred to as "SPECT"), and positron emission tomography (hereinafter also simply referred to as "PET").

The diagnosis is not particularly limited, and is used as radiological imaging diagnosis or the like for various kinds of diseases such as a tumor, inflammation, infections, a cardiovascular disease, and a brain and central nervous system disease, and for organs and tissues, and preferably used as radiological imaging diagnosis for a cancer.

By selecting a target molecule recognition element according to the characteristics of a target to be diagnosed, diagnosis and treatment of a wide variety of targets can be realized, and the radioactive drug according to the present invention can be widely used as a radioactive diagnostic imaging agent in the field of diagnosis.

As the administration route of the radioactive drug according to the present invention, for example, parenteral administration such as intravenous administration or intraarterial administration, or oral administration can be mentioned, and intravenous administration is preferred.

The administration route is not limited to the routes described above, and any route can be used as long as it is a route capable of expressing the action effectively after administration of the radioactive drug.

The intensity of the radioactivity of the radioactive drug according to the present invention is arbitrarily selected as long as it is an intensity at which the purpose can be achieved by administering the radioactive drug, and further corresponds to a clinical dose at which radiation exposure for the subject can be made as low as possible.

The radioactive intensity can be determined with reference to the intensity of radioactivity used in general diagnostic and therapeutic methods using a radioactive drug. As for the dose, radioactivity and dose that are considered to enable an imaging are determined in consideration of various conditions such as the age and weight of a patient, an appropriate radiation imaging device, the condition of a disease to be targeted, and the like.

In a case where a human is targeted, the amount of radioactivity in the radioactive drug is as follows.

In general, assuming that the radioactive drug is expected to be used for radiation therapy, the dose of the diagnostic drug is not particularly limited but is, for example, 1.0 MBq/kg to 3.0 MBq/kg as an amount of radioactivity of a radioactive metal (for example, $^{111}$In).

As described above, according to the present invention, a compound that can give a radioactive drug capable of reducing the accumulation thereof in the kidney from an early stage of administration can be provided.

EXAMPLES

The Examples of the present invention described below are for illustrative purposes only, and do not limit the technical scope of the present invention. In addition, the following experiments were performed after approval by the Animal Ethics Committee of Chiba University.

In the following Examples and Comparative Examples, the following abbreviations were used for substituents, compounds, and organic solvents, respectively.

Fmoc: fluorenylmethoxycarbonyl group
Boc: tert-butoxycarbonyl group
THF: tetrahydrofuran
NMM: N-methylmorphiline
DMF: dimethylformamide
Tfa: trifluoroacetate group
DCC: N,N'-dicyclohexylcarbodiimide
Trt(2-Cl): 2-chlorotrityl group
Cl-Trt(2-Cl) Resin: 2-chlorotrityl chloride resin
Fmoc-Lys(Dde)-OH: N-α-(9-fluorenylmethoxycarbonyl)-N-ε-[1-(4,4-dimethyl-2,6-dioxocyclohexylidene)ethyl]-L-lysine
TFA: trifluoroacetic acid
MeCN: acetonitrile
DIPEA: N,N-diisopropylethylamine
DIC: N,N'-diisopropylcarbodiimide
HOBt: 1-hydroxybenzotriazole
NMCM: N-methoxycarbonylmaleimide
EDTA: ethylenediamine tetraacetic acid
DPS: 2,2'-dipyridyldisulfide
EtOH: ethanol
FBS: fetal bovine serum
D-PBS: Dulbecco's phosphate buffered saline
EGTA: glycol ether diaminetetraacetic acid
Measurement Method and Experimental Animal In the following Examples and Comparative Examples, various kinds of properties and the like were measured in the following manners.
NMR (Nuclear Magnetic Resonance)

For the analysis by $^1$H-NMR, a JEOL ECS-400 spectrometer (available from JEOL Ltd.) was used.
ESI-MS (Electrospray Ionization Mass Spectrometry)

For the analysis by ESI-MS, a HPLC 1200 series-6130 quadrupole LC/MS mass spectrometer (available from Agilent Technologies, Inc.) was used.
Thin Layer Chromatography (TLC)

For the analysis by thin layer chromatography (TLC), a silica plate (TLC aluminium sheets Silica gel 60 RP-18 $F_{254}$s, available from Merck KGaA) was used. The silica plate in which a developing solvent of 0.1 M ammonium acetate aqueous solution:methanol=1:1 had been developed by 10 cm was cut into fractions each having a size of 5 mm, and the radioactivity of each of the fractions was measured by an auto well gamma system (WIZARD3, available from PerkinElmer, Inc).
Cellulose Acetate Electrophoresis (CAE)

In cellulose acetate electrophoresis (hereinafter also referred to as "CAE"), a cellulose acetate membrane (AD-VANTEC SELECA-V, available from Toyo Roshi Kaisha, Ltd.) was cut into fractions each having a size of 11 cm×1 cm, and by using each of the fractions as an electrophoresis membrane, and a veronal buffer (pH 8.6, I=0.06) or a solvent 2 (20 mM P.B. (pH 6.0)) as a buffer solution, the electrophoresis was performed at a constant current (1 mA/cm). The cellulose acetate membrane after the electrophoresis was cut into fractions each having a size of 5 mm, and the radioactivity of each of the fractions was measured by an auto well gamma system.
Reversed-Phase High Performance Liquid Chromatography (RP-HPLC) and Size-Exclusion High Performance Liquid Chromatography (SE-HPLC)
Analysis For the analysis by reversed-phase high performance liquid chromatography (hereinafter also referred to as "RP-HPLC"), L-7405 (available from Hitachi, Ltd.) as a UV detector, L-7100 (available from Hitachi, Ltd.) as a liquid feeding pump, and Cosmosil 5$C_{18}$-AR-300 column (4.6× 150 mm, available from NACALAI TESQUE, INC.) as a column for analysis were used.

By a linear gradient method in which 0.1% (v/v) TFA/ $H_2O$ (phase A) and 0.1% (v/v) TFA/MeCN (phase B) were used as the mobile phases, and the phases were changed from phase A 95% (v/v) and phase B 5% (v/v) to phase A 70% (v/v) and phase B 30% (v/v) in the period of 0 to 20 minutes, and changed from the phase A 70% (v/v) and the phase B 30% (v/v) to phase A 0% (v/v) and phase B 100% (v/v) in the period of 20 to 40 minutes, the elution was performed at a flow rate of 1.0 mL/min.
Fractionation For the fractionation by RP-HPLC, Cadenza 5CD-C18 column (20×150 mm, available from Imtakt Corporation) connected to a guard column, Cadenza 5CD-C18 guard column (10×8 mm, available from Imtakt Corporation) was used.

By a linear gradient method in which 0.1% (v/v) TFA/ $H_2O$ (phase A) and 0.1% (v/v) TFA/MeCN (phase B) were used as the mobile phases, and the phases were changed from phase A 90% (v/v) and phase B 10% (v/v) to phase A 20% (v/v) and phase B 80% (v/v) in the period of 0 to 30 minutes, and changed from the phase A 20% (v/v) and the phase B 80% (v/v) to phase A 0% (v/v) and phase B 100% (v/v) in the period of 30 to 40 minutes, the elution was performed at a flow rate of 5.0 mL/min.

For the analysis by size-exclusion HPLC (hereinafter, also referred to as "SE-HPLC"), by connecting Cosmosil 5 Diol-300II guard column (7.5×50 mm, available from NAC-ALAI TESQUE, INC.) to Cosmosil 5 Diol-300II (7.5×600 mm, available from NACALAI TESQUE, INC.) and by using a 0.1 M phosphate buffer solution (pH 6.8) as a mobile phase, the elution was performed at a flow rate of 1.0 mL/min.

The eluate was measured for absorbance at 254 nm by RP-HPLC and at 280 nm by SE-HPLC, and for the analysis of a $^{67}$Ga-labeled compound, a γ-ray detector, Gabi star (available from Raytest GmbH) was connected on-line, or the eluate was fractionated at intervals of 0.5 minutes by a fraction collector (Frac-920, available from GE Healthcare Japan), and then the radioactivity was measured by an auto well gamma system to perform the analysis.

Reagent

As the "DO3A-EDA (Mal)" in the following Synthesis Example, which is a compound represented by the following formula, the trade name "B-272" manufactured by Macrocyclics, Inc. was used.

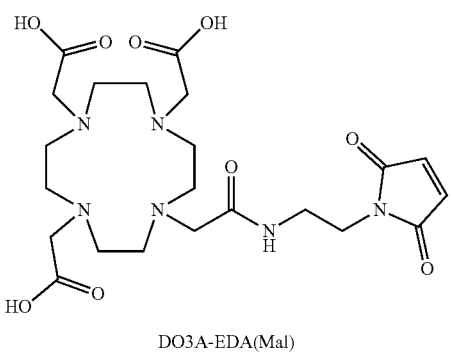 [SMILES: O=C(O)CN1CCN(CC(=O)O)CCN(CC(=O)NCCN2C(=O)C=CC2=O)CCN(CC(=O)O)CC1]

DO3A-EDA(Mal)

Experimental Animal

In the animal experiment, a male ddY-strain SPF mouse aged 6 weeks and a male BALB/c-nu/nu mouse (available from Japan SLC, Inc.) were used.

Synthesis of CDO3AEt-FGK, CDO3AEt-FGK(Mal), and CDO3AEt-FGK (Boc)

Synthesis Example L1: Synthesis of Compound (a13)

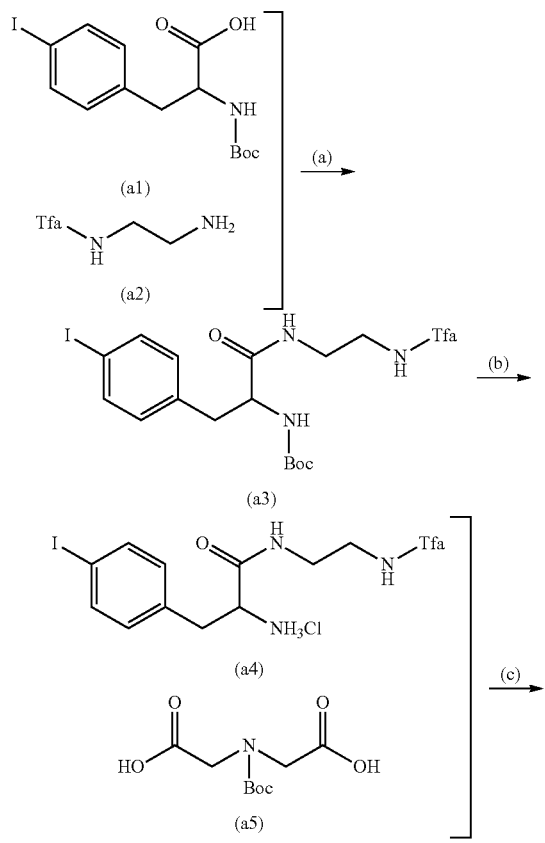

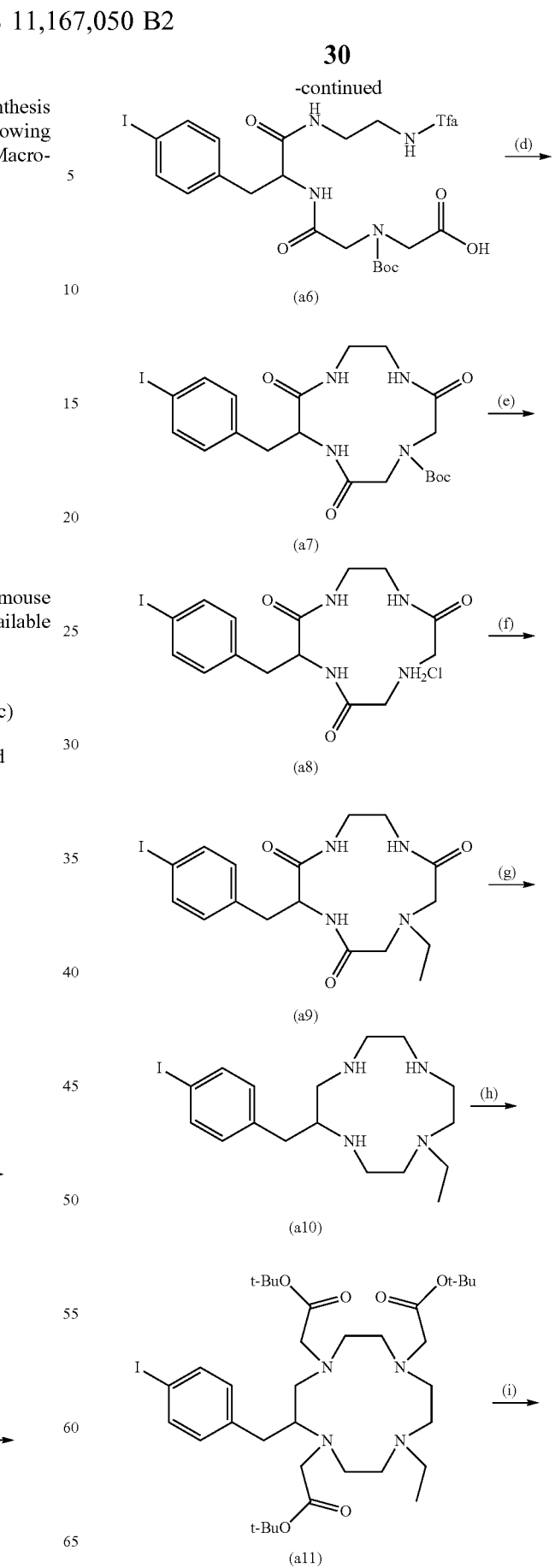

(a12)

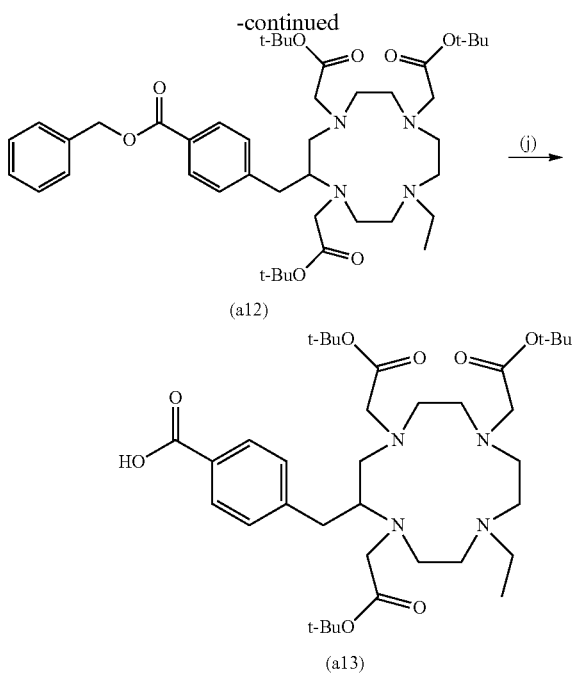

(a13)

(a) Isobutylchloroformate, N-methylmorpholine. THF, DMF; 98% (b) 4N HCl/AcOEt; 99.8% (c) DCC, Et₃N, THF, AcOEt; 91.2% (d) i. 25% NH₃ aq, ii. HATU, HOAt, DIEA 54.2%; (e) 4N HCl/AcOEt 98.4%; (f) Iodoethane, K₂CO₃, MeCN; (g) i. 0.95M BH₃/THF, ii. conc. HCl; (h) tert-butyl bromoacetate, K₂CO₃, MeCN, DMF; (i) Pd(OAc)₂, 1,2-bis(diphenylphosphino)ethane, Et₃N, CO, BnOH, DMF; (j) 10% Pd/C, MeOH Synthesis Example L1(a): Synthesis of Compound (a3)

A compound (a1) (7.97 g, 20.4 mmol) was dissolved in 40 mL of THF, the obtained mixture was cooled to −15° C., and then into the cooled mixture, N-methylmorphiline (NMM, 3.36 mL, 30.5 mmol) and isobutyl chloroformate (4.01 mL, 30.5 mmol) were added in this order under an argon atmosphere. The obtained mixture was stirred for 5 minutes, and then into the resultant mixture, 24 mL of DMF solution of a compound (a2) (5.8 g, 30.5 mmol) and NMM (3.36 mL, 30.5 mmol) was added dropwise, and the obtained mixture was stirred for 30 minutes under cooling and for one hour at room temperature. The solvent was distilled off under reduced pressure, and then the residue was dissolved in 100 mL of ethyl acetate and 100 mL of 5% by mass sodium hydrogen carbonate aqueous solution, and the obtained mixture was washed with a 5% by mass sodium hydrogen carbonate aqueous solution (50 mL×3), and a 5% by mass aqueous solution of citric acid (50 mL×3). The organic layer was dried with the addition of anhydrous magnesium sulfate, and then the crystals obtained by removing the solvent was dried under reduced pressure to obtain a compound (a3) (10.6 g, 20.0 mmol, yield: 98.0%) as pale yellow crystals.

$^1$H NMR (CDCl₃): δ 1.42 [9H, s, Boc], 2.96-3.03 [2H, m, CHCH₂], 3.39-3.51 [4H, CH₂CH₂], 4.22-4.24 [1H, dd, NHCH], 4.85, 6.42, 7.74 [3H, t, NH], 6.93-6.95 [2H, d, CCH], 7.62-7.66 [2H, d, ICCH].

ESI-MS (M+Na)⁺: m/z 552.07. found 552.09.

Synthesis Example L1(b): Compound (a4)

A compound (a3) (10.6 g, 20.0 mmol) was dissolved in 50 mL of 4 N hydrochloric acid/ethyl acetate, the obtained mixture was stirred at room temperature for three hours. The solvent was distilled off under reduced pressure, and the residue was dried under reduced pressure to obtain a compound (a4) (8.08 g, 20.0 mmol, yield: 99.8%) as pale yellow crystals.

$^1$H NMR (CDCl₃): δ 3.42-3.55 [6H, overlapped, CH₂], 3.86-3.88 [1H, dd, CH₂CH], 7.04-7.06 [2H, d, CCH], 7.62-7.64 [2H, d, ICCH].

ESI-MS (M+Na)⁺: m/z 452.02. found 452.03.

Synthesis Example L1(c): Compound (a6)

A compound (a5) (4.45 g, 19.1 mmol) was dissolved in 70 mL of THF, the obtained mixture was ice-cooled, and then into the ice-cooled mixture, 20 mL of THF solution of DCC (4.30 g, 20.8 mmol) was added dropwise under an argon atmosphere. After completion of the dropwise addition, the obtained mixture was stirred at room temperature for one hour, the reaction mixture was filtered to remove dicyclohexyl urea (hereinafter, also referred to as "DC-urea"), and the filtrate was used in the subsequent reaction as an anhydride solution of the compound (a5). A compound (a4) (8.08 g, 17.4 mmol) was suspended in 80 mL of ethyl acetate, into the obtained suspension, Et₃N (3.63 mL, 26.0 mmol) was added, and the obtained mixture was cooled and stirred for 10 minutes, and then into the resultant mixture, the anhydride solution of the compound (a5) prepared previously was added dropwise under an argon atmosphere. After completion of the dropwise addition, the obtained mixture was stirred at room temperature for one hour, and the reaction mixture was washed with a 5% by mass aqueous solution of citric acid (50 mL×3) The organic layer was dried with the addition of anhydrous magnesium sulfate, and then the residue obtained by distilling off the solvent under reduced pressure was purified by silica gel column chromatography using ethyl acetate as an elution solvent to obtain a compound (a6) (10.2 g, 15.8 mmol, yield: 91.2%) as pale yellow crystals.

$^1$H NMR (CDCl₃): δ 1.37 [9H, s, Boc], 3.00-3.19 [2H, m, CHCH₂], 3.42-3.52 [5H, overlapped, NCH₂, NHCH₂], 3.77-4.03 [2H, m, COCH₂], 4.11-4.16 [1H, dd, NCH₂], 4.60-4.62 [1H, t, CH₂CH], 6.96-7.01 [2H, d, CCH], 7.58-7.60 [2H, d, ICCH].

ESI-MS (M+Na)⁺: m/z 667.09. found 667.02.

Synthesis Example L1(d): Compound (a7)

A compound (a6) (3.52 g, 5.46 mmol) was dissolved in 50 mL of 25% by mass ammonia water, and the obtained mixture was stirred at room temperature for three hours. The solvent was distilled off under reduced pressure, and then an oil obtained by drying the residue under reduced pressure and dissolved in 90 mL of DMF was taken as a liquid A. O-(7-aza-1H-benzotriazole-1-yl)-N,N,N',N'-tetramethyluronium hexafluorophosphate (HATU, 3.12 g, 8.21 mmol) dissolved in 90 mL of DMF was taken as a liquid B. DIEA (3.81 mL, 21.9 mmol) and 1-hydroxy-7-azabenzotriazole (1.12 g, 8.22 mmol) were dissolved in 1600 mL of DMF, and into the obtained mixture, the liquid A and the liquid B were simultaneously added dropwise at a low speed of 1.2 mL/h by using a syringe pump, and after completion of the dropwise addition, the resultant mixture was stirred for 24 hours. The residue obtained by distilling off the solvent under reduced pressure was washed with ethyl acetate and hexane to obtain a compound (a7) (1.57 g, 2.96 mmol, yield: 54.2%) as white crystals.

$^1$H NMR (CD$_3$OD): δ 1.46 [9H, s, Boc], 2.82-2.89 [1H, m, CH$_2$], 2.91-2.96 [2H, m, CH$_2$], 3.03-3.14 [1H, m, CH$_2$], 3.56-3.64 [2H, m, CH$_2$], 3.82-4.02 [3H, m, CH$_2$], 4.10-4.18 [1H, m, CH$_2$], 4.46-4.50 [1H, dd, CH], 7.02-7.04 [2H, d, CH], 7.60-7.62 [2H, d, CH].

ESI-MS (M+Na)$^+$: m/z 553.09. found 553.10.

Synthesis Example L1(e): Compound (a8)

A compound (a7) (1.57 g, 2.96 mmol) was suspended in 40 mL of 4 N hydrochloric acid/ethyl acetate, and the obtained suspension was stirred at room temperature for four hours. The crystals obtained by distilling off the solvent under reduced pressure were washed with hexane and dried under reduced pressure to obtain a compound (a8) (1.36 g, 2.92 mmol, yield: 98.4%) as white crystals.

$^1$H NMR (CDCl$_3$): δ 2.83-2.89 [1H, m, CH$_2$], 2.96 [1H, s, CH$_2$], 3.12-3.19 [1H, m, CH$_2$], 3.40-3.52 [2H, m, CH$_2$], 3.62-3.59 [2H, m, CH$_2$], 4.07-4.13 [1H, m, CH$_2$], 4.19-4.42 [1H, m, CH$_2$], 4.60-4.62 [1H, dd, CH], 6.11 [1H, s, NH], 6.54 [1H, s, NH], 6.96-7.01 [2H, d, CH], 7.58-7.60 [2H, d, CH].

ESI-MS (M+H)$^+$: m/z 431.06. found 431.03.

Synthesis Example L1(f): Compound (a9)

A compound (a8) (880 mg, 2.04 mmol) was suspended in 13.5 mL of DMF, and into the obtained suspension, potassium carbonate (424 mg, 3.06 mmol) was further added and suspended. The obtained suspension was ice-cooled, and into the ice-cooled suspension, iodoethane (327 μL, 4.08 mmol) was added dropwise under an argon atmosphere. After completion of the dropwise addition, the obtained mixture was stirred at 80° C. for four days. The residue obtained by distilling off the solvent under reduced pressure was suspended in ethyl acetate, and the obtained suspension was filtered. The filtrate was washed with a 5% by mass sodium hydrogen carbonate aqueous solution. The organic layer was dried with the addition of sodium sulfate, and then the residue obtained by distilling off the solvent under reduced pressure was purified by a flash chromatography system using chloroform and methanol to obtain a compound (a9) (340 mg, 0.742 mmol, yield: 36.3%) as white crystals.

$^1$H NMR (CDCl$_3$): δ 1.10 [3H, t, CH$_3$], 2.76-2.84 [2H, q, CH$_2$], 2.85-2.89 [1H, m, CH$_2$], 3.08-3.25 [6H, m, CH$_2$], 3.37-3.43 [1H, m, CH$_2$], 3.53-3.57 [1H, m, CH$_2$], 3.69-3.75 [1H, m, CH$_2$], 4.61-4.66 [1H, dd, CH], 6.59 [1H, s, NH], 6.84 [1H, s, NH], 6.97-6.99 [2H, d, CH], 7.16 [1H, s, NH], 7.58-7.60 [2H, d, CH].

ESI-MS (M+H)$^+$: m/z 459.09. found 459.17.

Synthesis Example L1(g): Compound (a10)

A compound (a9) (340 mg, 0.742 mmol) was suspended in 1.4 mL of THF, the obtained suspension was ice-cooled, and then into the ice-cooled suspension, 13.5 mL of 0.95 M borane-THF complex/THF solution was slowly added under an argon atmosphere, the obtained mixture was stirred for one hour, and then the resultant mixture was refluxed for 24 hours. The obtained mixture was ice-cooled, and into the ice-cooled mixture, 13.5 mL of methanol was added, and then the obtained mixture was stirred for one hour, and the solvent was distilled off under reduced pressure. After that, 13.5 mL of methanol was added again into the residue, and the solvent was distilled off under reduced pressure. Into the residue, 13.5 mL of concentrated hydrochloric acid was added, the obtained mixture was stirred at room temperature for 24 hours, and then the resultant mixture was refluxed for one hour. The obtained mixture was ice-cooled, and into the ice-cooled mixture, a 2.5N sodium hydroxide aqueous solution was added to make the mixture basic, and then the extraction was performed with chloroform. The organic layer was dried with the addition of sodium sulfate, and then the residue obtained by distilling off the solvent under reduced pressure was purified by a flash chromatography system using a solution of chloroform:methanol:25% by mass ammonia water (10:1:0.1) as an elution solvent to obtain a compound (a10) (163 mg, 0.391 mmol, yield: 52.7%) as a yellow oil.

Synthesis Example L1(h): Compound (a11)

A compound (a10) (197 mg, 0.401 mmol) was dissolved in a mixture of 2.75 mL of acetonitrile and 0.55 mL of DMF, and into the obtained mixture, potassium carbonate (229 mg, 1.65 mmol) was further added and suspended. The obtained suspension was ice-cooled, and into the ice-cooled suspension, tert-butyl bromoacetate (229 μL, 1.40 mmol) was added dropwise under an argon atmosphere. After completion of the dropwise addition, the obtained suspension was stirred at room temperature for 48 hours, the suspension was filtered, and then the solvent was distilled off from the filtrate under reduced pressure. The residue was dissolved in a small amount of chloroform, the obtained solution was applied to TLC for fractionation having a thickness of 1 mm, and purified using a solution of chloroform:methanol=8:1 as a developing solvent to obtain a compound (a11) (306 mg, 0.403 mmol, 100%) as a reddish brown oil.

$^1$H NMR (CDCl$_3$): δ 0.98-1.03 [3H, t, CH$_3$], 1.41-1.48 [27H, m, $^t$Bu], 1.90-4.90 [27H, m, CH$_2$, DOTA], 6.89-7.07 [2H, m, CH], 7.50-7.61 [2H, m, CH].

ESI-MS (M+H)$^+$: m/z 759.36. found 759.24.

Synthesis Example L1(i): Compound (a12)

A compound (a11) (306 mg, 0.403 mmol) was suspended in 2.8 mL of DMF, and into the obtained suspension, Pd(OAc)$_2$ (9.1 mg, 0.0403 mmol), 1,2-bis(diphenylphosphino)ethane (24.12 mg, 0.0604 mmol), Et$_3$N (168 μL, 1.21 mmol), and benzyl alcohol (840 μL, 8.06 mmol) were added, and the obtained mixture was refluxed for 24 hours under an atmosphere of carbon monoxide. After the reaction, the solvent was distilled off under reduced pressure, the residue was dissolved in ethyl acetate, and then the obtained mixture was filtered, and the filtrate was washed with a 5% by mass sodium hydrogen carbonate aqueous solution. The organic layer was dried with the addition of sodium sulfate, and then the residue obtained by distilling off the solvent under reduced pressure was purified by a flash chromatography system using chloroform and methanol to obtain a compound (a12) (113 mg, 0.166 mmol, yield: 41.4%) as a yellow oil.

ESI-MS (M+H)$^+$: m/z 767.50. found 767.60.

Synthesis Example L1 (j): Compound (a13)

A compound (a12) (46 mg, 0.0600 mmol) was dissolved in 1 mL of methanol, and then into the obtained mixture, 100 mg of 10% by mass Pd/C was added, and the obtained mixture was stirred at room temperature for 2 hours under an atmosphere of hydrogen. The reaction mixture was filtered, and then the solvent was distilled off under reduced pressure to obtain a compound (a13) (25.5 mg, 0.0377 mmol, yield: 62.8%) as a yellow oil.

ESI-MS (M+H)$^+$: m/z 677.45. found 677.62.

Synthesis Example L2: Synthesis of CDO3AEt-FGK (Compound (a16)), the Same as the Compound 1-1 Described Above), CDO3AEt-FGK-Boc (Compound (a17)), and CDO3AEt-FGK(Mal) (Compound (a18), the Same as the Compound 1-2 Described Above)
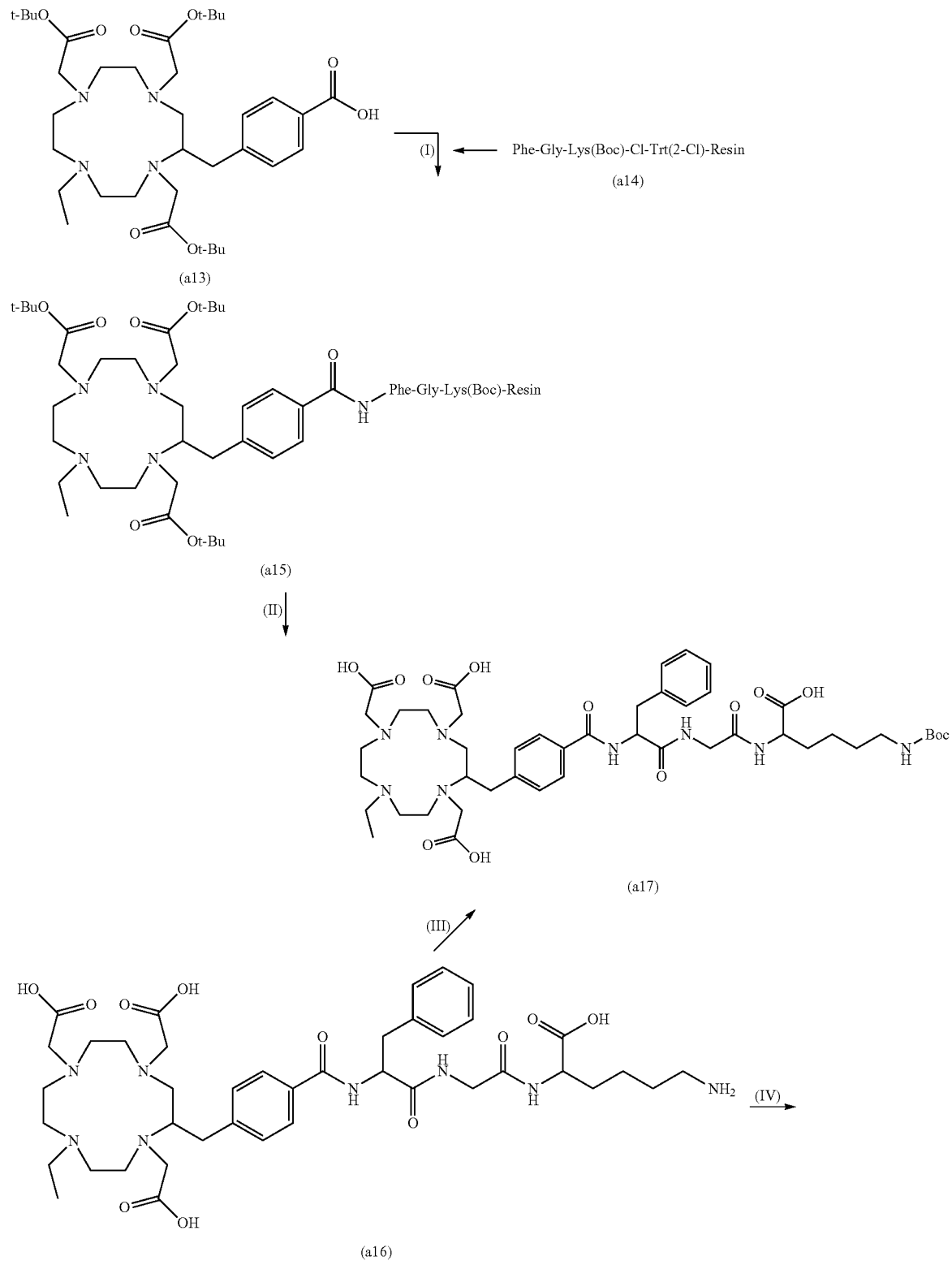

-continued

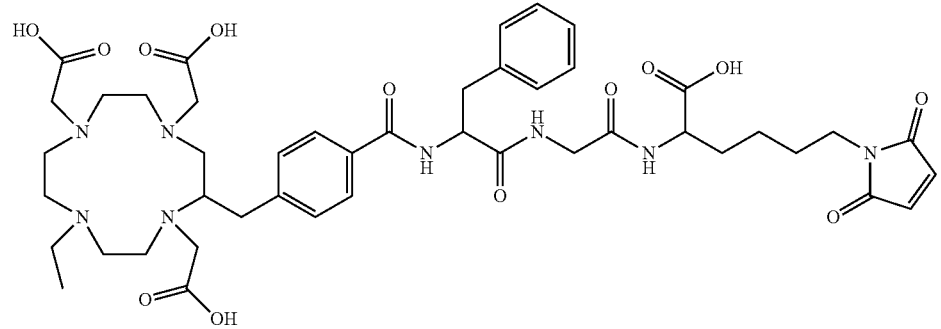

(a18)

(I) DIC, HOAt, DMF; TFA:TIS:MQ = 95:2.5:2.5, 2 hr, (II) (Boc)$_2$O dioxane, sat NaHCO$_3$; (III) sat NaHCO$_3$ aq, (Boc)$_2$O, dioxane, 2 hr (IV) N-methoxycarbonylmaleimide, sat NaHCO$_3$ aq

Synthesis Examples L2(I) and L2(II): Compound (a16)

A peptide-extended resin (a14) (22 μmol) obtained by using a Fmoc solid phase synthesis method, 1-hydroxy-7-azabenzotriazole (15.1 mg, 110 μmol), a compound (a13) (15 mg, 22 μmol) were dissolved in DMF, into the obtained mixture, N,N'-diisopropylcarbodiimide (17.2 μL, 110 μmol) was added, and the resultant mixture was stirred gently at room temperature for 16 hours. After completion of the reaction, the resin was washed with DMF and CH$_2$Cl$_2$.

The obtained resin (a15) was suspended in a solution with a composition of trifluoroacetic acid:triisopropylsilane:water=95:2.5:2.5, and the obtained suspension was stirred gently for 2 hours. After completion of the reaction, the resin was removed by filtration, and the filtrate was distilled off under reduced pressure to obtain white crystals. In addition, by a linear gradient method in which HPLC using Imtakt Cadenza 5CD-C18 150×20 mm was used, 0.1% TFA/MilliQ for phase A and 0.1% TFA/MeCN for phase B were used as the mobile phases, and the phases were changed from phase A 95% and phase B 5% to phase A 70% and phase B 30% in the period of 0 to 35 minutes, and changed from the phase A 70% and the phase B 30% to phase A 0% and phase B 100% in the period of 35 to 40 minutes, the purification was performed at a flow rate of 5 mL/min, and a desired compound (a16) (hereinafter, also referred to as "CDO3AEt-FGK", 5.7 mg, 6.78 μmol, yield: 30.8%) was obtained.

ESI-MS (M−H)$^-$: m/z 839.4, found: 839.3

Synthesis Example L2(III): Compound (a17)

A compound (a16) was dissolved in 100 μL of saturated aqueous solution of sodium hydrogen carbonate, into the obtained mixture, 100 μL of dioxane in which 1.5 equivalents of (Boc)$_2$O had been dissolved was added, and the resultant mixture was stirred vigorously at room temperature for 2 hours. The dioxane was removed by the distillation under reduced pressure, and then the water layer was washed with chloroform. In addition, for the water layer, by a linear gradient method in which HPLC using Imtakt Cadenza 5CD-C18 150×20 mm was used, 0.1% TFA/MilliQ for phase A and 0.1% TFA/MeCN for phase B were used as the mobile phases, the phase A was kept 100% in the period of up to 2 minutes, and then the phases were changed from the phase A 100% and phase B 0% to phase A 95% and phase B 5% in the period of 2 to 5 minutes, changed from the phase A 95% and the phase B 5% to phase A 70% and phase B 30% in the period of 5 to 40 minutes, and changed from the phase A 70% and the phase B 30% to phase A 0% and phase B 100% in the period of 40 to 45 minutes, the purification was performed at a flow rate of 5 mL/min, and a desired compound (a17) (hereinafter, also referred to as "CDO3AEt-FGK-Boc") was obtained.

ESI-MS (M−H)$^-$: m/z 939.5, found: 940.49.

Synthesis Example L2(IV): Compound (a18) CDO3AEt-FGK(Mal)

A compound (a16) (2.2 mg, 2.6 μmol) was dissolved in 200 μL of saturated aqueous solution of sodium hydrogen carbonate, into the obtained mixture, N-methoxycarbonylmaleimide (0.8 mg, 5.2 μmol) was added under ice cooling, and the resultant mixture was stirred for 2 hours under ice cooling. After completion of the reaction, the obtained mixture was adjusted to be acidic with a 10% by mass citric acid aqueous solution. In addition, by a linear gradient method in which HPLC using Imtakt Cadenza 5CD-C18 150×20 mm was used, 0.1% TFA/MilliQ for phase A and 0.1% TFA/MeCN for phase B were used as the mobile phases, the phase A was kept 100% in the period of up to 5 minutes, and then the phases were changed from the phase A 100% and phase B 0% to phase A 55% and phase B 45% in the period of 5 to 35 minutes, and changed from the phase A 55% and the phase B 45% to phase A 0% and phase B 100% in the period of 35 to 50 minutes, the purification was performed at a flow rate of 5 mL/min, and a desired compound (a18) (hereinafter, also referred to as "CDO3AEt-FGK(Mal)", 0.8 mg, 0.870 μmol, yield: 33.4%) was obtained.

ESI-MS (M−H)$^-$: m/z 919.42, found: 919.45.

Synthesis of DO3A-Bn-SCN-MVK(Bzo) and DO3A-Bn-SCN-Met-OH, and DO3A-Bn-SCN-MVK (Mal)

Synthesis Example L3: Synthesis of Compound (b5) and Compound (b7)

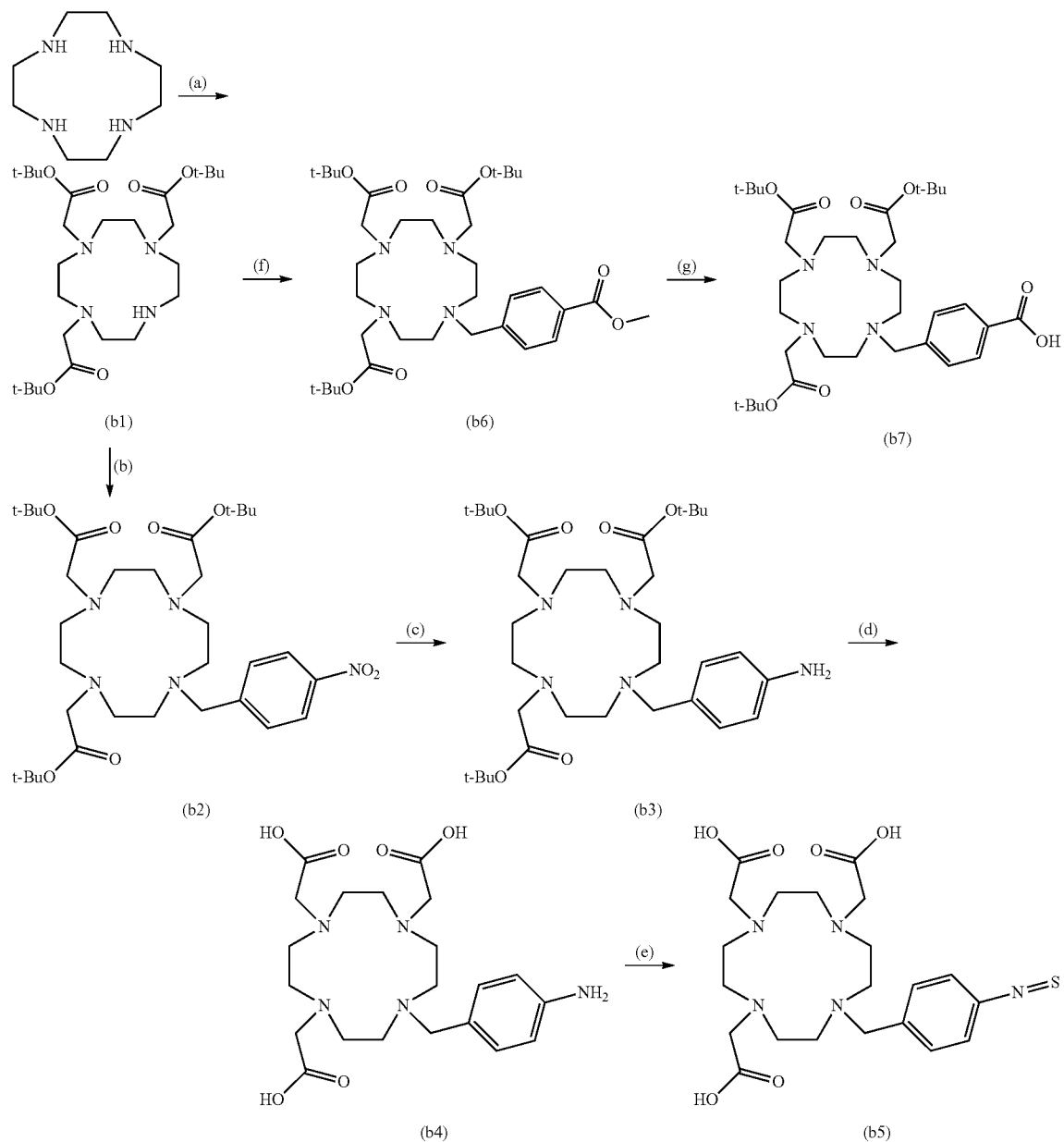

(a) tert-butyl bromoacetate, NaHCO₃, acetonitrile, 43.1%; (b) 4-nitrobenzyl bromide, Na₂CO₃, acetonitrile, 98.0%; (c) 10% Pd/C, methanol, 1N NaOH, 87.2%; (d) 10% anisole/TFA 64.9%; (e) 1M thiophosgene/chloroform, 74.9%

Synthesis Example L3(a): Synthesis of Compound (b1)

Cyclen (523.6 mg, 3.04 mmol) was dissolved in acetonitrile (25 mL), and into the obtained mixture, NaHCO₃ (893.6 mg, 10.6 mmol) was added, the resultant mixture was ice-cooled under an Ar atmosphere, and then into the ice-cooled mixture, tert-butyl bromoacetate (1.39 mL, 3.34 mmol) was added dropwise. The resultant mixture was stirred at room temperature for 48 hours, and then the reaction mixture was filtered, and the filtrate was distilled off under reduced pressure. The residue was purified by recrystallization using toluene to obtain a compound (b1) (672.4 mg, yield: 43.1%) as white crystals.

$^1$H NMR (CDCl$_3$): δ 1.44 (27H, s, tBu), 2.86-3.35 (22H, overlapped, CH$_2$)

ESI-MS (M+H)$^+$: m/z 515.3, found: 515.3.

Synthesis Example L3(b): Synthesis of Compound (b2)

A compound (b1) (212.9 mg, 413.6 μmol) was dissolved in acetonitrile (4.0 mL), and into the obtained mixture, $Na_2CO_3$ (87.7 mg, 827.4 μmol) was added, the resultant mixture was ice-cooled under an Ar atmosphere, and then into the ice-cooled mixture, 4-nitrobenzyl bromide (134.1 mg, 620.7 μmol) dissolved in acetonitrile (1.0 mL) was added dropwise. The resultant mixture was stirred at 60° C. for 18 hours, and then the reaction mixture was filtered, and the solvent was distilled off under reduced pressure. The residue was purified by silica gel chromatography using a solution of chloroform:methanol=10:1 as an elution solvent to obtain a compound (b2) (263.4 mg, yield: 98.0%) as a yellow oily substance.

$^1$H NMR (CDCl$_3$): δ 1.36 (27H, s, tBu), 2.06-3.58 (24H, overlapped, CH$_2$), 7.61-7.63 (2H, d, aromatic), 8.07-8.09 (2H, d, aromatic).

ESI-MS (M+Na)$^+$: m/z 672.4, found: 672.3.

Synthesis Example L3(c): Synthesis of Compound (b3)

A compound (b2) (150 mg, 231 μmol) was dissolved in methanol (3.5 mL), and then into the mixture, 1 N NaOH (0.5 mL), and 10% Pd/C (15.4 mg) were added. The obtained mixture was stirred at room temperature for 1.5 hours under an atmosphere of hydrogen. The resultant mixture was filtered, and then the methanol was distilled off from the filtrate under reduced pressure, and the extraction was performed with chloroform (5 mL×3). The organic layer was dried with the addition of $Na_2SO_4$, and then the solvent was distilled off under reduced pressure to obtain a compound (b3) (124.6 mg, yield: 87.2%) as a yellow oily substance.

$^1$H NMR (CDCl$_3$): δ 1.43 (27H, s, tBu), 2.85-3.35 (24H, overlapped, CH$_2$), 6.59-6.61 (2H, d, aromatic), 6.93-6.95 (2H, d, aromatic).

ESI-MS (M+H)$^+$: m/z 620.4, found: 620.5.

Synthesis Example L3(d): Synthesis of Compound (b4)

A compound (b3) (124.6 mg, 201 μmol) was dissolved in 10% anisole/trifluoroacetic acid (TFA) (2 mL), and the obtained mixture was stirred at room temperature for 4 hours. The solvent was distilled off under reduced pressure, and the residue was crystallized with the addition of diethyl ether (5 mL). The crystals were collected by filtration, washed with diethyl ether, and then dried under reduced pressure to obtain a TFA salt (118.4 mg, yield: 64.9%) of a compound (b4) as reddish brown crystals.

$^1$HNMR (D$_2$O): δ2.50-3.50 (24H, overlapped, CH$_2$), 6.78-6.81 (2H, d, aromatic), 7.36-7.38 (2H, d, aromatic).

Synthesis Example L3(e): Synthesis of Compound (b5)

A compound (b4) (82.5 mg, 80.8 μmol) was dissolved in MilliQ water (1 mL), and into the mixture, 1 M thiophosgene/chloroform (1 mL) was added. The obtained mixture was stirred at room temperature for 2 hours, and then the resultant mixture was washed with chloroform (5 mL×4). The water layer was freeze-dried to obtain a compound (b5) (57.4 mg, yield: 74.9%) as pale yellow crystals.

$^1$HNMR (D$_2$O): δ2.50-3.65 (24H, overlapped, CH$_2$), 7.18-7.22 (2H, d, aromatic), 7.38-7.41 (2H, d, aromatic).

Synthesis Example L3(f): Synthesis of Compound (b6)

A compound (b1) (100.0 mg, 194.4 μmol) was dissolved in acetonitrile (2.0 mL), and into the obtained mixture, $Na_2CO_3$ (26.5 mg, 252.9 μmol) was added, the resultant mixture was ice-cooled under an Ar atmosphere, and then into the ice-cooled mixture, methyl-4-(bromomethyl)benzoate (58.0 mg, 253.0 μmol) dissolved in acetonitrile (0.5 mL) was added dropwise. The obtained mixture was stirred at 60° C. for 18 hours, and then the resultant mixture was filtered, and the solvent was distilled off under reduced pressure. The residue was purified by silica gel chromatography using a solution of chloroform:methanol=10:1 as an elution solvent to obtain a compound (b6) (106.1 mg, yield: 82.6%) as a yellow oily substance.

$^1$H NMR (CDCl$_3$): δ 1.46 (27H, s, tBu), 2.01-3.58 (24H, overlapped, CH$_2$), 3.88 (3H, s, OCH$_3$), 7.53-7.55 (2H, d, aromatic), 7.95-7.97 (2H, d, aromatic).

ESI-MS (M+H)$^+$: m/z 663.4, found: 663.4

Synthesis Example L3(g): Synthesis of Compound (b7)

A compound (b6) (106.1 mg, 160.0 μmol) was dissolved in methanol (1 mL), and then into the obtained mixture, 1 N NaOH (1 mL) was added, and the resultant mixture was stirred at room temperature for 2 hours. The methanol was distilled off from the mixture under reduced pressure, and then the extraction was performed with chloroform (5 mL×3). The organic layer was dried with the addition of $Na_2SO_4$, and then the solvent was distilled off under reduced pressure to obtain a compound (b7) (50.5 mg, yield 48.6%) as a yellow oily substance.

$^1$H NMR (CDCl$_3$): δ 1.44 (27H, s, tBu), 2.13-3.58 (24H, overlapped, CH$_2$), 7.31-7.33 (2H, d, aromatic), 8.09-8.11 (2H, d, aromatic).

ESI-MS (M+Na)$^+$: m/z 671.4, found: 671.5.

Synthesis Example L4: Synthesis of DO3A-Bn-SCN-MVK(Bzo) (Compound (b13)) and DO3A-Bn-SCN-Met-OH (Compound (b14))

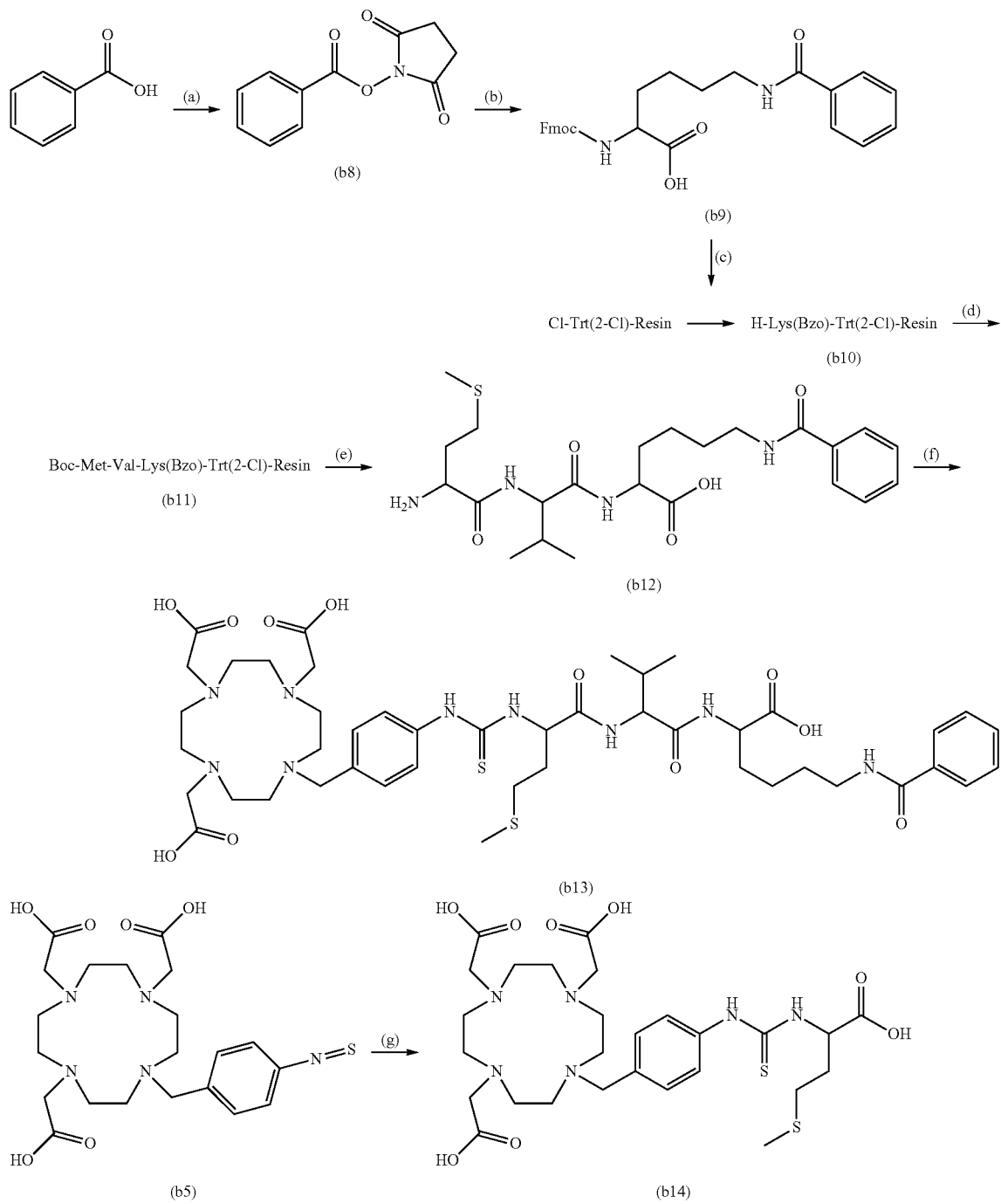

(a) N-hydroxysuccinimide, DCC, dichloromethane, 74.7%; (b) Fmoc-Lys-OH, DIPEA, DMF, 82.0%; (c) i. DIPEA, dichloromithane; ii. methanol, DIPEA; iii. 20% piperidine/DMF; (d) Fmoc solid-phase elongation; (e) TFA:TIS:H$_2$O = 95:2.5:2.5, 69.0%; (f) p-SCN-Bn-DO3A, 0.16M borate buffer pH 11.0, 1N NaOH, 53.3%; (g) methionine, 0.16M borate buffer pH 11.0, 1N NaOH, 36.2%

Synthesis Example L4 (a): Synthesis of Compound (b8)

Benzoic acid (560 mg, 4.59 mmol) and N-hydroxysuccinimide (NHS, 581 mg, 5.05 mmol) were dissolved in CH$_2$Cl$_2$ (15 mL), the obtained mixture was ice-cooled, and then into the ice-cooled mixture, N,N'-dicyclohexylcarbodiimide (DCC, 1.05 g, 5.05 mmol) dissolved in CH$_2$Cl$_2$ (8 mL) was added dropwise. The obtained mixture was stirred at room temperature for 3 hours, and then the resultant mixture was filtered, and the solvent was distilled off under reduced pressure. The residue was dissolved in ethyl acetate (10 mL), and the obtained mixture was washed with sat. NaHCO$_3$ (10 mL×3). The organic layer was dried with the addition of MgSO$_4$, and then the solvent was distilled off under reduced pressure to obtain a compound (b8) (749.7 mg, yield: 74.7%) as white crystals.

$^1$H NMR (CDCl$_3$): δ 2.89 (4H, s, succinimide), 7.47-7.51 (2H, m, aromatic), 7.64-7.68 (1H, m, aromatic), 8.11-8.13 (2H, m, aromatic).

Synthesis Example L4 (b): Synthesis of Compound (b9)

Fmoc-Lys-OH (86.7 mg, 100 μmol) was dissolved in DMF (1.5 mL), and into the obtained mixture, N,N-diisopropylethylamine (DIPEA, 40 μL, 246 μmol) was added, the resultant mixture was ice-cooled under an Ar atmosphere, and then into the ice-cooled mixture, a compound (b8) dissolved in DMF (0.5 mL) was added dropwise. The obtained mixture was stirred at room temperature for 3 hours, and then the solvent was distilled off under reduced pressure. The residue was dissolved in ethyl acetate (5 mL), and the obtained solution was washed with 10% by mass citric acid (5 mL×3). The organic layer was dried with the addition of Na$_2$SO$_4$, and then the solvent was distilled off under reduced pressure, and the residue was purified by TLC fractionation using a solution of chloroform:methanol=5:1 as a developing solvent to obtain a compound (b9) (82.0 mg, yield: 82.0%) as white crystals.

ESI-MS (M+Na)$^+$: m/z 473.2, found: 473.2

Synthesis Example L4(c): Synthesis of Compound (b10)

By using Cl-Trt (2-Cl) Resin (62.5 mg, 100 μmol, available from WATANABE CHEMICAL INDUSTRIES, LTD.) as a starting material, Fmoc-Lys (Bzo)-OH (47.2 mg, 100 mol) and DIPEA (65 μL, 400 μmol) were reacted in dichloromethane (1.5 mL) for 1.5 hours. Into the reaction mixture, methanol (1.5 mL) and DIPEA (65 μL) were added to terminate the reaction. The resin was washed with DMF, and then with dichloromethane. The obtained resin was dried, and then by measuring the absorbance at A301 of N-(9-fluorenylmethyl)piperidine formed during piperidine treatment, the amount of Fmoc-Lys(Bzo)-OH introduced into the resin was quantified (0.96 mmol/g). Into the mixture, 20% piperidine/DMF (mL) was added, and the obtained mixture was stirred at room temperature for 20 minutes to prepare a compound (b10). Part of the resin was collected, and subjected to a Kaiser test to confirm the deprotection of Nα-Fmoc group.

Synthesis Example L4(d): Synthesis of Compound (b11)

By using a compound (b10) (22.9 mg, 22.0 μmol) as a starting material, 2.5 equivalents of Fmoc-Met-OH (55.0 μmol) by a Fmoc solid phase synthesis method, N,N'-diisopropylcarbodiimide (DIC, 8.5 μL, 55.0 μmol), and 1-hydroxybenzotriazolemonohydrate (HOBt, 8.43 mg, 55.0 μmol) were stirred in DMF at room temperature for 2 hours. Part of the resin was collected, and subjected to a Kaiser test to confirm the completion of condensation reaction, and then into the obtained mixture, 20% piperidine/DMF (2 mL) was added, and the resultant mixture was stirred at room temperature for 20 minutes. Part of the resin was collected, and subjected to a Kaiser test to confirm the deprotection of the Nα-Fmoc group. In addition, similar operation was performed by using a protected amino acid Boc-Met-OH, and a compound (b11) was prepared.

Synthesis Example L4(e): Synthesis of Compound (b12)

A compound (b11) was stirred at room temperature for 2 hours in a mixture of TFA:triisopropylsilane (TIS):H$_2$O=95:2.5:2.5 (1 mL). The resin was filtered off, and then into the residue obtained by distilling off the filtrate under reduced pressure, diethyl ether was added for the recrystallization. The crystals were collected by filtration, washed with diethyl ether, and then dried under reduced pressure to obtain a TFA salt (9.7 mg, yield: 69.0%) of a compound (b12) as white crystals.

ESI-MS (M+H)$^+$: m/z 481.2, found: 481.2.

Synthesis Example L4(f): Synthesis of Compound (b13)

A compound (b5) (1.0 mg, 1.05 μmol) and a compound (b12) (1.58 μmol) were dissolved in a 0.16 M borate buffer solution at pH 11.0 (100 μL), and then the obtained mixture was adjusted to be pH 9.0 with 1 N NaOH. The resultant mixture was stirred at room temperature for 2 hours, and then the mixture was purified by RP-HPLC for fractionation to obtain a TFA salt (0.8 mg, yield 53.3%) of a compound (b13) (hereinafter, also referred to as "DO3A-Bn-SCN-MVK(Bzo)") as white crystals.

ESI-MS (M+H)$^+$: m/z 974.4, found: 974.4.

Synthesis Example L4(g): Synthesis of Compound (b14)

By using a compound (b5) (5.5 mg, 5.78 μmol) and methionine (1.29 mg, 8.67 μmol) as starting materials, similar operation as in Synthesis Example L4 (f) was performed, and a TFA salt (2.3 mg, yield: 36.2%) of a compound (b14) (hereinafter, also referred to as "DO3A-Bn-SCN-Met-OH") was obtained as white crystals. ESI-MS (M+H)$^+$: m/z 643.2, found: 643.2

Synthesis Example L5: Synthesis of DO3A-Bn-SCN-MVK(Mal) (Compound (b21))

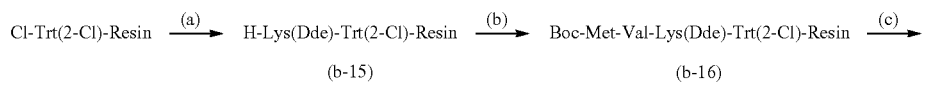

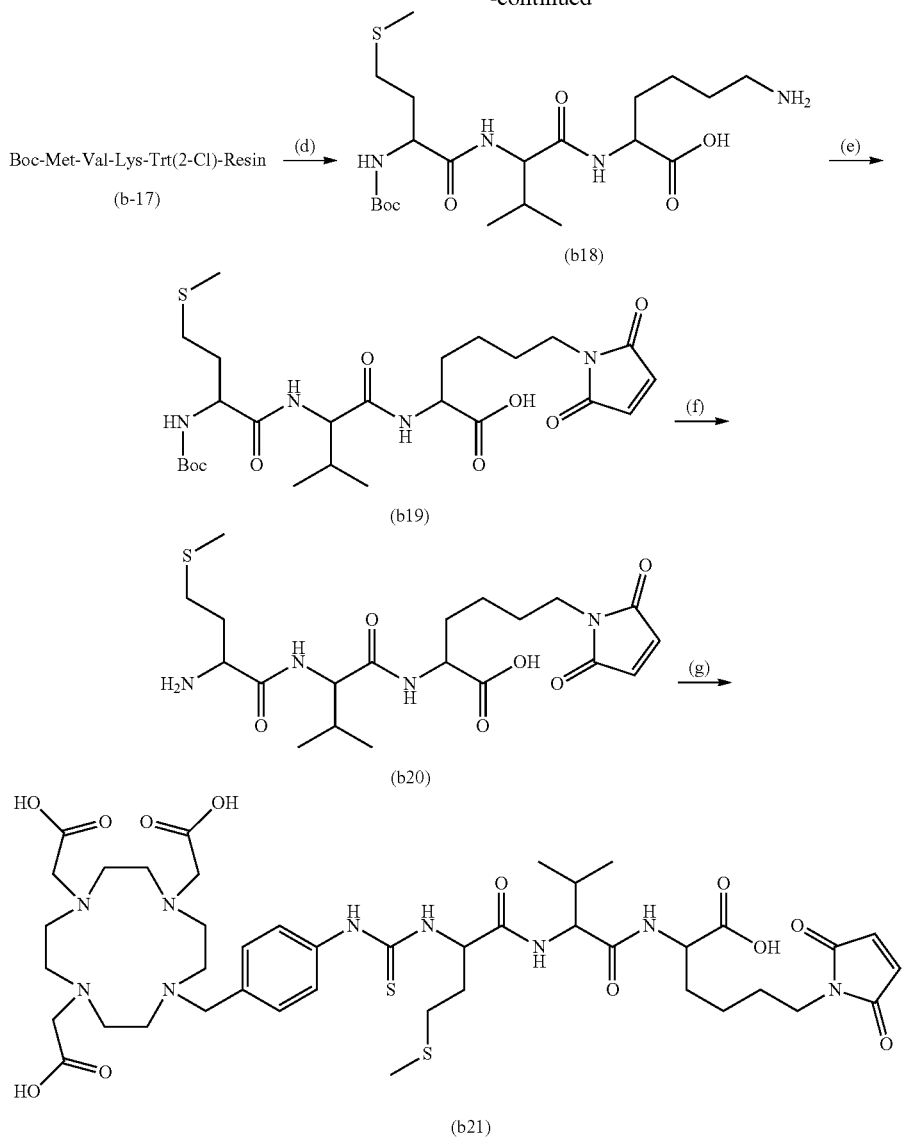

(a) i. Fmoc-Lys(Dde)-OH, DIPEA, dichloromithane; ii. methanol, DIPEA; iii. 20% piperidine/DMF; (b) Fmoc solid-phase elongation; (c) 2% hydrazine/DMF; (d) aceti acid:TFE:CH$_2$Cl$_2$ = 3:1:6, 93.9%; (e) NMCM, sat. NaHCO$_3$, 94.1%; (f) 4M HCl/AcOEt, 92.4%; (g) p-SCN-Bn-DO3a, TEA, DMF, 33.2%

Synthesis Example L5(a): Synthesis of Compound (b15)

By using Cl-Trt(2-Cl) Resin (104.4 mg, 114.8 μmol, available from WATANABE CHEMICAL INDUSTRIES, LTD.) as a starting material, Fmoc-Lys(Dde)-OH (61.2 mg, 114.8 μmol) and DIPEA (81 μL, 459.2 μmol) were reacted in dichloromethane (2 mL) for 1.5 hours. Into the reaction mixture, methanol and DIPEA were added to terminate the reaction. The resin was washed with DMF, and then with dichloromethane. In a similar manner to Synthesis Example L4 (c), the amount of Fmoc-Lys (Bzo)-OH introduced into the resin was quantified (0.769 mmol/g). Into the mixture, 20% piperidine/DMF (2 mL) was added, and the obtained mixture was stirred at room temperature for 20 minutes to prepare a compound (b15). Part of the resin was collected, and subjected to a Kaiser test to confirm the deprotection of Na-Fmoc group.

Synthesis Example L5(b): Synthesis of Compound (b16)

By using a compound (b15) (153.4 mg, 114.8 μmol) as a starting material, operation similar to that in Synthesis Example L4 (d) was performed by changing the protected amino acid to Fmoc-Val-OH and to Boc-Met-OH in order, and a compound (b16) was obtained.

Synthesis Example L5(c): Synthesis of Compound (b17)

A compound (b16) (117.9 μmol) was stirred at room temperature for one hour in 2% hydrazine/DMF (2 mL), and then part of the resin was collected, and subjected to a Kaiser test to confirm the completion of reaction. The resin was washed with DMF and then with dichloromethane, and subsequently dried under reduced pressure to obtain a compound (b17).

Synthesis Example L5(d): Synthesis of Compound (b18)

A compound (b17) was stirred at room temperature for 2 hours in a mixture of acetic acid:2,2,2-trifluoroethanol (TFE):dichloromethane=3:1:6 (2 mL). The resin was filtered off, and then the residue obtained by distilling off the filtrate under reduced pressure was crystallized with the addition of diethyl ether. The crystals were collected by filtration, washed with diethyl ether, and then dried under reduced pressure to obtain an acetate (51.4 mg, yield: 93.9%) of a compound (b18) as white crystals.

ESI-MS $(M+H)^+$: m/z 477.2, found: 477.2.

Synthesis Example L5(e): Synthesis of Compound (b19)

A compound (b18) (6.60 mg, 13.9 μmol) was dissolved in sat. $NaHCO_3$ (100 μL) by ice cooling, and into the obtained mixture, N-methoxycarbonylmaleimide (NMCM, 3.22 mg, 20.8 μmol) was added. The obtained mixture was stirred for 2 hours under ice cooling, and then the resultant mixture was neutralized with the addition of 5% by mass citric acid, and the extraction was performed with chloroform (5 mL×3). The extract was dried with the addition of $Na_2SO_4$, and then the solvent was distilled off under reduced pressure to obtain a compound (b19) (7.26 mg, yield: 94.1%) as white crystals.

ESI-MS $(M+H)^+$: m/z 557.2, found: 557.2.

Synthesis Example L5(f): Synthesis of Compound (b20)

A compound (b19) (7.26 mg, 13.1 μmol) was dissolved in 4 M HCl/ethyl acetate (1 mL), the obtained mixture was stirred at room temperature for one hour. The solvent was distilled off under reduced pressure, and the residue was azeotropic with hexane to obtain a hydrochloride (5.92 mg, yield: 92.4%) of a compound (b20) as white crystals.

ESI-MS $(M+H)^+$: m/z 457.2, found: 457.2.

Synthesis Example L5(g): Synthesis of Compound (b21)

A hydrochloride (3.38 mg, 4.74 μmol) of a compound (b20) was dissolved in DMF (100 μL), and into the obtained mixture, triethylamine (TEA, 6 μL, 43.3 μmol) was added. Into the mixture, a compound (b5) (3.0 mg, 3.16 μmol) was added, and the obtained mixture was stirred at room temperature for 2 hours, and then the resultant mixture was diluted 10 times with $H_2O$, and the diluted mixture was purified by RP-HPLC for fractionation to obtain a TFA salt (1.5 mg, yield: 33.2%) of a compound (b21) (hereinafter, also referred to as "DO3A-Bn-SCN-MVK(Mal)") as white crystals.

ESI-MS $(M+H)^+$: m/z 972.5, found: 972.5.

Synthesis of DO3A-Bn-CO-FGK, DO3A-Bn-CO-FGK(Boc), DO3A-Bn-CO-FGK(Mal), and DO3A-Bn-CO-Phe-OH

Synthesis Example L6: Synthesis of DO3A-Bn-CO-FGK (Compound (b24), the Same as the Compound 1-3 Described Above), DO3A-Bn-CO-FGK (Boc) (Compound (b25)), DO3A-Bn-CO-FGK(Mal) (Compound (b26), the Same as the Compound 1-4 Described Above), and DO3A-Bn-CO-Phe-OH (Compound (b28))

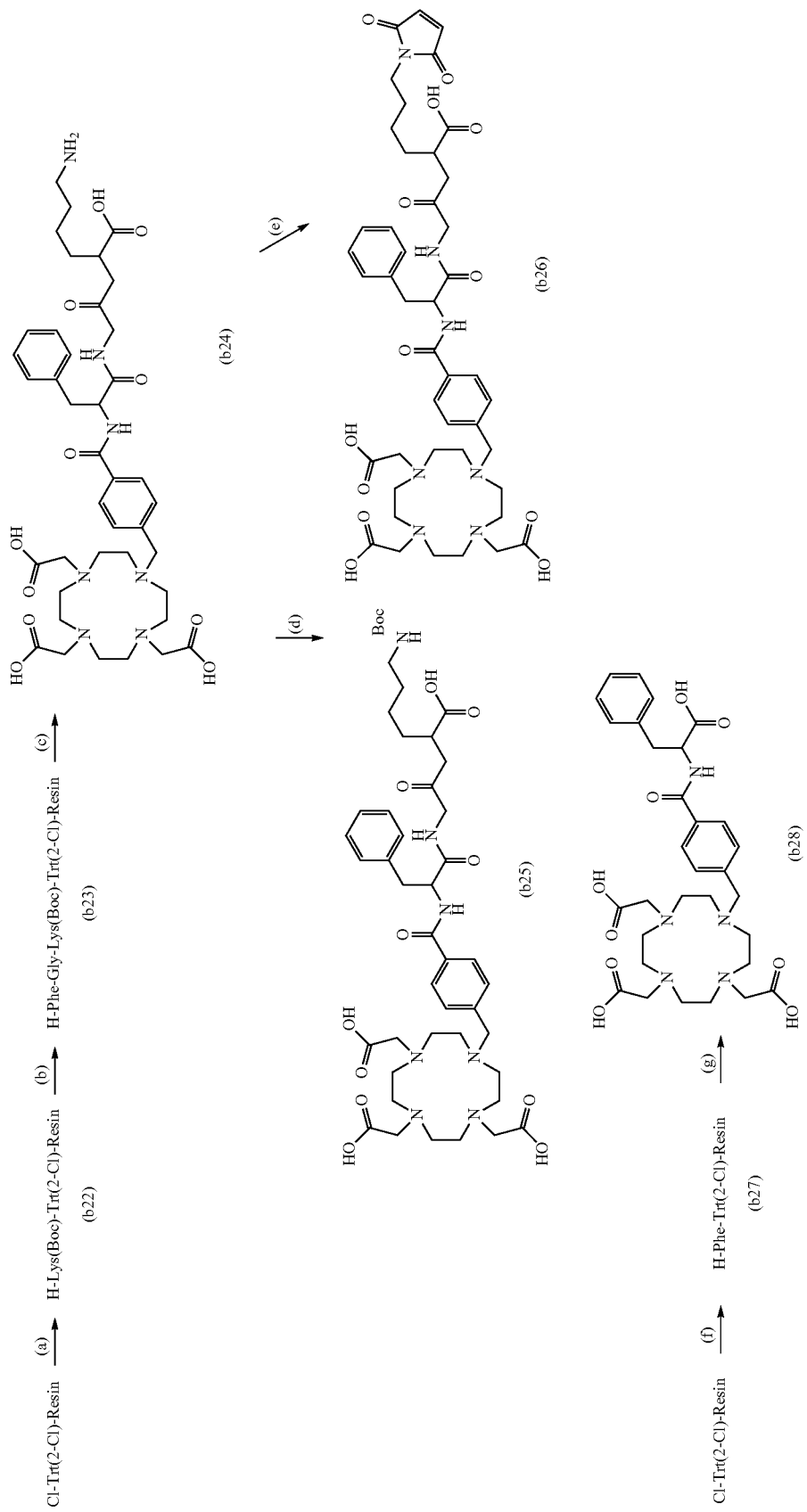
(a) i. Fmoc-Lys(Boc)-OH, DIPEA, dichloromethane; ii. methanol, DIPEA; iii. 20% piperidine/DMF; (b) Fmoc solid-phase elongation; (c) i. p-COOH-Bn-DO3A, DIC, HOAt, DMF; ii. TFA:TIS:H₂O = 95:2.5:2.5, 53.7%; (d) (Boc)₂O, sat. NaHCO₃, 26.9%; (e) NMCM, sat. NaHCO₃, 44.4%; (f) i. Fmoc-Phe-OH, DIPEA, dichloromethane; ii. methanol, DIPEA; iii. 20% piperidine/DMF;(g) i. p-COOH-Bn-DO3A, DIC, HOAt, DMF; ii. TFA:TIS:H₂O = 95:2.5:2.5, 59.1%

Synthesis Example L6(a): Synthesis of Compound (b22)

By using Cl-Trt (2-Cl) Resin (22.1 mg, 24.3 µmol, available from WATANABE CHEMICAL INDUSTRIES, LTD.) as a starting material, Fmoc-Lys(Boc)-OH (17.1 mg, 36.5 µmol) and DIPEA (16.5 µL, 97.2 µmol) were reacted in dichloromethane (1 mL) for 1.5 hours. Into the reaction mixture, methanol and DIPEA were added to terminate the reaction. The resin was washed with DMF, and then with dichloromethane. In a similar manner to Synthesis Example L4 (c), the amount of Fmoc-Lys(Boc)-OH introduced into the resin was quantified (0.884 mmol/g). Into the mixture, 20% piperidine/DMF (2 mL) was added, and the obtained mixture was stirred at room temperature for 20 minutes to prepare a compound (b22). Part of the resin was collected, and subjected to a Kaiser test to confirm the deprotection of Na-Fmoc group.

Synthesis Example L6(b): Synthesis of Compound (b23)

By using a compound (b22) (12.1 µmol) as a starting material, operation similar to that in Synthesis Example L4 (d) was performed by changing the protected amino acid to Fmoc-Gly-OH and to Fmoc-Phe-OH in order, and a compound (b23) was obtained.

Synthesis Example L6(c): Synthesis of Compound (b24)

Into a compound (b23) (12.1 µmol), a compound (b7) (15.7 mg, 24.2 µmol), DIC (3.7 µL, 24.2 µmol), and HOAt (3.29 mg, 24.2 µmol) were added and stirred in DMF at room temperature overnight. Part of the resin was collected, and subjected to a Kaiser test to confirm the completion of condensation reaction, and then the resultant mixture was stirred at room temperature for 2 hours in a mixture of TFA:TIS:$H_2O$=95:2.5:2.5 (1 mL). The resin was filtered off, and then the residue obtained by distilling off the filtrate under reduced pressure was crystallized with the addition of diethyl ether. The crystals were collected by filtration, washed with diethyl ether, and then dried under reduced pressure to obtain a TFA salt (9.0 mg, yield: 53.7%) of a compound (b24) (hereinafter, also referred to as "DO3A-Bn-CO-FGK") as white crystals.

ESI-MS (M+H)$^+$: m/z 813.4, found: 813.4.

Synthesis Example L6(d): Synthesis of Compound (b25)

A compound (b24) (2.17 µmol) was dissolved in sat. $NaHCO_3$ (100 µL), and then into the obtained mixture, (Boc)$_2$O (7.1 mg, 3.26 µmol) dissolved in dioxane (100 µL) was added, and the resultant mixture was stirred vigorously at room temperature for 2 hours. The dioxane was distilled off under reduced pressure, and then the residue was washed with chloroform (3 mL×3). The water layer was purified by RP-HPLC for fractionation to obtain a TFA salt (0.8 mg, yield: 26.9%) of a compound (b25) (hereinafter, also referred to as "DO3A-Bn-CO-FGK(Boc)") as white crystals. ESI-MS (M+H)$^+$: m/z 913.5, found: 913.5.

Synthesis Example L6(e): Synthesis of Compound (b26)

A compound (b24) (2.17 µmol) was dissolved in sat. $NaHCO_3$ (100 µL), and then the obtained mixture was ice-cooled, and into the ice-cooled mixture, NMCM (0.5 mg, 3.26 µmol) was added. The obtained mixture was stirred for 2 hours under ice cooling, and then the resultant mixture was purified by RP-HPLC for fractionation to obtain a TFA salt (1.3 mg, yield: 44.4%) of a compound (b26) (hereinafter, also referred to as "DO3A-Bn-CO-FGK(mal)") as white crystals.

ESI-MS (M+H)$^+$: m/z 893.4, found: 893.4.

Synthesis Example L6(f): Synthesis of Compound (b27)

By using Cl-Trt(2-Cl) Resin (5 mg, 5.50 µmol, available from WATANABE CHEMICAL INDUSTRIES, LTD.) as a starting material, Fmoc-Phe-OH (6.01 µmol) and DIPEA (3.73 µL, 21.9 µmol) were reacted in dichloromethane (0.5 mL) for 1.5 hours. Into the reaction mixture, methanol and DIPEA were added to terminate the reaction. The resin was washed with DMF, and then with dichloromethane. In a similar manner to Synthesis Example L4 (c), the amount of Fmoc-A.A.-OH introduced into the resin was quantified (0.917 mmol/g). Into the mixture, 20% piperidine/DMF (2 mL) was added, and the obtained mixture was stirred at room temperature for 20 minutes to prepare a compound (b27). Part of the resin was collected, and subjected to a Kaiser test to confirm the deprotection of Na-Fmoc group.

Synthesis Example L6(g): Synthesis of Compound (b28)

By using a compound (b27) (5.5 µmol) as a starting material, similar operation as in Synthesis Example L6(c) was performed, and a TFA salt (4.5 mg, yield: 59.1%) of a compound (b28) (hereinafter, also referred to as "DO3A-Bn-CO-Phe-OH") was obtained as white crystals.

ESI-MS (M+H)$^+$: m/z 628.3, found: 628.3.

Synthesis of CDOTA-Bn-CO-FGK, CDOTA-Bn-CO-FGK(Boc), and Cdota-Bn-Co-Fgk(Mal)

Synthesis Example L7: Synthesis of CDOTA-Bn-CO-FGK (Compound (b29)), CDOTA-Bn-CO-FGK (Boc) (Compound (b30)), and CDOTA-Bn-CO-FGK(Mal) (Compound (b31))

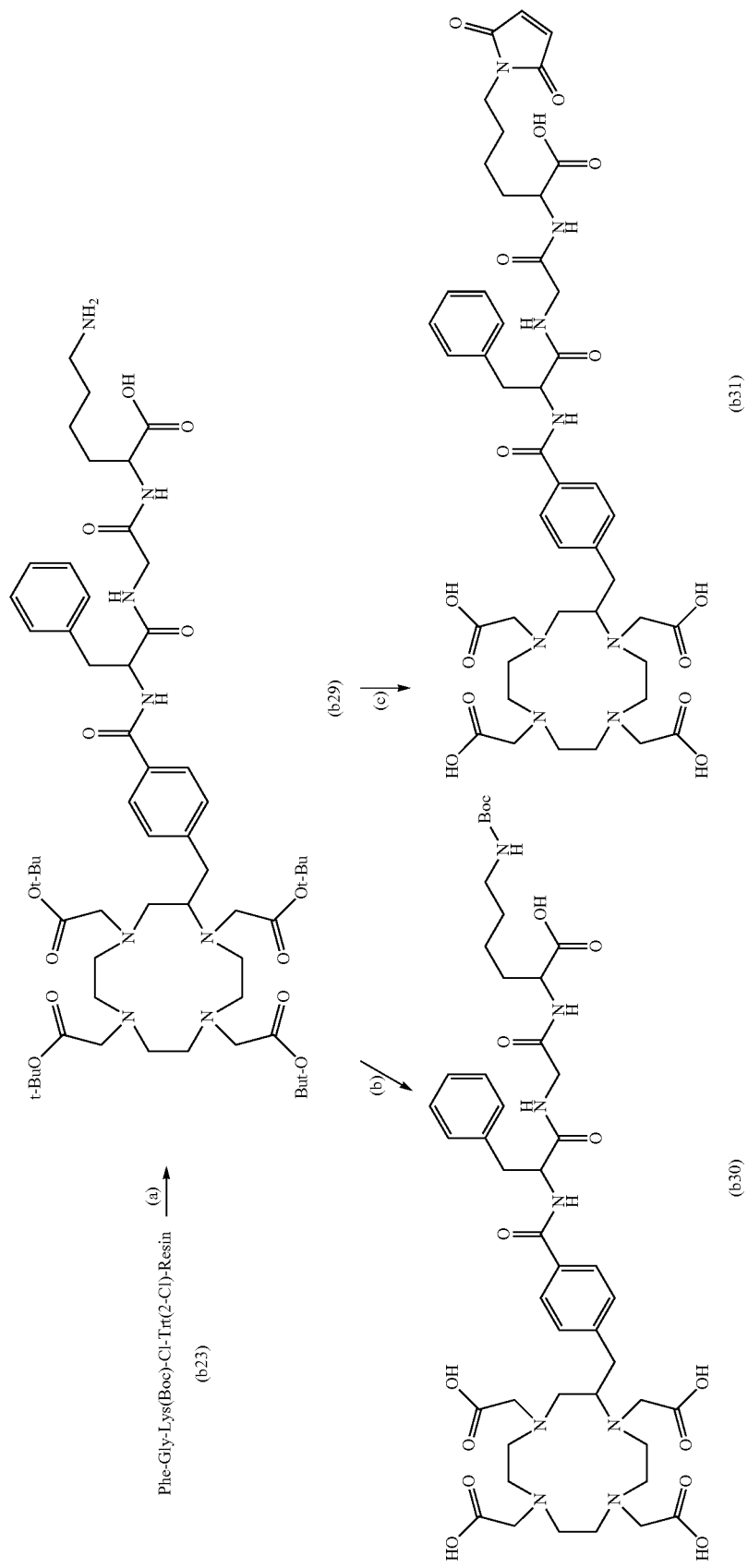

Synthesis Example L7(a): Synthesis of Compound (b29)

By using p-COOH-Bn-DOTA(tBu)₄ (52.4 μmol) as a starting material, similar operation as in Synthesis Example L6(c) was performed, and a TFA salt (2.4 mg, yield: 1.3%) of a compound (b29) (hereinafter, also referred to as "CDOTA-Bn-CO-FGK") was obtained as white crystals.
ESI-MS ([M+K]−H)⁻: m/z 907.36, found: 907.31.

Synthesis Example L7 (b): Synthesis of Compound (b30)

By using a compound (b29) (5.75 μmol) as a starting material, similar operation as in Synthesis Example L6(d) was performed, and a TFA salt (0.4 mg, yield: 71.8%) of a compound (b30) (hereinafter, also referred to as "CDOTA-Bn-CO-FGK(Boc)") was obtained as white crystals.
ESI-MS ([M+K]−H)⁻: m/z 1007.41, found: 1007.31.

Synthesis Example L7(c): Synthesis of Compound (b31)

By using a compound (b29) (0.694 μmol) as a starting material, similar operation as in Synthesis Example L6(e) was performed, and a TFA salt (0.6 mg, yield: 61.4%) of a compound (b31) (hereinafter, also referred to as "CDOTA-Bn-CO-FGK(mal)") was obtained as white crystals.
ESI-MS (M−H)⁻: m/z 949.39, found: 949.43.

Synthesis of CDO3AiBu-FGK(Boc), CDO3AiBu-FGK(Mal), and CDO3AiBu-Phe

Synthesis Example L8: Synthesis of Compound (a23)

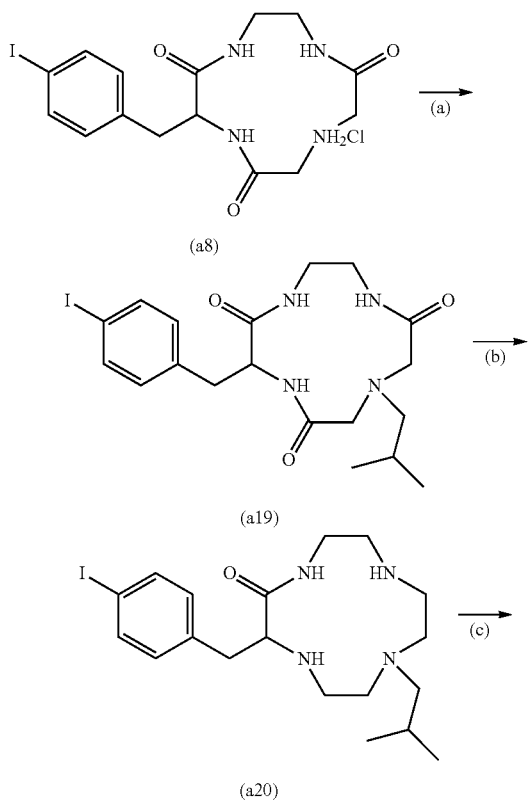

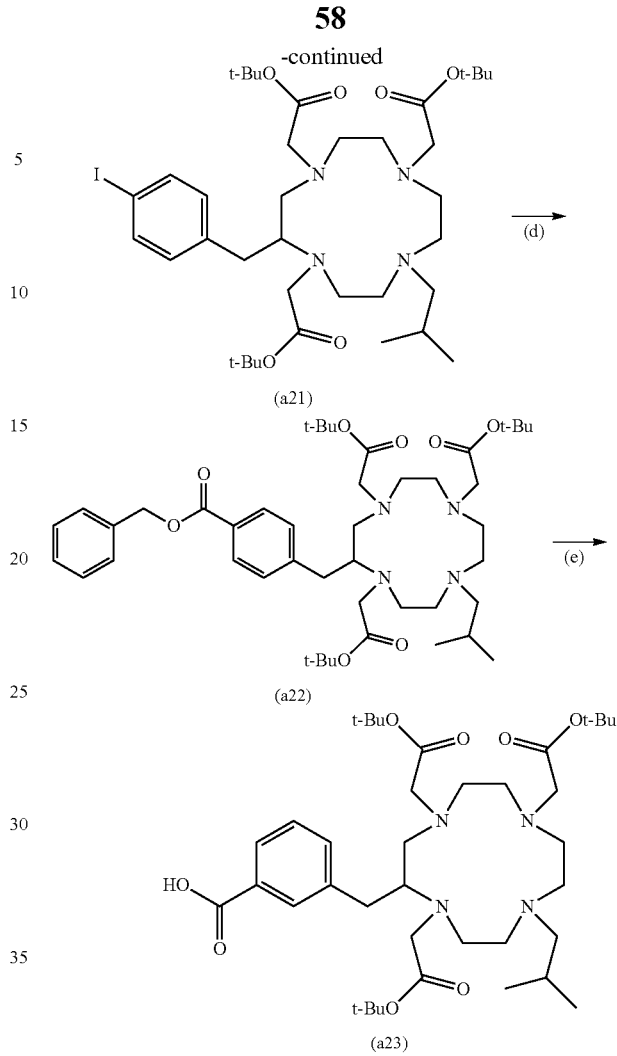

(a) isobutylaldehyde, sodium triacetoxyborohidride, THF, 42.4%; (b) 1M BH₃—THF, THF, 74.7%; (c) tert-butyl bromoacetate, Na₂CO₃, acetonitrile, 58.8%; (d) Pd(OAc)₂, 1,2-bis(diphenylphosphino)ethane, Et₃N, CO, BnOH, DMF, 25.5%; (j) 10% Pd/C, MeOH, 48.8%.

Synthesis Example L8(a): Synthesis of Compound (a19)

A compound (a8) (913 mg, 1.96 mmol) was dissolved in THF (20 mL), and into the obtained mixture, isobutylaldehyde (357 μL, 3.91 mmol), and sodium triacetoxyborohidride (498 mg, 2.35 mmol) were added, and the resultant mixture was stirred at room temperature overnight under an Ar atmosphere. Into the mixture, isobutylaldehyde (179 μL, 1.96 mmol) and sodium triacetoxyborohidride (249 mg, 1.18 mmol) were added, and then the obtained mixture was further stirred at room temperature for 2 hours. The reaction mixture was ice-cooled, water was added, and then the extraction was performed with chloroform three times from the aqueous solution obtained by distilling off the THF under reduced pressure. The organic layer was dried with the addition of sodium sulfate, and then the residue obtained by distilling off the solvent under reduced pressure was formed by a flash chromatography system using chloroform and methanol to obtain a compound (a19) (403 mg, 829 μmol, 42.4%) as white crystals.

¹H NMR (CDCl₃): δ 0.92-0.95 (6H, m, CH₃), 1.68-1.71 (1H, m, CH), 2.40-2.44 (2H, m, CH₂), 2.82-3.30 (8H, overlapped, CH$_2$), 3.61-3.74 (2H, m, CH$_2$), 4.58-4.62 (1H, m, CH), 6.48 (1H, s, NH), 6.66 (1H, s, NH), 6.96-6.98 (2H, d, CH$_2$), 7.56-7.58 (2H, d, CH$_2$), 8.00 (1H, s, NH). ESI-MS (M+H)$^+$: m/z 487.12, found: 487.18.

Synthesis Example L8 (b): Synthesis of Compound (a20)

A compound (a19) (403 mg, 829 µmol) was suspended in 2 mL of THF, the obtained suspension was ice-cooled, and then into the ice-cooled suspension, 13 mL of 0.95M borane-THF complex/THF solution was slowly added under an argon atmosphere, the obtained mixture was stirred for one hour, and then the mixture was refluxed for 22 hours. The resultant mixture was ice-cooled, and into the ice-cooled mixture, 13 mL of methanol was added, and then the mixture was stirred for one hours, and the solvent was distilled off under reduced pressure. After that, 13 mL of methanol was added again into the residue, and the solvent was distilled off under reduced pressure. Into the residue, 13 mL of concentrated hydrochloric acid was added, the obtained mixture was stirred at room temperature for 24 hours, and then the mixture was refluxed for one hour. The resultant mixture was ice-cooled, and into the ice-cooled mixture, a 12.5N sodium hydroxide aqueous solution was added to make the mixture basic, and then the extraction was performed with chloroform. The organic layer was dried with the addition of sodium sulfate, and then the residue obtained by distilling off the solvent under reduced pressure was purified by a flash chromatography system using a solution of chloroform:methanol:25% by mass ammonia water (10:1:0.1) as an elution solvent to obtain a compound (a20) (275 mg, 619 µmol, yield: 74.7%) as a yellow oil.

$^1$H NMR (CDCl$_3$): δ 0.89-0.92 (6H, m, CH$_3$), 1.80-1.84 (1H, m, CH), 2.06-2.89 (19H, overlapped, CH, CH$_2$), 6.92-6.94 (2H, d, CH$_2$), 7.58-7.60 (2H, d, CH$_2$)

Synthesis Example L8(c): Synthesis of Compound (a21)

A compound (a20) (275 mg, 619 µmol) was suspended in 2 mL of acetonitrile, and into the obtained mixture, sodium carbonate (428 mg, 3.10 mmol) was added. The obtained mixture was ice-cooled, and into the ice-cooled mixture, tert-butyl bromoacetate (272 µL, 1.86 mmol) was added dropwise under an argon atmosphere. After completion of the dropwise addition, the obtained mixture was stirred at room temperature for 24 hours, the suspension was filtered, and then the solvent was distilled off from the filtrate under reduced pressure. The residue was formed by a flash chromatography system using chloroform and methanol to obtain a compound (a21) (286 mg, 364 µmol, 58.8%) as a yellow oil.

$^1$H NMR (CDCl$_3$): δ 0.86-0.89 (6H, m, CH$_3$), 1.41-1.50 (27H, m, tBu), 1.86-3.90 (26H, overlapped, CH, CH$_2$), 6.99-7.01 (2H, d, CH$_2$), 7.59-7.61 (2H, d, CH$_2$). ESI-MS (M+H)$^+$: m/z 787.39, found: 787.45.

Synthesis Example L8(d): Synthesis of Compound (a22)

A compound (a21) (286 mg, 364 µmol) was suspended in 3.0 mL of DMF, and into the obtained suspension, Pd(OAc)$_2$ (16.3 mg, 0.0728 mmol), 1,2-bis(diphenylphosphino)ethane (58.0 mg, 0.146 mmol), Et$_3$N (156 µL, 1.12 mmol), and benzyl alcohol (753 µL, 7.28 mmol) were added, and the obtained mixture was refluxed overnight under an atmosphere of carbon monoxide. After the reaction, the residue obtained by distilling off the solvent under reduced pressure was purified by a flash chromatography system using chloroform and methanol to obtain a compound (a22) (73.8 mg, 92.8 µmol, yield: 25.5%) as a yellow oil.

ESI-MS (M+H)$^+$: m/z 795.53, found: 795.40.

Synthesis Example L8(e): Synthesis of Compound (a23)

A compound (a22) (73.8 mg, 92.8 µmol) was dissolved in 1.5 mL of methanol, and then into the obtained mixture, 150 mg of 10% by mass Pd/C was added, and the resultant mixture was stirred at room temperature for 5 hours under an atmosphere of hydrogen. The reaction mixture was filtered, and then the solvent was distilled off under reduced pressure to obtain a compound (a23) (31.9 mg, 45.3 µmol, yield: 48.8%) as white crystals.

ESI-MS (M+H)$^+$: m/z 705.48, found: 705.40.

Synthesis Example L9: Synthesis of Compound (a28)

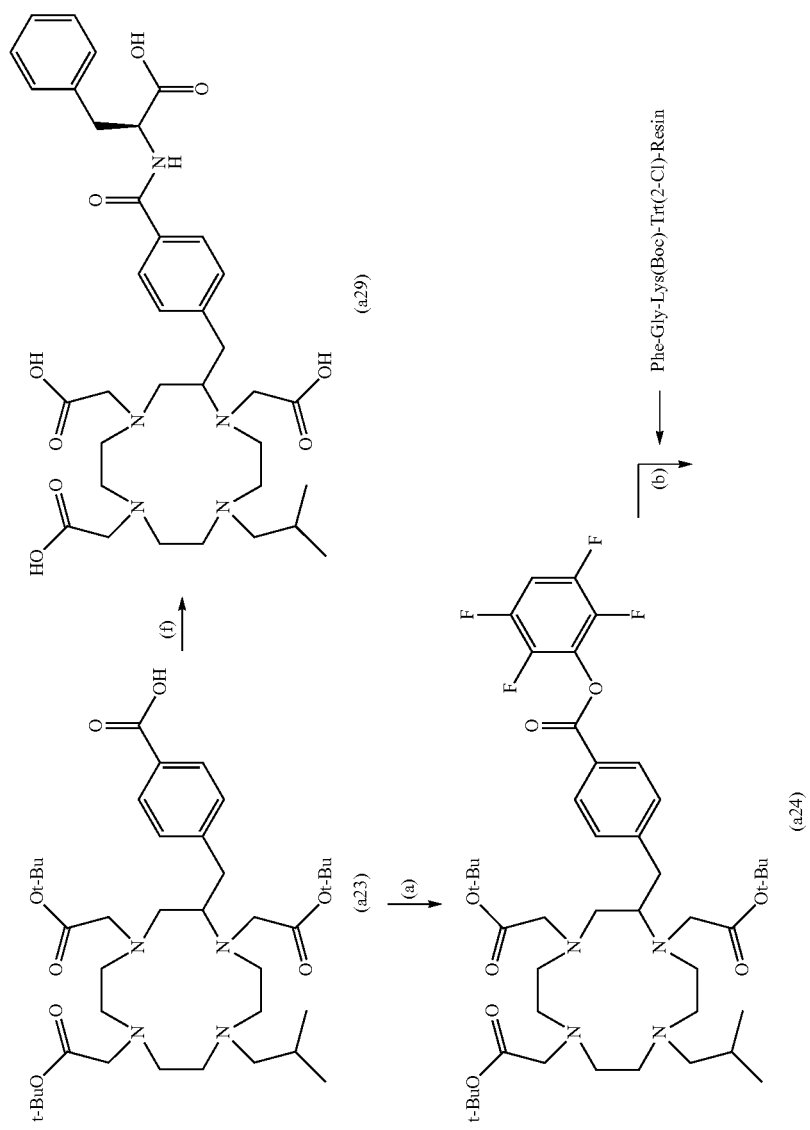

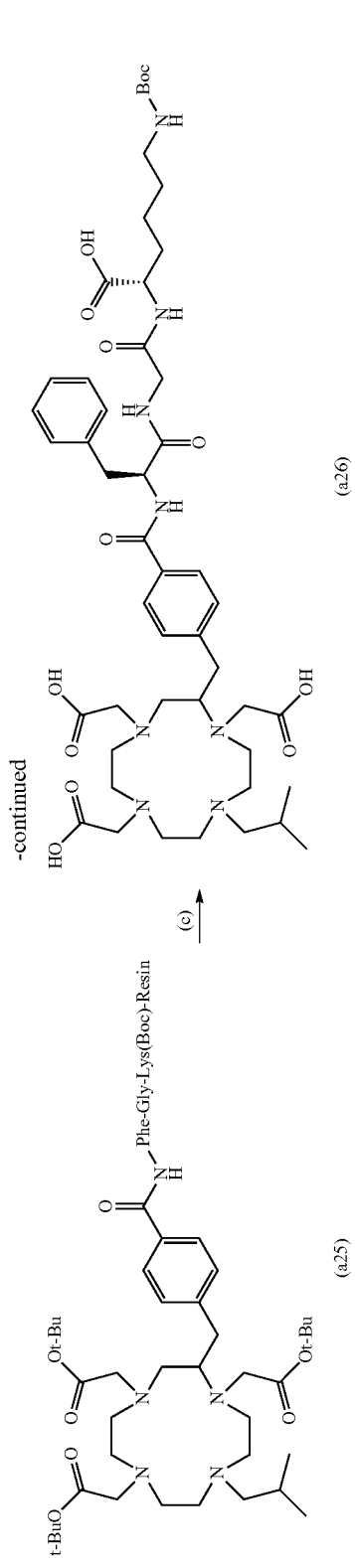
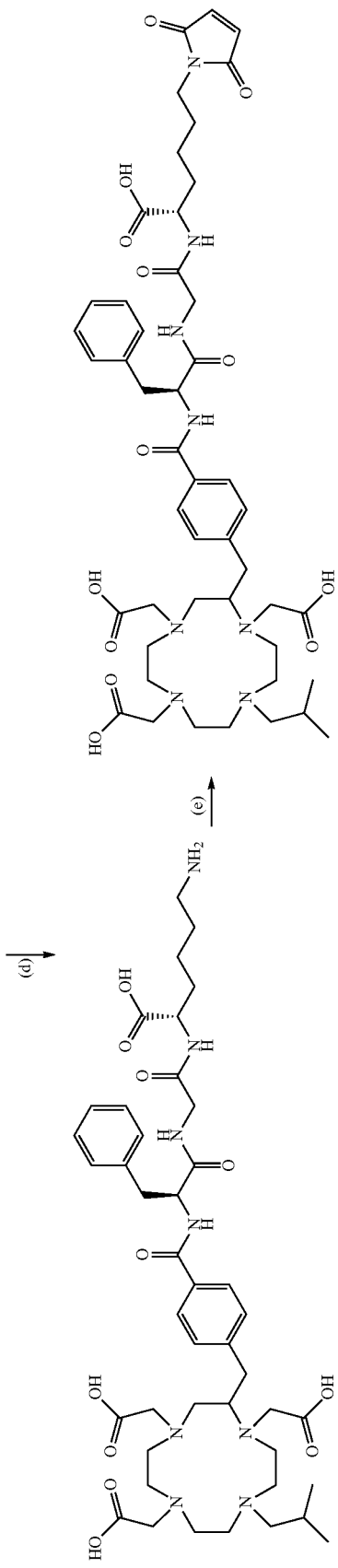
(a) 2,3,5,6-tetrafluorophenol, EDC, Et₃N, DMF, 68.9%; (b) Phe-Gly-Lys(Boc)-Trt(2-Cl)-Resin, DIEA, DMF; (c) AcOH:2,2,2-trifluoroethanol:CH₂Cl₂ = 3:1:6, 2.1%; (d) TFA:TIS:water = 95:2.5:2.5, 6.4%; (e) N-methoxycarbonylmaleimide, sat. NaHCO₃, 45.5%; (f) i) H-Phe-OtBu·HCl, COMU, DIEA, DMF; ii) 10% anisole/TFA, 2.3%.

Synthesis Example L9(a): Synthesis of Compound (a24)

A compound (a23) (23.7 mg, 33.6 μmol) was dissolved in 0.9 mL of DMF, and then into the obtained mixture, 2,3,5,6-tetrafluoro phenol (8.4 mg, 50.6 μmol) and triethylamine (9.3 μL, 66.9 μmol) were added. The resultant mixture was ice-cooled, and into the ice-cooled mixture, EDC (9.6 mg, 50.6 μmol) was added, and then the obtained mixture was returned to room temperature, and was stirred for 4 hours. The solvent was distilled off under reduced pressure, and then the residue was dissolved in ethyl acetate, and the obtained mixture was washed three times with a saturated aqueous solution of ammonium chloride. The organic layer was dried with the addition of sodium sulfate, and then the solvent was distilled off under reduced pressure to obtain a compound (a24) (18.3 mg, 23.2 μmol, yield: 68.9%) as a yellow oil.

Synthesis Examples L9 (b) and L9(c): Synthesis of Compound (a26)

A peptide-extended resin (64.0 mg, 57.6 μmol) obtained by using a Fmoc solid phase synthesis method, N,N-diisopropylethylamine (23.6 μL, 135 μmol), and a compound (a24) (18.3 mg, 23.2 μmol) were dissolved in DMF, and the obtained mixture was gently stirred at room temperature for 16 hours. After completion of the reaction, the resin was washed with DMF and $CH_2Cl_2$.

The obtained resin (a25) was suspended in a solution with a composition of acetic acid:2,2,2-trifluoroethanol:dichloromethane=3:1:6, and the obtained suspension was gently stirred for 2 hours. After completion of the reaction, the resin was removed by filtration, the filtrate was distilled off under reduced pressure, and the residue was azeotropic three times with toluene. For the residue, by a linear gradient method in which HPLC using Imtakt Cadenza 5CD-C18 150×20 mm was used, 0.1% TFA/MilliQ for phase A and 0.1% TFA/MeCN for phase B were used as the mobile phases, and the phases were changed from phase A 95% and phase B 5% to phase A 50% and phase B 50% in the period of 0 to 35 minutes, and changed from the phase A 50% and the phase B 50% to phase A 0% and phase B 100% in the period of 35 to 45 minutes, the purification (retention time: 34.7 minutes) was performed at a flow rate of 5 mL/min, and a desired compound (a26) (hereinafter, also referred to as "CDO3AiBu-FGK(Boc)", 1.0 mg, 0.70 μmol, yield: 2.1%) was obtained.

ESI-MS $(M+H)^+$: m/z 969.53, found: 969.51.

Synthesis Example L9(d): Synthesis of Compound (a27)

A resin (a25) prepared in a similar manner to the above by using a peptide-extended resin (48.3 mg, 43.4 μmol) obtained by using a Fmoc solid phase synthesis method, N,N-diisopropylethylamine (17.8 μL, 102 μmol), and a compound (a24) (18.3 mg, 17.5 μmol) was suspended in a solution with a composition of trifluoroacetic acid:triisopropylsilane:water=95:2.5:2.5, and the obtained suspension was gently stirred for 2 hours. After completion of the reaction, the resin was removed by filtration, the filtrate was distilled off under reduced pressure, and the residue was azeotropic three times with toluene. For white crystals obtained by freeze drying an aqueous solution thathadbeenobtainedbydissolvingthe residue in water and washing the obtained mixture three times with diethyl ether, by a linear gradient method in which HPLC using Imtakt Cadenza 5CD-C18 150×20 mm was used, 0.1% TFA/MilliQ for phase A and 0.1% TFA/MeCN for phase B were used as the mobile phases, and the phases were changed from phase A 95% and phase B 5% to phase A 50% and phase B 50% in the period of 0 to 35 minutes, and changed from the phase A 50% and the phase B 50% to phase A 0% and phase B 100% in the period of 35 to 45 minutes, the purification (retention time: 24.8 minutes) was performed at a flowrate of 5 mL/min, and a desired compound (a27) (hereinafter, also referred to as "CDO3AiBu-FGK", 1.8 mg, 1.25 μmol, yield: 6.4%) was obtained. ESI-MS $(M+H)^+$: m/z 869.48, found: 869.38.

Synthesis Example L9(e): Synthesis Example of Compound (a28)

A compound (a27) (1.8 mg, 2.6 μmol) was dissolved in 150 μL of saturated aqueous solution of sodium hydrogen carbonate, into the obtained mixture, N-methoxycarbonylmaleimide (1.0 mg, 6.5 μmol) was added under ice cooling, and the resultant mixture was stirred for 2 hours under ice cooling. After completion of the reaction, the mixture was adjusted to be acidic with a 5% by mass citric acid aqueous solution. In addition, by a linear gradient method in which HPLC using Imtakt Cadenza 5CD-C18 150×20 mm was used, 0.1% TFA/MilliQ for phase A and 0.1% TFA/MeCN for phase B were used as the mobile phases, the phase A was kept 100% in the period of up to 5 minutes, and then the phases were changed from the phase A 100% and phase B 0% to phase A 40% and phase B 60% in the period of 5 to 35 minutes, and changed from the phase A 40% and the phase B 60% to phase A 0% and phase B 100% in the period of 35 to 50 minutes, the purification (retention time: 30.7 minutes) was performed at a flow rate of 5 mL/min, and a desired compound (a28) (hereinafter, also referred to as "CDO3AiBu-FGK(Mal)", 0.8 mg, 0.57 μmol, yield: 45.5%) was obtained.

ESI-MS $(M+H)^+$: m/z 949.47, found: 949.36.

Synthesis Example L9(f): Synthesis of Compound (a29)

A compound (a23) (2.7 mg, 3.83 μmol) was dissolved in DMF (0.3 mL), and into the obtained mixture, H-PheOtBu.HCl (1.5 mg, 5.75 mol), N,N-diisopropylethylamine (2.9 μL, 17.2 μmol), and (1-cyano-2-ethoxy-2-oxoethylidenaminooxy)dimethylamino-morpholino-carbenium hexafluorophosphate (4.9 mg, 11.5 μmol) were added, and the resultant mixture was stirred at room temperature overnight. The solvent was distilled off under reduced pressure, and then the residue was redissolved in ethyl acetate, the obtained mixture was washed three times with a 5% by mass sodium hydrogen carbonate aqueous solution and further three times with a 5% by mass aqueous solution of citric acid. The organic layer was dried with the addition of sodium sulfate, and then in the residue obtained by distilling off the solvent under reduced pressure, a 10% by mass anisole/TFA solution (2.0 mL) was added, and the obtained mixture was stirred at room temperature for 2 hours. The solvent was distilled off under reduced pressure, and then the residue was azeotropic three times with toluene. For white crystals obtained by distilling off the solvent under reduced pressure from an aqueous solution that had been obtained by dissolving the residue in water and washing the obtained mixture three times with diethyl ether, by a linear gradient method in which HPLC using Imtakt Cadenza 5CD-C18

150×20 mm was used, 0.1% TFA/MilliQ for phase A and 0.1% TFA/MeCN for phase B were used as the mobile phases, and the phases were changed from phase A 100% and phase B 0% to phase A 40% and phase B 60% in the period of 0 to 30 minutes, and changed from the phase A 40% and the phase B 60% to phase A 0% and phase B 100% in the period of 30 to 35 minutes, the purification (retention time: 25.2 minutes) was performed at a flow rate of 5 mL/min, and a desired compound (a29) (hereinafter, also referred to as "CDO3AiBu-Phe", 0.1 mg, 8.8 μmol, yield: 2.3%) was obtained.

ESI-MS (M+H)$^+$: m/z 684.36ound: 684.27.

Preparation of Bifunctional Chelate Reagent-Bound Fab

Synthesis Example F1: Preparation of Fab (Derived from Rabbit Serum IgG) and IT-Fab (Derived from Rabbit Serum IgG) (Preparation of Fab (Derived from Rabbit Serum IgG))

Rabbit serum IgG (9 mg) was dissolved in 1.5 mL of 20 mM phosphate buffer solution (pH 7.0) containing 10 mM Na$_2$EDTA and 20 mM cysteine, and into the obtained mixture, 500 μL of immobilized papain 50% slurry (available from Thermo Fisher Scientific K.K., Yokohama, Japan) was added, and the resultant mixture was incubated at 37° C. for 42 hours. After completion of the reaction, into the mixture, 2 mL of 10 mM 4tris-hydrochloric acid buffer solution (pH 7.5) was added, the obtained mixture was filtered by a filter of 0.45 m, and the filtrate was recovered. The recovered filtrate was replaced with a 20 mM phosphate buffer solution (pH 7.0) by using an ultrafiltration membrane of 10 kDa, and the resultant mixture was concentrated to 1 mL. After that, the concentrated mixture was purified by using a protein A column to obtain Fab. The formation of the obtained Fab was confirmed by SE-HPLC eluting at a flow rate of 1.0 mL/min using a 0.1 M phosphate buffer solution (pH 6.8) as an elution solvent, and the concentration was calculated by measuring at A280.
(Preparation of IT-Fab (Derived from Rabbit Serum IgG))

A Fab solution (100 μL, 5 mg/mL) was prepared by using a 2 mM EDTA-containing 0.16 M borate buffer solution (pH 8.0) that had been sufficiently degassed, and into the prepared Fab solution, 2-iminothiolane (2-IT) (5 μL, 2.88 mg/mL) dissolved in the same buffer solution was added in 1-μL portions while being stirred, and the obtained mixture was stirred gently at 37° C. for 30 minutes. After the reaction, by a spin column method (Analytical Biochemistry, 1984, 142, 68-78) using Sephadex G-50 Fine equilibrated with a 2 mM EDTA-containing 0.1 M phosphate buffer solution (pH 6.0) that had been sufficiently degassed, the excessive 2-IT in the reaction mixture was removed, and an IT-Fab (derived from Rabbit serum IgG) solution was obtained. The number of thiol groups introduced per molecule of Fab was measured by using 2,2'-dipyridyldisulfide (Archives of Biochemistry and Biophysics, 1967, 119, 41-49).

Synthesis Example F2: Preparation of Fab (Derived from Anti-c-Kit IgG) and IT-Fab (Derived from Anti-c-Kit IgG)

In a similar manner to Synthesis Example F1 except that the Rabbit serum IgG (9 mg) was changed to anti-c-kit IgG (9 mg), Fab (derived from anti-c-kit IgG) and IT-Fab (derived from anti-c-kit IgG) were prepared.

Preparation of Fab-Bound Ligand

Synthesis Example: Preparation of CDO3AEt-FGK-Fab (Derived from Rabbit Serum IgG), CDO3AEt-FGK-Fab (Derived from Anti-c-Kit IgG), DO3A-EDA-Fab (Derived from Rabbit Serum IgG), CDOTA-Bn-CO-FGK-Fab (Derived from Anti-c-Kit IgG), DO3A-Bn-SCN-MVK-Fab (Derived from Rabbit Serum IgG), DO3A-Bn-CO-FGK-Fab (Derived from Rabbit Serum IgG), CDO3AiBu-FGK-Fab (Derived from Rabbit Serum IgG), and CDO3AiBu-FGK-Fab (Derived from Anti-c-Kit IgG)

Into an IT-Fab (derived from Rabbit serum IgG) solution (100 μL), CDO3AEt-FGK(Mal) dissolved in H$_2$O (5 μL, 20 equivalents to the thiol group) was added in 1-μL portions, and the obtained mixture was reacted at 37° C. for 2 hours. Next, an iodoacetamide solution was prepared by using a 0.1 M phosphate buffer solution (pH 6.0), 500 equivalents of the prepared iodoacetamide solution was added to the remaining thiol groups, and then the mixture was reacted at 37° C. for one hour to alkylate unreacted thiol groups. After that, the resultant mixture was purified by a spin column method using Sephadex G-50 Fine equilibrated with a 0.25 M acetate buffer solution (pH 5.5) to obtain a CDO3AEt-FGK-Fab (derived from Rabbit serum IgG) solution. The number of units derived from CDO3AEt-FGK(Mal) introduced per molecule of Fab was determined by subtracting the number of thiols previously determined from the number of thiols measured by using DPS before adding the iodoacetamide (Archives of Biochemistry and Biophysics, 1967, 119, 41-49).

In a similar manner to the above except that the CDO3AEt-FGK(Mal) was changed to each of DO3A-EDA (Mal), DO3A-Bn-SCN-MVK(Mal), DO3A-Bn-CO-FGK(Mal), and CDO3AiBu-FGK(Mal), a DO3A-EDA-Fab (derived from Rabbit serum IgG) solution, a DO3A-Bn-SCN-MVK-Fab (derived from Rabbit serum IgG) solution, a DO3A-Bn-CO-FGK-Fab (derived from Rabbit serum IgG) solution, and a CDO3AiBu-FGK-Fab (derived from Rabbit serum Ig) solution were obtained, respectively.

In a similar manner to the above except that the IT-Fab (derived from Rabbit serum IgG) solution was changed to an IT-Fab (derived from anti-c-kit IgG) solution, a CDO3AEt-FGK-Fab (derived from anti-c-kit IgG) solution was obtained.

In a similar manner to the above except that the IT-Fab (derived from Rabbit serum IgG) solution was changed to an IT-Fab (derived from anti-c-kit IgG) solution, and the CDO3AEt-FGK(Mal) was changed to CDOTA-Bn-CO-FGK(Mal), a CDOTA-Bn-CO-FGK-Fab (derived from anti-c-kit IgG) solution was obtained.

In a similar manner to the above except that the IT-Fab (derived from Rabbit serum IgG) solution was changed to an IT-Fab (derived from anti-c-kit IgG) solution, and the CDO3AEt-FGK(Mal) was changed to CDO3AiBu-FGK (Mal), a CDO3AiBu-FGK-Fab (derived from anti-c-kit IgG) solution was obtained.

Synthesis Example: Preparation of DOTA-Bn-SCN-Fab (Derived from Anti-c-Kit IgG)

A Fab solution (100 μL, 5.0 mg/mL) was prepared by using a 0.16 M borate buffer solution (pH 8.5), and into the obtained Fab solution, DOTA-Bn-SCN (available from Macrocyclics, Inc., USA, 14 μL, 10 mg/mL) dissolved in the same buffer solution was added, and the obtained mixture was left to stand at 4° C. overnight. After the reaction, by a spin column method using Sephadex G-50 Fine equilibrated with a 0.25 M acetate buffer solution (pH 5.5) that had been sufficiently degassed, excessive DOTA-Bn-SCN was removed, and DOTA-Bn-SCN-Fab (derived from anti-c-kit IgG) was obtained.

In this regard, chemical structures of the above-described CDO3AEt-FGK-Fab, DO3A-Bn-CO-FGK-Fab, CDOTA-Bn-CO-FGK-Fab, and CDO3AiBu-FGK-Fab are as described above. Further, chemical structures of DO3A-EDA-Fab, DO3A-Bn-SCN-MVK-Fab, and DOTA-Bn-SCN-Fab are as follows.

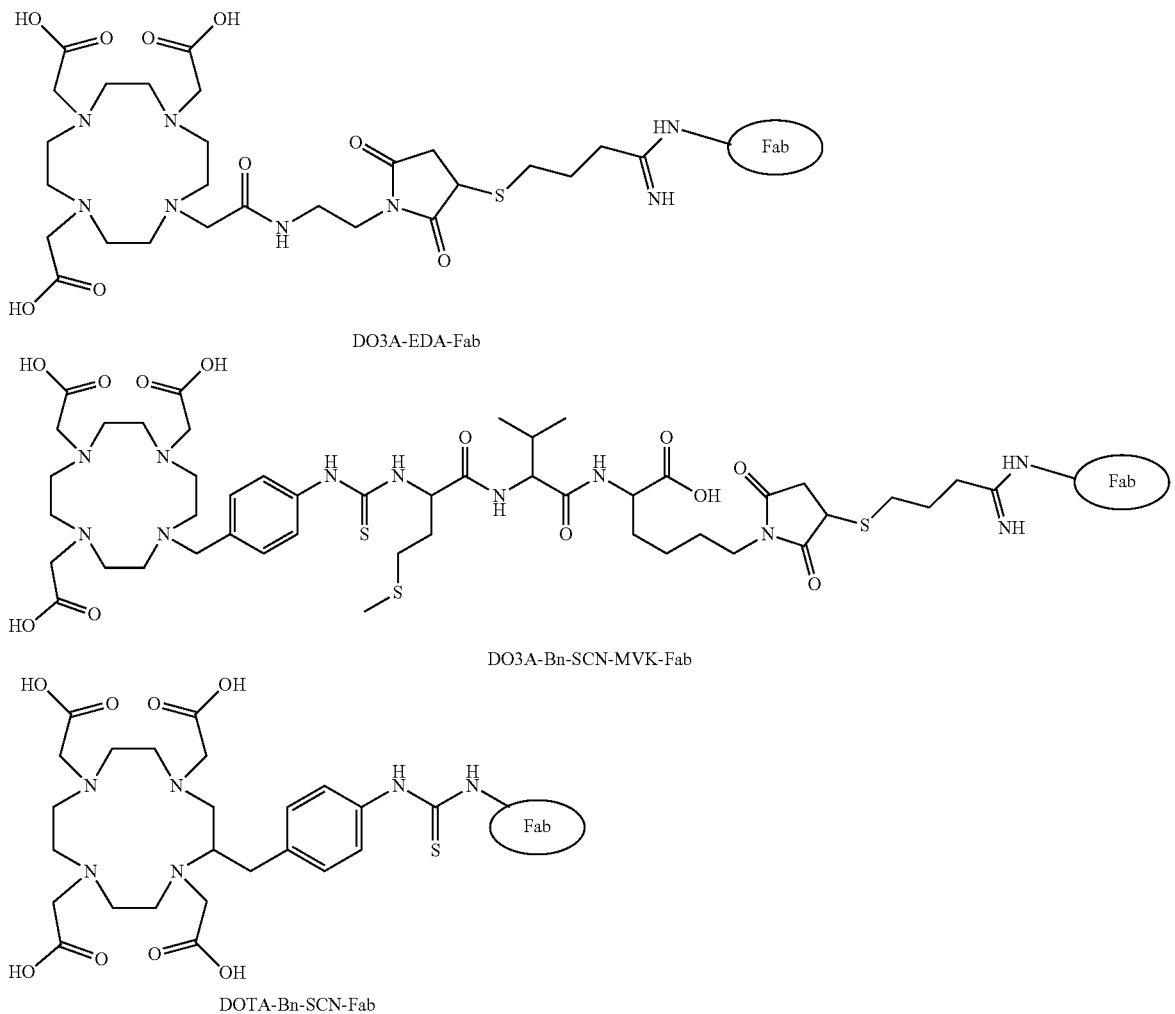

Preparation of Metal Complex Compound

Synthesis Example: Preparation of $^{111}$In-CDO3AEt-FGK-Fab (Derived from Rabbit Serum IgG), $^{111}$In-CDO3AEt-FGK-Fab (Derived from Anti-c-Kit IgG), [111]In-DO3A-EDA-Fab (Derived from Rabbit Serum IgG), $^{111}$In-CDOTA-Bn-CO-FGK-Fab (Derived from Anti-c-Kit IgG), [111]In-DO3A-Bn-SCN-MVK-Fab (Derived from Rabbit Serum IgG), [111]In-DO3A-Bn-CO-FGK-Fab (Derived from Rabbit Serum IgG), $^{111}$In-CDO3AiBu-FGK-Fab (Derived from Rabbit Serum IgG), $^{111}$In-CDO3AiBu-FGK-Fab (Derived from Anti-c-Kit IgG), $^{111}$In-DOTA-Bn-SCN-Fab (Derived from Anti-c-Kit IgG), $^{111}$In-CDO3AEt-FGK(Boc), $^{111}$In-CDOTA-Bn-CO-FGK(Boc), [111]In-DO3A-Bn-SCN-MVK (Bzo), and [111]In-DO3A-Bn-CO-FGK(Boc)

[111]InCl$_3$ (45 μL) was mixed in a 1 M acetate buffer solution (pH 5.5, 5 μL), and the obtained mixture was left to stand at room temperature for 5 minutes. In the resultant mixture, a CDO3AEt-FGK-Fab (derived from Rabbit serum IgG) solution (30 μL) was mixed, and then the obtained mixture was incubated at 40° C. for 90 minutes. Into the incubated mixture, DTPA was added so as to have a final concentration of 10 mM, and then the obtained mixture was left to stand at room temperature for 18 hours. The resultant mixture was purified by a spin column method using Sephadex G-50 Fine equilibrated with 0.1 M D-PBS (pH 7.4) to prepare $^{111}$In-CDO3AEt-FGK-Fab. In a similar manner to the above except that the CDO3AEt-FGK-Fab (derived from Rabbit serum IgG) solution was changed to each of a CDO3AEt-FGK-Fab (derived from anti-c-kit IgG) solution, a DO3A-EDA-Fab (derived from Rabbit serum IgG) solution, a CDOTA-Bn-CO-FGK-Fab (derived from anti-c-kit IgG) solution, a DO3A-Bn-SCN-MVK-Fab solution (derived from Rabbit serum IgG), a DO3A-Bn-CO-FGK-Fab (derived from Rabbit serum IgG) solution, a CDO3AiBu-FGK-Fab (derived from Rabbit serum IgG) solution, a DOTA-Bn-SCN-Fab (derived from anti-c-kit IgG) solution, a CDO3AEt-FGK(Boc) solution, a CDOTA-Bn-CO-FGK (Boc) solution, a DO3A-Bn-SCN-MVK(Bzo) solution, and a DO3A-Bn-CO-FGK(Boc) solution, $^{111}$In-CDO3AEt-FGK-Fab (derived from anti-c-kit IgG), $^{111}$In-DO3A-EDA-Fab (derived from Rabbit serum IgG), $^{111}$In-CDOTA-Bn-CO-FGK-Fab (derived from anti-c-kit IgG), $^{111}$In-DO3A-Bn-SCN-MVK-Fab (derived from Rabbit serum IgG), $^{111}$In-DO3A-Bn-CO-FGK-Fab (derived from Rabbit serum IgG), $^{111}$In-CDO3AiBu-FGK-Fab (derived from Rabbit serum IgG), $^{111}$In-DOTA-Bn-SCN-Fab (derived from anti-c-kit IgG), $^{111}$In-CDO3AEt-FGK(Boc), $^{111}$In-CDOTA-Bn-CO-FGK(Boc), $^{111}$In-DO3A-Bn-SCN-MVK(Bzo), and $^{111}$In-DO3A-Bn-CO-FGK(Boc) were prepared, respectively.

Examination of Characteristics

Incubation Test with BBMVs (Renal Brush Border Membrane Vesicles)

Renal brush border membrane vesicles (BBMVs) were prepared from the kidney of a male Wistar-strain rat (200 to 250 g) in accordance with a method of Hori, et al. (Biochemical Pharmacology 45: 1763-1768, 1993). All operations were performed on ice. Into the cortex, a 12 mM tris-hydrochloric acid buffer solution (pH 7.1) containing 300 mM mannitol and 5 mM EGTA were added in an amount 4 to 5 times the weight of the cortex, and the obtained mixture was homogenized for 2 minutes by a Polytron homogenizer (PT-3100, available from Kinematica GmgH Littau, Switzerland), and the homogenized mixture was diluted with the same buffer solution to give a 10% homogenate. Next, the 10% homogenate was diluted twice with distilled water, and then into the diluted mixture, a $MgCl_2$ aqueous solution adjusted to 1.0 M was added so as to have a final concentration of 10 mM, and the obtained mixture was left to stand for 15 minutes. After that, the obtained homogenate was centrifuged at 1,900 g, and the supernatant was further centrifuged at 24,000 g for 30 minutes. The precipitate was resuspended in a 6 mM tris-hydrochloric acid buffer solution (pH 7.1) containing 150 mM mannitol and 2.5 mM EGTA in an amount 20 times the weight of the cortex, and the obtained suspension was homogenized by a Teflon (registered trademark) homogenizer (1,000 rpm, 10 strokes). Next, into the homogenized suspension, a 1.0 M $MgCl_2$ aqueous solution was added so as to have a final concentration of 10 mM, and the obtained suspension was left to stand for 15 minutes, and then the homogenate was centrifuged at 1,900 g, and the supernatant was further centrifuged at 24,000 g for 30 minutes. The obtained precipitate was suspended in a 0.1 M phosphate buffer solution (pH 7.0) in an amount 10 times the weight of the cortex, and the obtained suspension was homogenized again bya Teflon (registered trademark) homogenizer (1,000 rpm, 10 strokes). Next. The homogenate was centrifuged at 24,000 g for 30 minutes to obtain BBMVs as a precipitate. Next, the precipitate of BBMVs was resuspended in a 0.1 M phosphate buffer solution (pH7.0), and the obtained suspension was passed through a needle of 0.4×19 mm ten times to make the vesicles uniform in size. In incubation experiment, the resultant suspension was diluted to have a protein concentration of 10 mg/mL before use. For the prepared BBMVs, by measuring an activity of β-galactosidase as a lysosome marker enzyme by using p-nitrophenyl-β-D-galacto-pyranoside, the contamination of lysosomal enzymes was evaluated (Plant Physiology 55: 94-98, 1975). In addition, activities of γ-glutamyl transferase and aminopeptidase were measured by using L-γ-glutamyl-p-nitroanilide, and L-leucine-p-nitroanilide in accordance with methods of Glossmann, et al. (FEBS Letters 19: 340-344, 1972) and Kramers, et al. (European Journal of Biochemistry 99: 345-351, 1979).

(Incubation Test)

An incubation experiment of BBMVs and $^{111}$In-labeled low molecular model substrate was performed by the following method. BBMVs (10 μL) prepared so as to have a protein concentration of 10 mg/mL was preincubated at 37° C. for 10 minutes. After that, into the preincubated BBMVs, a $^{111}$In-CDO3AEt-FGK(Boc) solution (10 μL) dissolved in PBS after removal of excessive ligands by reversed-phase HPLC was added, and the obtained mixture was incubated at 37° C. for 2 hours. Into the BBMVs mixture, ethanol was added so as to have an ethanol concentration of 60%, and the obtained mixture was centrifuged at 5000 rpm for 10 minutes. After recovery of the supernatant, 60% ethanol was added to the precipitate, the obtained mixture was centrifuged again in a similar manner to the above, and then the supernatant was recovered. The obtained supernatant was subjected to an analysis performed at a flow rate of 1 mL/min by a linear gradient method using HPLC in which Imtakt Unison US-C18 150×4.6 mm was used, and 0.1% TFA/MilliQ for phase A and 0.1% TFA/MeCN for phase B were used as the mobile phases, and the phases were changed from phase A 100% and phase B 0% to phase A 55% and phase B 45% in the period of 0 to 30 minutes.

FIG. 1 shows experimental results of incubation of $^{111}$In-CDO3AEt-FGK(Boc) with BBMVs.

An incubation experiment similar to the above was performed except that the $^{111}$In-CDO3AEt-FGK(Boc) solution was changed to each of a $^{111}$In-CDOTA-Bn-CO-FGK(Boc) solution, a $^{111}$In-DO3A-Bn-CO-FGK(Boc) solution, a $^{111}$In-DO3A-Bn-SCN-MVK(Bzo) solution, and a $^{111}$In-CDO3AiBu-FGK(Boc) solution, and a control experiment was performed without using BBMVs.

Figure 2:
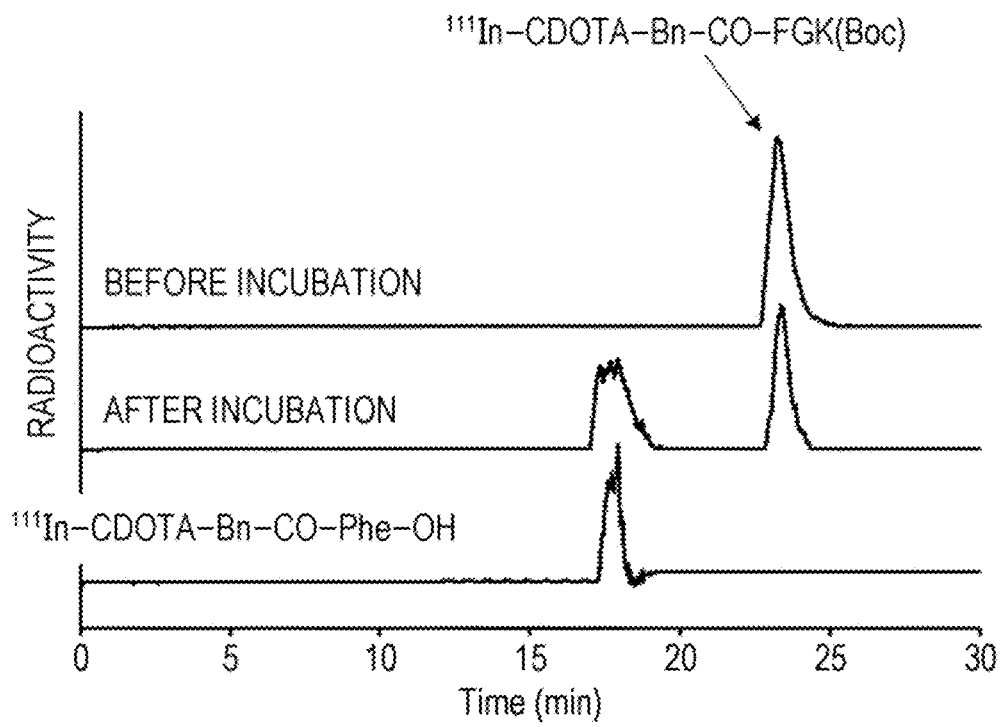
FIG. 2 shows experimental results of incubation of a $^{111}$In-CDOTA-Bn-CO-FGK(Boc) solution with BBMVs.

FIG. 2 shows experimental results of incubation of a $^{111}$In-CDOTA-Bn-CO-FGK(Boc) solution with BBMVs.

Figure 3:
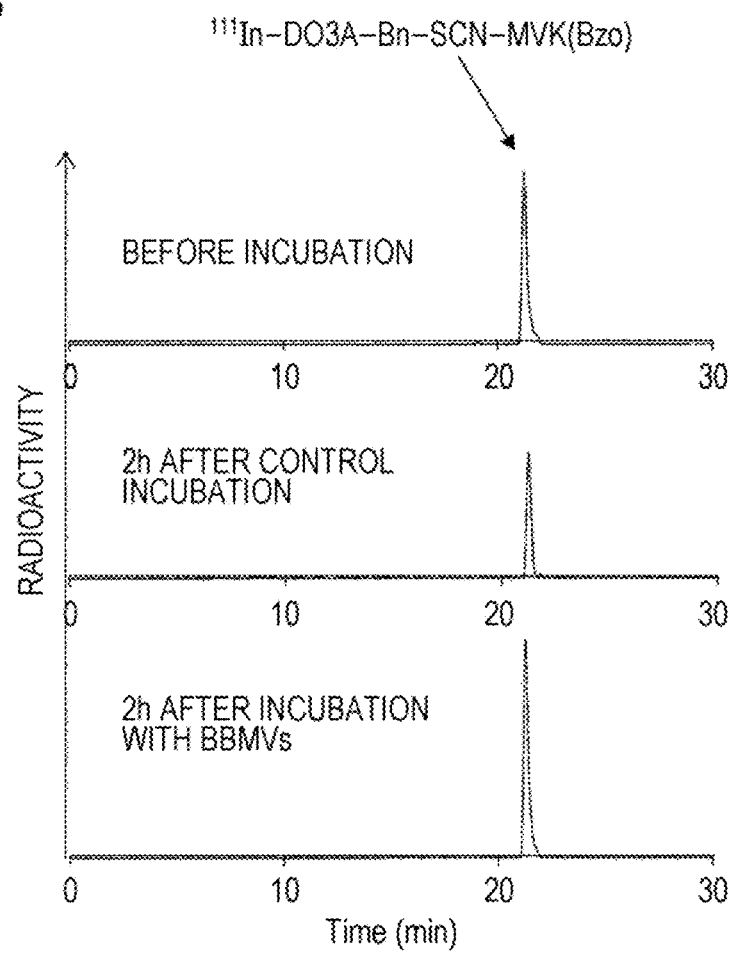
FIG. 3 shows experimental results of incubation of $^{111}$In-DO3A-Bn-SCN-MVK(Bzo) with BBMVs.

FIG. 3 shows experimental results of incubation of $^{111}$In-DO3A-Bn-SCN-MVK(Bzo) with BBMVs.

Figure 4:
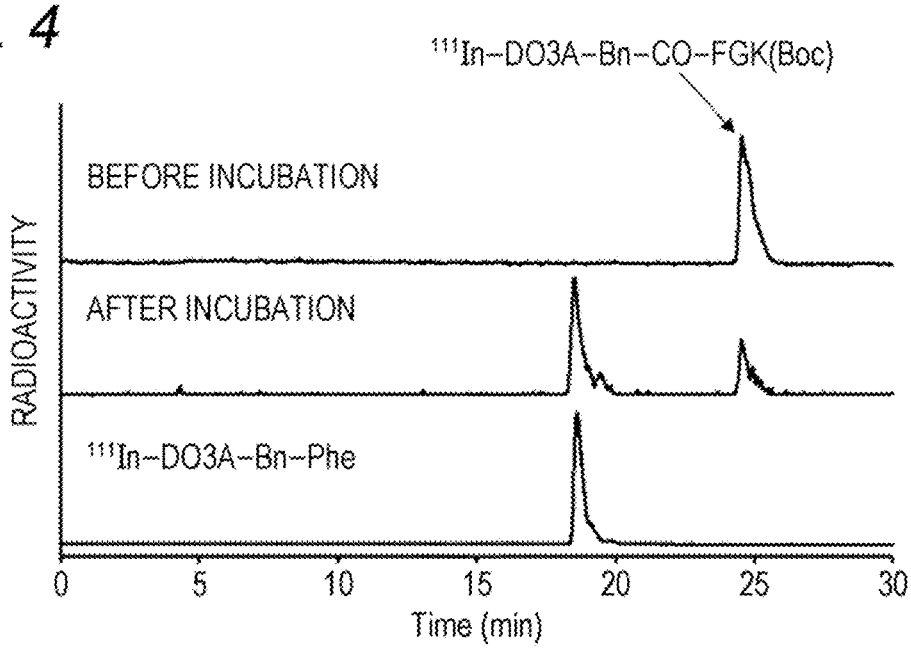
FIG. 4 shows experimental results of incubation of $^{111}$In-DO3A-Bn-CO-FGK(Boc) with BBMVs.

FIG. 4 shows experimental results of incubation of $^{111}$In-DO3A-Bn-CO-FGK(Boc) with BBMVs.

Figure 5:
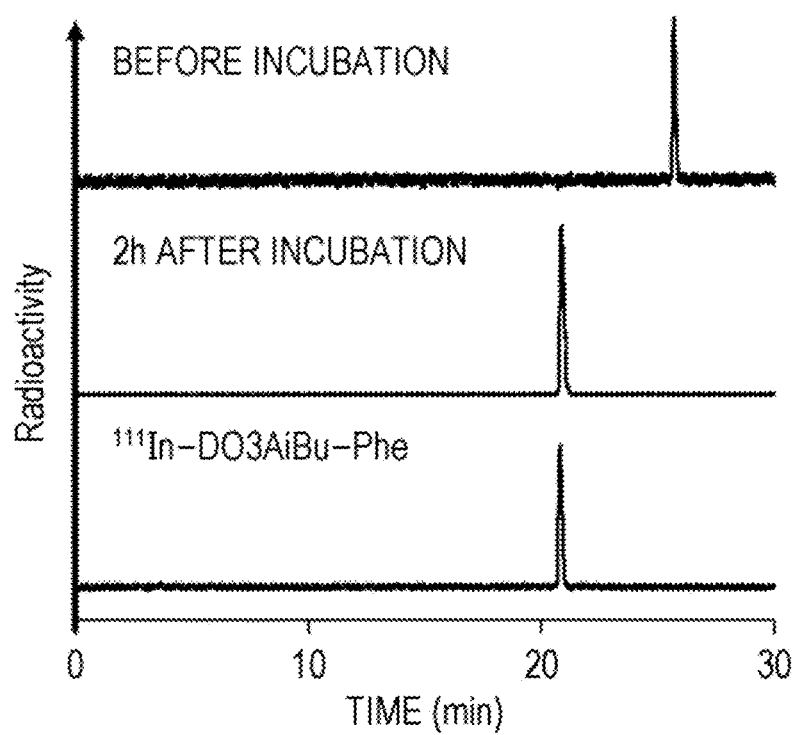
FIG. 5 shows experimental results of incubation of $^{111}$In-CDO3AiBu-FGK(Boc) with BBMVs.

FIG. 5 shows experimental results of incubation of $^{111}$In-CDO3AiBu-FGK(Boc) with BBMVs.

From the above-described experimental results, it can be understood that in each of the $^{111}$In-CDO3AEt-FGK(Boc), $^{111}$In-CDOTA-Bn-CO-FGK(Boc), $^{111}$In-DO3A-Bn-CO-FGK(Boc), and $^{111}$In-CDO3AiBu-FGK(Boc), which are compounds each having a benzylamide structure, similarly to the compound of the invention of the present application, as a linking group, a chelate ligand site is released by the incubation with BBMVs. On the other hand, in a compound $^{111}$In-DO3A-Bn-SCN-MVK(Bzo) having a thiourea structure as a linking group, any released substance is not observed.

(Examination of Stability of Metal Complex Compound in Mouse Plasma)

$^{111}$In-CDO3AEt-FGK-Fab (derived from Rabbit serum IgG) (10 μL) dissolved in PBS was added into mouse plasma (90 μL), and the obtained mixture was incubated at 37° C. Part of the incubated mixture was collected after the lapse of 1, 3, 6, and 24 hours, and by analyzing each of the collected mixtures by RP-TLC using a solution of methanol:10% by mass ammonium acetate aqueous solution=3:2 as a developing solvent, proportion of the radioactivity of the unchanged drug ($^{111}$In-CDO3AEt-FGK-Fab) was calculated, and the results were shown in Table 1.

TABLE 1

|   | Percent of intact (%) |
|---|---|
| 1 h | 95.5 ± 0.31 |
| 3 h | 95.5 ± 0.89 |
| 6 h | 95.6 ± 0.63 |
| 24 h | 94.8 ± 0.58 |

In a similar manner to the above except that the $^{111}$In-CDO3AEt-FGK-Fab (derived from Rabbit serum IgG) was changed to $^{111}$In-CDO3AEt-FGK-Fab (derived from anti-c-kit IgG), the stability test in mouse plasma was performed. After incubation for 2 hours, proportion of the radioactivity of the unchanged drug ($^{111}$In-CDO3AEt-FGK-Fab) was 95.2±0.3%.

In a similar manner to the above except that the $^{111}$In-CDO3AEt-FGK-Fab (derived from Rabbit serum IgG) was changed to $^{111}$In-CDOTA-Bn-CO-FGK-Fab (derived from anti-c-kit IgG), the stability test in mouse plasma was performed. After incubation for 2 hours, proportion of the radioactivity of the unchanged drug ($^{111}$In-CDOTA-Bn-CO-FGK-Fab) was 95.2±0.3%.

In a similar manner to the above except that the $^{111}$In-CDO3AEt-FGK-Fab (derived from Rabbit serum IgG) was changed to $^{111}$In-CDO3AiBu-FGK-Fab (derived from Rabbit serum IgG), the stability test in mouse plasma was performed. Experimental results are shown in Table 2.

TABLE 2

|   | Percent of intact (%) |
|---|---|
| 1 h | 92.0 ± 0.1% |
| 6 h | 93.6 ± 0.3% |
| 24 h | 91.4 ± 1.6% |

(Examination of Biokinetics of Metal Complex Compound in Mouse]

Each of the metal complex compounds prepared in Examples and Comparative Examples were diluted with D-PBS(−) (pH 7.4). A $^{111}$In-CDO3AEt-FGK-Fab (derived from Rabbit serum IgG) solution (0.3 μCi/100 μL/mouse) adjusted to have an unmodified Fab concentration of 5 μg/100 μL was intravenously administered to the tail of each of male ddY-strain mice aged 6 weeks. Three mice in each group were slaughtered after the lapse of 10, and 30 minutes, and 1, 3, 6, and 24 hours from the administration, and organs of interest were collected from each of the mice and weighed, and then the radioactivity was measured by an auto well gamma system. Further, the feces and urine were collected respectively after the lapse of 6, and up to 24 hours, and the radioactivity was measured. In a similar manner to the above, with the intravenous injection to the tail of each of male ddY-strain mice aged 6 weeks by using a $^{111}$In-CDO3AEt-FGK-Fab (derived from anti-c-kit IgG) solution, the radioactivity was measured for the organs of interest, the feces, and the urine. As a control compound, $^{111}$In-DO3A-EDA-Fab (derived from Rabbit serum IgG) prepared in a similar manner to the above was used.

Table 3 shows measurement results of the radioactivity in a mouse body by $^{111}$In-CDO3AEt-FGK-Fab (derived from Rabbit serum IgG).

Table 4 shows measurement results of the radioactivity in a mouse body by $^{111}$In-CDO3AEt-FGK-Fab (derived from anti-c-kit IgG).

Table 5 shows measurement results of the radioactivity in a mouse body by $^{111}$In-DO3A-EDA-Fab (derived from Rabbit serum IgG).

In a similar manner to the above, by using each of a $^{111}$In-CDOTA-Bn-CO-FGK-Fab (derived from anti-c-kit IgG) solution, a $^{111}$In-DO3A-Bn-SCN-MVK-Fab (derived from Rabbit serum IgG) solution, a $^{111}$In-DO3A-Bn-CO-FGK-Fab (derived from Rabbit serum IgG) solution, a $^{111}$In-CDO3AiBu-FGK-Fab (derived from Rabbit serum IgG) solution, a $^{111}$In-CDO3AiBu-FGK-Fab (derived from anti-c-kit IgG) solution, and a $^{111}$In-DOTA-Bn-SCN-Fab (derived from anti-c-kit IgG) solution, with the intravenous injection to the tail of each of male ddY-strain mice aged 6 weeks, the radioactivity was measured for the organs of interest, the feces, and the urine.

Table 6 shows measurement results of the radioactivity in a mouse body by $^{111}$In-CDOTA-Bn-CO-FGK-Fab (derived from anti-c-kit IgG).

Table 7 shows measurement results of the radioactivity in a mouse body by $^{111}$In-DO3A-Bn-SCN-MVK-Fab (derived from Rabbit serum IgG).

Table 8 shows measurement results of the radioactivity in a mouse body by $^{111}$In-DO3A-Bn-CO-FGK-Fab (derived from Rabbit serum IgG).

Table 9 shows measurement results of the radioactivity in a mouse body by $^{111}$In-CDO3AiBu-FGK-Fab (derived from Rabbit serum IgG).

Table 10 shows measurement results of the radioactivity in a mouse body by $^{111}$In-CDO3AiBu-FGK-Fab (derived from anti-c-kit IgG).

Table 11 shows measurement results of the radioactivity in a mouse body by $^{111}$In-DOTA-Bn-SCN-Fab (derived from anti-c-kit IgG).

Figure 6A:
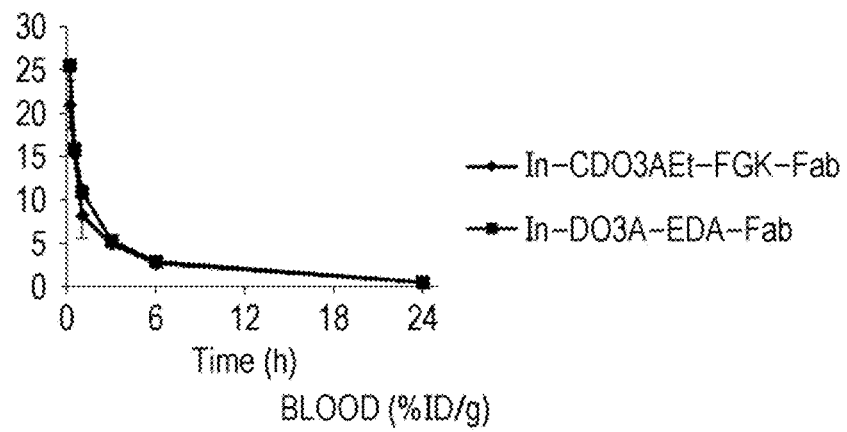
FIGS. 6A-6C show comparisons between the results of $^{111}$In-CDO3AEt-FGK-Fab (derived from Rabbit serum IgG) and $^{111}$In-DO3A-EDA-Fab (derived from Rabbit serum IgG).
Figure 6B:
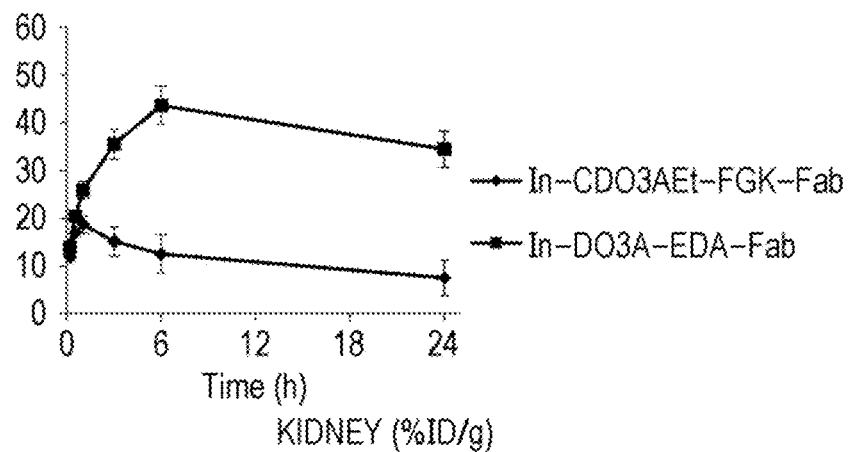
Figure 6C:
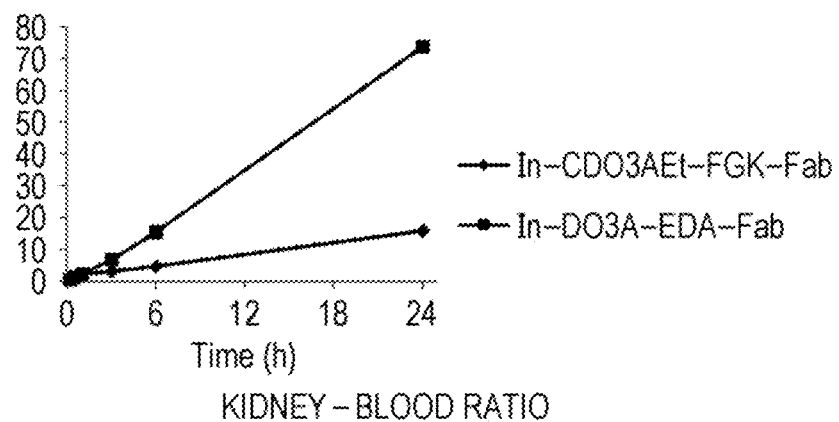

FIGS. 6A to 6C show comparisons between the results of $^{111}$In-CDO3AEt-FGK-Fab and $^{111}$In-DO3A-EDA-Fab.

From the results of the $^{111}$In-CDO3AEt-FGK-Fab that is a compound of the present invention and the $^{111}$In-DO3A-EDA-Fab that is a comparative compound, it can be understood that the 11 In-CDO3AEt-FGK-Fab suppresses the accumulation thereof in the kidney, and has a low kidney-blood ratio, while showing a blood concentration similar to that of the $^{111}$In-DO3A-EDA-Fab.

The above-described experimental results show that $^{111}$In-CDO3AEt-FGK-Fab (derived from Rabbit serum IgG), $^{111}$In-CDO3AEt-FGK-Fab (derived from anti-c-kit IgG), $^{111}$In-CDOTA-Bn-CO-FGK-Fab (derived from anti-c-kit IgG), and $^{111}$In-DO3A-Bn-CO-FGK-Fab (derived from Rabbit serum IgG), which are compounds of the invention of the present application and have a benzylamide structure as a linking group remarkably suppress the radioactivity in the kidney, but in contrast, $^{111}$In-DO3A-Bn-SCN- MVK-Fab having a thiourea structure as a linking group and $^{111}$In-DO3A-EDA-Fab (derived from Rabbit serum IgG) having an ethylene structure as a linking group, which are comparative compounds, exhibit high values of radioactivity in the kidney. From the above-described results and the test results of incubation test with BBMVs, it is considered that the compound of the invention of the present application having a benzylamide structure is metabolized by an enzyme, and radioactive metal sites are released from the compound before being taken into the kidney, and on the other hand, it is considered that the comparative compound having a thiourea structure is not recognized by any enzyme, but results in no release of metabolites.

Figure 7A:
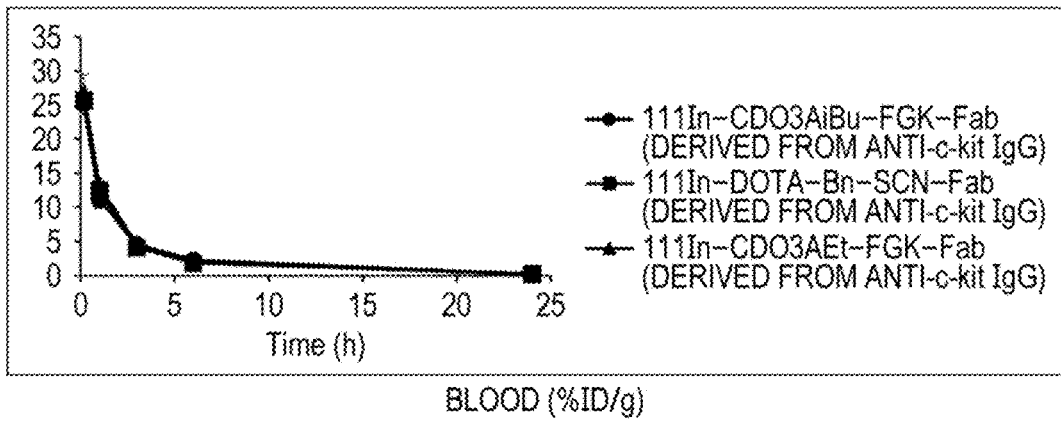
FIGS. 7A-7C show comparisons among the results of $^{111}$In-CDO3AiBu-FGK-Fab (derived from anti-c-kit IgG), $^{111}$In-DOTA-Bn-SCN-Fab (derived from anti-c-kit IgG), and $^{111}$In-CDO3AEt-FGK-Fab (derived from anti-c-kit IgG).
Figure 7B:
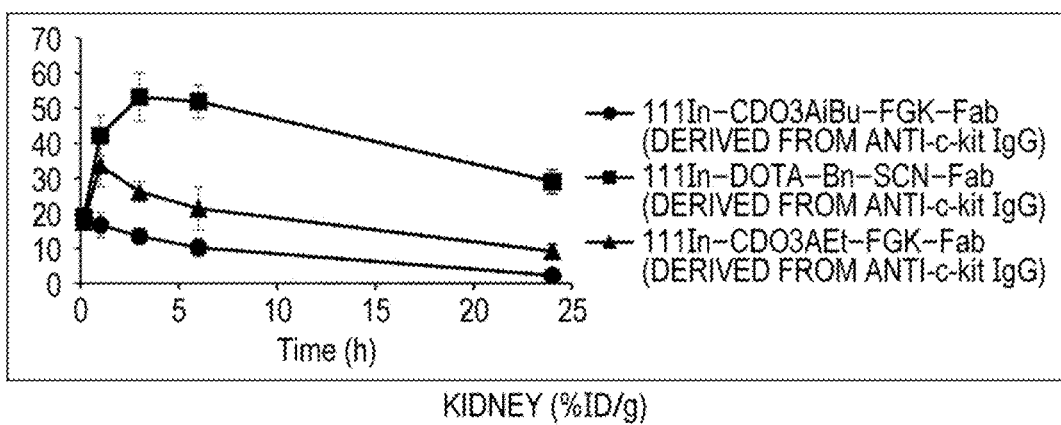
Figure 7C:
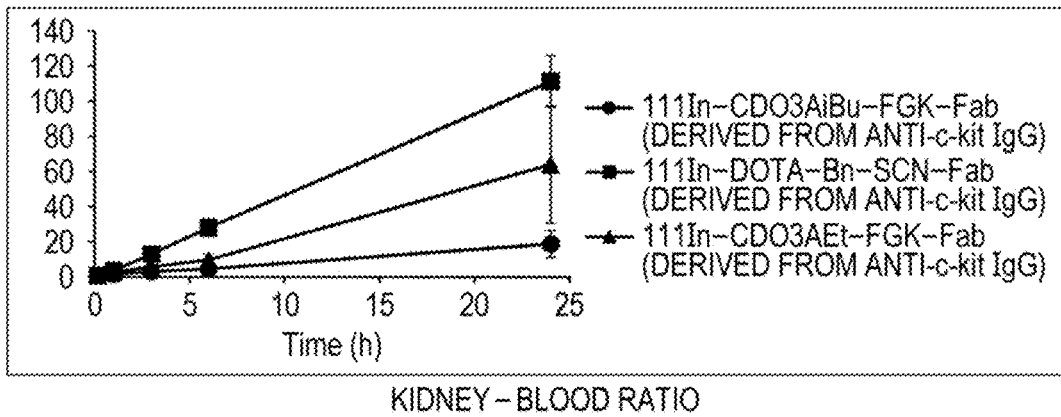

FIGS. 7A to 7C show comparisons among the results of the $^{111}$In-CDO3AiBu-FGK-Fab (derived from anti-c-kit IgG), the $^{111}$In-DOTA-Bn-SCN-Fab (derived from anti-c-kit IgG), and the $^{111}$In-CDO3AEt-FGK-Fab (derived from anti-c-kit IgG).

From these results, it can be understood that the $^{111}$In-CDO3AiBu-FGK-Fab further suppresses the accumulation thereof in the kidney as compared with the accumulation of the $^{111}$In-CDO3AEt-FGK-Fab, and has a lower kidney-blood ratio.

TABLE 3

$^{111}$In-CDO3AEt-FGK-Fab (derived from Rabbit serum IgG)

|  | 10 min | 30 min | 1 h | 3 h | 6 h | 24 h |
|---|---|---|---|---|---|---|
| Blood | 20.97 ± 2.89 | 15.27 ± 0.22 | 8.21 ± 2.67 | 4.84 ± 0.39 | 2.67 ± 0.46 | 0.47 ± 0.08 |
| Liver | 5.75 ± 0.45 | 4.56 ± 0.26 | 4.36 ± 0.21 | 3.31 ± 0.28 | 3.44 ± 0.43 | 1.85 ± 0.14 |
| Spleen | 3.90 ± 0.62 | 3.12 ± 0.09 | 2.64 ± 0.59 | 1.30 ± 0.73 | 1.63 ± 0.19 | 0.76 ± 0.16 |
| Kidney | 11.87 ± 0.79 | 16.93 ± 3.34 | 18.74 ± 3.75 | 15.13 ± 5.01 | 12.55 ± 1.03 | 7.53 ± 2.02 |
| Pancreas | 1.26 ± 0.15 | 1.37 ± 0.10 | 1.82 ± 0.67 | 1.38 ± 0.02 | 1.23 ± 0.22 | 0.49 ± 0.06 |
| Heart | 4.76 ± 0.76 | 4.68 ± 0.14 | 3.75 ± 0.16 | 1.72 ± 0.21 | 1.22 ± 0.22 | 0.49 ± 0.08 |
| Lung | 8.86 ± 1.66 | 9.94 ± 2.43 | 9.21 ± 2.01 | 4.17 ± 0.31 | 2.21 ± 0.45 | 0.57 ± 0.02 |
| Stomach* | 0.55 ± 0.04 | 0.61 ± 0.06 | 0.89 ± 0.16 | 0.87 ± 0.26 | 0.65 ± 0.26 | 0.21 ± 0.04 |
| Intestine* | 2.97 ± 0.21 | 3.50 ± 0.08 | 4.04 ± 0.50 | 4.28 ± 1.51 | 3.56 ± 2.78 | 0.91 ± 0.15 |
| Muscle | 0.79 ± 0.23 | 0.92 ± 0.20 | 0.99 ± 0.40 | 0.83 ± 0.16 | 0.53 ± 0.15 | 0.19 ± 0.05 |
| Bone | 2.47 ± 0.14 | 2.61 ± 0.17 | 2.58 ± 0.37 | 1.60 ± 0.07 | 0.96 ± 0.15 | 0.47 ± 0.08 |
| Urine* |  |  |  |  | 45.68 ± 5.70 | 64.09 ± 3.60 |
| Feces* |  |  |  |  | 0.74 ± 0.52 | 8.88 ± 3.91 |

The unit is "% ID/g", provided that the unit with the symbol * is "% ID".

TABLE 4

$^{111}$In-CDO3AEt-FGK-Fab (derived from anti-c-kit IgG)

|  | 10 min | 1 h | 3 h | 6 h | 24 h |
|---|---|---|---|---|---|
| Blood | 26.96 ± 1.22 | 12.96 ± 1.36 | 4.66 ± 0.34 | 2.15 ± 0.29 | 0.14 ± 0.02 |
| Liver | 5.21 ± 0.44 | 4.95 ± 1.02 | 3.38 ± 0.38 | 2.65 ± 0.21 | 1.66 ± 0.28 |
| Spleen | 4.48 ± 0.75 | 4.42 ± 0.90 | 3.62 ± 1.54 | 1.53 ± 0.21 | 0.70 ± 0.08 |
| Kidney | 16.23 ± 1.69 | 23.73 ± 5.30 | 24.21 ± 4.25 | 18.52 ± 5.34 | 7.92 ± 3.22 |
| Pancreas | 1.01 ± 0.02 | 1.50 ± 0.28 | 1.35 ± 0.35 | 1.72 ± 0.19 | 0.88 ± 0.07 |
| Heart | 5.27 ± 0.20 | 4.71 ± 0.55 | 2.87 ± 0.18 | 2.39 ± 0.15 | 1.17 ± 0.17 |
| Lung | 13.50 ± 2.22 | 8.26 ± 1.29 | 3.67 ± 0.70 | 1.77 ± 0.24 | 0.42 ± 0.05 |
| Stomach* | 0.70 ± 0.30 | 0.71 ± 0.14 | 0.59 ± 0.06 | 0.57 ± 0.06 | 0.26 ± 0.11 |
| Intestine* | 2.39 ± 0.21 | 4.51 ± 0.72 | 4.15 ± 0.63 | 5.27 ± 0.51 | 2.11 ± 0.72 |
| Muscle | 0.70 ± 0.15 | 1.01 ± 0.19 | 0.95 ± 0.19 | 0.83 ± 0.21 | 0.46 ± 0.11 |
| Bone | 2.55 ± 0.62 | 2.76 ± 0.41 | 1.65 ± 0.54 | 0.96 ± 0.36 | 0.46 ± 0.11 |

The unit is "% ID/g", provided that the unit with the symbol * is "% ID".

TABLE 5

$^{111}$In-DO3A-EDA-Fab (derived from Rabbit serum IgG)

|  | 10 min | 30 min | 1 h | 3 h | 6 h | 24 h |
|---|---|---|---|---|---|---|
| Blood | 25.50 ± 0.79 | 15.88 ± 0.15 | 10.93 ± 0.74 | 5.30 ± 0.81 | 2.83 ± 0.19 | 0.47 ± 0.03 |
| Liver | 4.24 ± 0.30 | 3.43 ± 0.28 | 3.25 ± 0.21 | 3.66 ± 1.00 | 3.04 ± 0.39 | 3.62 ± 0.56 |
| Spleen | 3.06 ± 0.11 | 2.26 ± 0.07 | 1.96 ± 0.15 | 1.73 ± 0.32 | 1.85 ± 0.21 | 1.98 ± 0.25 |
| Kidney | 13.92 ± 0.79 | 20.45 ± 0.86 | 25.93 ± 1.82 | 35.49 ± 3.05 | 43.59 ± 4.03 | 34.45 ± 3.76 |
| Pancreas | 1.03 ± 0.21 | 1.08 ± 0.21 | 1.05 ± 0.07 | 1.06 ± 0.20 | 1.05 ± 0.05 | 0.62 ± 0.02 |
| Heart | 4.65 ± 0.20 | 3.83 ± 0.15 | 3.18 ± 0.40 | 1.94 ± 0.28 | 1.50 ± 0.07 | 0.87 ± 0.15 |
| Lung | 10.84 ± 1.78 | 6.46 ± 1.32 | 4.64 ± 0.96 | 2.73 ± 0.71 | 1.81 ± 0.27 | 0.69 ± 0.03 |
| Stomach* | 0.40 ± 0.01 | 0.51 ± 0.11 | 0.51 ± 0.03 | 0.52 ± 0.12 | 0.33 ± 0.09 | 0.24 ± 0.02 |
| Intestine* | 2.59 ± 0.47 | 2.98 ± 0.37 | 3.00 ± 0.37 | 2.69 ± 0.27 | 2.49 ± 0.44 | 1.57 ± 0.08 |
| Muscle | 1.04 ± 0.20 | 1.32 ± 0.10 | 1.35 ± 0.20 | 1.05 ± 0.16 | 0.92 ± 0.01 | 0.56 ± 0.18 |
| Bone | 2.24 ± 0.77 | 1.73 ± 0.18 | 1.58 ± 0.31 | 1.07 ± 0.15 | 0.77 ± 0.03 | 0.44 ± 0.18 |
| Urine* |  |  |  |  | 33.04 ± 4.57 | 49.59 ± 0.80 |
| Feces* |  |  |  |  | 0.05 ± 0.02 | 2.15 ± 1.02 |

The unit is "% ID/g", provided that the unit with the symbol * is "% ID".

TABLE 6

| ¹¹¹In-CDOTA-Bn-CO-FGK-Fab (derived from anti-c-kit IgG) | | | | | |
|---|---|---|---|---|---|
| | 10 min | 1 h | 3 h | 6 h | 24 h |
| Blood | 27.09 ± 2.25 | 13.36 ± 1.78 | 5.75 ± 0.85 | 2.75 ± 0.50 | 0.22 ± 0.05 |
| Liver | 6.22 ± 0.23 | 6.09 ± 0.90 | 7.06 ± 1.43 | 6.44 ± 1.23 | 5.04 ± 1.01 |
| Spleen | 4.53 ± 0.50 | 5.03 ± 0.98 | 4.56 ± 1.35 | 3.37 ± 0.47 | 2.62 ± 0.51 |
| Kidney | 13.09 ± 1.89 | 20.69 ± 2.86 | 23.19 ± 2.08 | 25.41 ± 2.83 | 13.31 ± 3.73 |
| Pancreas | 0.88 ± 0.13 | 1.17 ± 0.15 | 1.68 ± 0.20 | 1.58 ± 0.19 | 1.23 ± 0.20 |
| Heart | 4.32 ± 0.50 | 4.17 ± 0.90 | 3.25 ± 0.59 | 2.46 ± 0.16 | 1.69 ± 0.25 |
| Lung | 8.96 ± 1.34 | 4.87 ± 0.83 | 3.16 ± 0.42 | 1.85 ± 0.16 | 0.75 ± 0.06 |
| Stomach* | 0.35 ± 0.04 | 0.54 ± 0.08 | 0.65 ± 0.08 | 0.55 ± 0.07 | 0.72 ± 0.18 |
| Intestine* | 2.16 ± 0.34 | 3.18 ± 0.69 | 7.75 ± 1.09 | 9.26 ± 0.77 | 5.98 ± 4.94 |
| Muscle | 0.82 ± 0.29 | 1.11 ± 0.17 | 0.99 ± 0.17 | 0.72 ± 0.12 | 0.47 ± 0.06 |
| Bone | 2.97 ± 0.74 | 2.62 ± 0.64 | 3.21 ± 0.72 | 2.49 ± 1.13 | 2.43 ± 1.15 |

The unit is "% ID/g", provided that the unit with the symbol * is "% ID".

TABLE 7

| ¹¹¹IN-DO3A-Bn-SCN-MVK-Fab (derived from Rabbot serum IgG) | | | | | |
|---|---|---|---|---|---|
| | 10 min | 30 min | 1 h | 3 h | 6 h |
| Blood | 23.99 ± 0.87 | 15.39 ± 0.87 | 9.43 ± 0.42 | 3.94 ± 0.28 | 1.93 ± 0.23 |
| Liver | 4.03 ± 0.09 | 3.02 ± 0.29 | 2.64 ± 0.10 | 2.13 ± 0.03 | 1.79 ± 0.15 |
| Spleen | 2.88 ± 0.15 | 2.05 ± 0.05 | 1.48 ± 0.12 | 0.95 ± 0.06 | 0.68 ± 0.03 |
| Kidney | 20.68 ± 3.07 | 30.16 ± 1.77 | 33.71 ± 2.35 | 37.78 ± 5.90 | 23.32 ± 4.55 |
| Pancreas | 1.04 ± 0.22 | 1.13 ± 0.01 | 1.11 ± 0.17 | 0.96 ± 0.09 | 0.79 ± 0.12 |
| Heart | 4.42 ± 0.32 | 3.98 ± 0.15 | 2.89 ± 0.26 | 1.45 ± 0.14 | 1.07 ± 0.12 |
| Lung | 8.60 ± 0.44 | 6.62 ± 1.41 | 5.47 ± 2.14 | 2.23 ± 0.30 | 1.34 ± 0.20 |
| Stomach* | 0.38 ± 0.06 | 0.53 ± 0.06 | 0.43 ± 0.05 | 0.43 ± 0.06 | 0.27 ± 0.07 |
| Intestine* | 2.33 ± 0.31 | 3.51 ± 0.09 | 3.20 ± 0.07 | 3.40 ± 0.54 | 2.73 ± 0.17 |
| Muscle | 0.84 ± 0.06 | 1.22 ± 0.12 | 1.13 ± 0.02 | 0.86 ± 0.09 | 0.54 ± 0.06 |
| Bone | 2.25 ± 0.14 | 2.24 ± 0.23 | 1.64 ± 0.21 | 0.77 ± 0.05 | 0.53 ± 0.11 |
| Urine* | | | | | 46.02 ± 2.04 |
| Feces* | | | | | 0.13 ± 0.13 |

The unit is "% ID/g", provided that the unit with the symbol * is "% ID".

TABLE 8

| ¹¹¹In-DO3A-Bn-CO-FGK-Fab (derived from Rabbit serum IgG) | | | | | |
|---|---|---|---|---|---|
| | 10 min | 30 min | 1 h | 3 h | 6 h |
| Blood | 25.57 ± 2.36 | 15.35 ± 1.62 | 9.69 ± 0.87 | 4.23 ± 0.29 | 2.31 ± 0.07 |
| Liver | 4.08 ± 0.31 | 2.87 ± 0.20 | 2.41 ± 0.27 | 1.63 ± 0.11 | 1.45 ± 0.14 |
| Spleen | 2.76 ± 0.32 | 1.80 ± 0.32 | 1.25 ± 0.086 | 0.82 ± 0.06 | 0.57 ± 0.04 |
| Kidney | 14.59 ± 2.27 | 21.65 ± 2.41 | 26.99 ± 3.09 | 22.77 ± 2.74 | 15.64 ± 6.81 |
| Pancreas | 0.88 ± 0.05 | 0.99 ± 0.08 | 1.15 ± 0.12 | 0.93 ± 0.05 | 0.95 ± 0.12 |
| Heart | 4.98 ± 0.96 | 4.53 ± 0.76 | 3.50 ± 0.33 | 1.73 ± 0.06 | 1.23 ± 0.18 |
| Lung | 9.05 ± 1.74 | 6.07 ± 1.03 | 4.46 ± 1.00 | 2.18 ± 0.38 | 1.51 ± 0.07 |
| Stomach* | 0.40 ± 0.03 | 0.51 ± 0.10 | 0.52 ± 0.05 | 0.43 ± 0.73 | 0.30 ± 0.04 |
| Intestine* | 2.28 ± 0.18 | 3.25 ± 0.18 | 3.58 ± 0.14 | 3.72 ± 0.42 | 3.88 ± 0.73 |
| Muscle | 0.88 ± 0.10 | 1.17 ± 0.19 | 1.34 ± 0.08 | 0.88 ± 0.04 | 0.71 ± 0.12 |
| Bone | 2.68 ± 0.47 | 1.78 ± 0.24 | 1.48 ± 0.20 | 0.87 ± 0.06 | 0.71 ± 0.08 |
| Urine* | | | | | 45.98 ± 6.55 |
| Feces* | | | | | 0.01 ± 0.02 |

The unit is "% ID/g", provided that the unit with the symbol * is "% ID".

TABLE 9

| ¹¹¹In-CDO3AiBu-FGK-Fab (derived from Rabbit serum IgG) | | | | | |
|---|---|---|---|---|---|
| | 10 min | 1 h | 3 h | 6 h | 24 h |
| Blood | 22.97 ± 1.16 | 11.27 ± 0.73 | 5.41 ± 0.36 | 2.80 ± 0.11 | 0.31 ± 0.03 |
| Liver | 4.58 ± 0.28 | 2.74 ± 0.21 | 2.32 ± 0.33 | 1.70 ± 0.28 | 0.71 ± 0.10 |
| Spleen | 3.08 ± 0.23 | 1.98 ± 0.23 | 1.17 ± 0.09 | 0.60 ± 0.36 | 0.26 ± 0.04 |
| Kidney | 15.18 ± 1.49 | 12.74 ± 1.49 | 8.94 ± 2.01 | 8.76 ± 2.00 | 1.61 ± 0.48 |
| Pancreas | 1.01 ± 0.26 | 1.09 ± 0.26 | 1.26 ± 0.09 | 1.03 ± 0.08 | 0.35 ± 0.14 |
| Heart | 3.97 ± 0.29 | 3.44 ± 0.29 | 1.64 ± 0.05 | 1.17 ± 0.06 | 0.24 ± 0.04 |
| Lung | 7.44 ± 0.19 | 4.66 ± 0.19 | 2.69 ± 0.24 | 1.82 ± 0.18 | 0.33 ± 0.10 |
| Stomach* | 0.37 ± 0.07 | 0.59 ± 0.07 | 0.57 ± 0.09 | 0.44 ± 0.17 | 0.43 ± 0.33 |

TABLE 9-continued

¹¹¹In-CDO3AiBu-FGK-Fab (derived from Rabbit serum IgG)

|  | 10 min | 1 h | 3 h | 6 h | 24 h |
|---|---|---|---|---|---|
| Intestine* | 2.49 ± 0.34 | 5.48 ± 0.34 | 7.13 ± 0.15 | 6.96 ± 2.87 | 3.40 ± 1.65 |
| Muscle | 0.60 ± 0.11 | 0.98 ± 0.11 | 0.78 ± 0.16 | 0.46 ± 0.08 | 0.09 ± 0.05 |
| Bone | 2.60 ± 0.24 | 1.42 ± 0.24 | 0.87 ± 0.24 | 0.59 ± 0.12 | 0.11 ± 0.13 |
| Urine* |  |  |  | 55.55 ± 3.54 | 71.38 ± 6.89 |
| Feces* |  |  |  | 0.90 ± 0.71 | 8.52 ± 3.53 |

The unit is "% ID/g", provided that the unit with the symbol * is "% ID".

TABLE 10

¹¹¹In-CDO3AiBu-FGK-Fab (derived from anti-c-kit IgG)

|  | 10 min | 1 h | 3 h | 6 h | 24 h |
|---|---|---|---|---|---|
| Blood | 25.29 ± 1.56 | 11.11 ± 1.29 | 4.55 ± 0.21 | 2.23 ± 0.36 | 0.13 ± 0.04 |
| Liver | 4.72 ± 0.40 | 3.30 ± 0.35 | 2.24 ± 0.12 | 1.87 ± 0.36 | 0.61 ± 0.06 |
| Spleen | 3.79 ± 0.42 | 2.47 ± 0.12 | 1.41 ± 0.18 | 0.89 ± 0.17 | 0.25 ± 0.08 |
| Kidney | 18.34 ± 1.70 | 16.70 ± 3.59 | 12.55 ± 2.15 | 10.21 ± 2.60 | 2.30 ± 0.57 |
| Pancreas | 1.05 ± 0.11 | 1.17 ± 0.12 | 1.40 ± 0.10 | 1.42 ± 0.18 | 0.44 ± 0.14 |
| Heart | 4.83 ± 0.32 | 3.65 ± 0.43 | 2.16 ± 0.23 | 1.26 ± 0.12 | 0.27 ± 0.05 |
| Lung | 9.07 ± 2.88 | 5.08 ± 0.99 | 2.56 ± 0.17 | 1.57 ± 0.27 | 0.23 ± 0.08 |
| Stomach* | 0.38 ± 0.03 | 0.57 ± 0.12 | 0.60 ± 0.14 | 0.45 ± 0.10 | 0.34 ± 0.22 |
| Intestine* | 2.33 ± 0.20 | 4.30 ± 0.17 | 7.05 ± 0.66 | 12.75 ± 3.07 | 2.16 ± 0.56 |
| Muscle | 0.76 ± 0.13 | 1.08 ± 0.16 | 0.78 ± 0.20 | 0.44 ± 0.07 | 0.10 ± 0.03 |
| Bone | 2.46 ± 0.81 | 2.08 ± 1.32 | 0.90 ± 0.13 | 0.72 ± 0.14 | 0.24 ± 0.05 |
| Urine* |  |  |  | 45.52 ± 5.64 | 69.43 ± 2.50 |
| Feces* |  |  |  | 0.31 ± 0.21 | 14.34 ± 1.25 |

The unit is "% ID/g", provided that the unit with the symbol * is "% ID".

TABLE 11

¹¹¹In-DOTA-Bn-SCN-Fab (derived from anti-c-kit IgG)

|  | 10 min | 1 h | 3 h | 6 h | 24 h |
|---|---|---|---|---|---|
| Blood | 25.65 ± 0.95 | 12.45 ± 0.99 | 4.14 ± 0.44 | 1.88 ± 0.20 | 0.26 ± 0.05 |
| Liver | 4.20 ± 0.35 | 3.80 ± 0.47 | 3.32 ± 0.59 | 3.45 ± 0.33 | 3.35 ± 0.77 |
| Spleen | 4.16 ± 0.57 | 3.72 ± 0.52 | 3.95 ± 0.75 | 3.43 ± 0.53 | 3.05 ± 0.89 |
| Kidney | 18.93 ± 1.77 | 42.23 ± 5.69 | 53.17 ± 6.89 | 51.88 ± 4.68 | 29.08 ± 3.45 |
| Pancreas | 0.79 ± 0.10 | 1.11 ± 0.12 | 1.62 ± 0.13 | 1.90 ± 0.19 | 1.43 ± 0.51 |
| Heart | 5.34 ± 0.71 | 4.81 ± 0.66 | 3.29 ± 0.09 | 2.91 ± 0.33 | 2.56 ± 0.70 |
| Lung | 9.43 ± 2.58 | 5.79 ± 0.71 | 3.04 ± 0.38 | 1.95 ± 0.19 | 0.97 ± 0.16 |
| Stomach* | 0.38 ± 0.03 | 0.63 ± 0.07 | 0.60 ± 0.04 | 0.59 ± 0.07 | 0.64 ± 0.19 |
| Intestine* | 2.43 ± 0.56 | 4.75 ± 0.49 | 4.32 ± 0.23 | 4.50 ± 0.58 | 6.43 ± 5.02 |
| Muscle | 0.72 ± 0.06 | 1.15 ± 0.09 | 1.15 ± 0.15 | 1.00 ± 0.17 | 0.57 ± 0.16 |
| Bone | 2.79 ± 0.63 | 1.91 ± 0.30 | 1.79 ± 0.30 | 1.69 ± 0.16 | 1.19 ± 0.63 |
| Urine* |  |  |  | 16.36 ± 1.96 | 38.27 ± 6.80 |
| Feces* |  |  |  | 0.05 ± 0.06 | 1.76 ± 0.43 |

The unit is "% ID/g", provided that the unit with the symbol * is "% ID".

(Analysis of radioactivity in urine)

The ¹¹¹In-CDO3AEt-FGK-Fab (derived from Rabbit serum IgG) was diluted with D-PBS (−). A ¹¹¹In-CDO3AEt-FGK-Fab (derived from Rabbit serum IgG) solution (4 μCi/100 μL/mouse) adjusted to have a Fab concentration of 5 μg/100 μL was intravenously administered to a mouse via the tail vein thereof, the urine accumulated by the time after the lapse of 24 hours from the administration was filtered with a filter of 0.45 μm, and then the chemical form was analyzed by SE-HPLC. Further, into the recovered urine, EtOH in a volume twice the volume of the urine was added to precipitate proteins, and the obtained mixture was centrifuged at 15,000 g for 5 minutes, and then the supernatant was recovered. After the supernatant was recovered, the pellets were washed with 100 μL of 66% EtOH solution, the obtained mixture was again centrifuged to recover the supernatant twice, and the recovery rate of the radioactivity into the supernatant was calculated. After that, the supernatant was diluted with D-PBS(−) so as to have an EtOH concentration of 15% or less, and the diluted supernatant was analyzed by RP-HPLC.

Figure 8A:
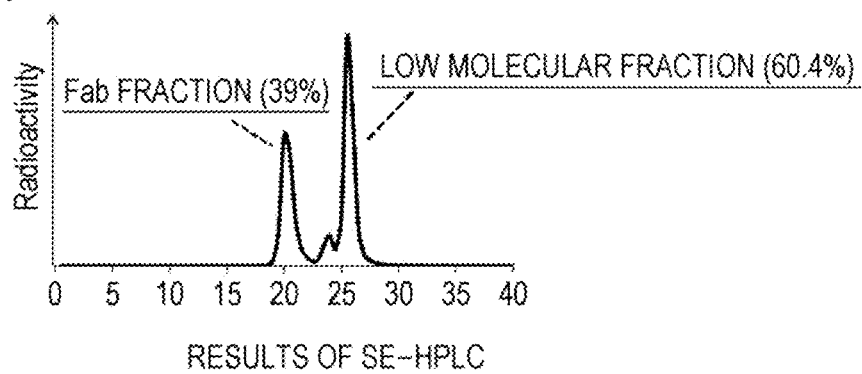
FIGS. 8A-8B show results of analysis for chemical form with the radioactivity in the urine excreted by the time after the lapse of 24 hours from the administration of $^{111}$In-CDO3AEt-FGK-Fab (derived from Rabbit serum IgG) to a mouse.
Figure 8B:
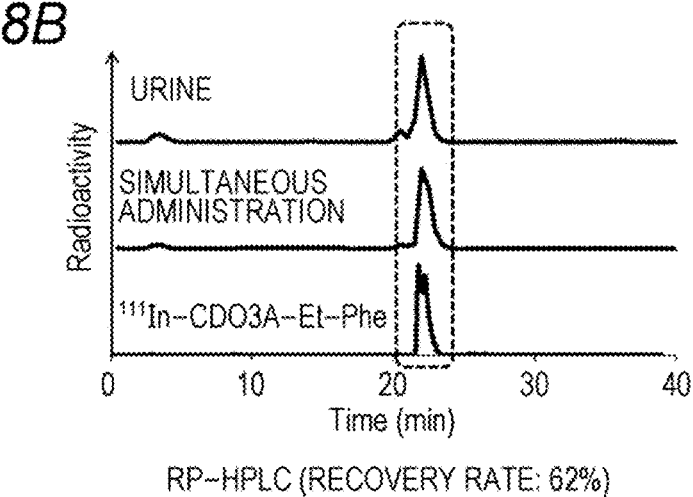

FIGS. 8A-8B show analysis results of chemical forms of the radioactivity in the urine excreted by the time after the lapse of 24 hours from the administration of ¹¹¹In-CDO3AEt-FGK-Fab (derived from Rabbit serum IgG) to a mouse. As described in the above, in the analysis by SE-HPLC shown in FIG. 8A by the analysis of the radioactivity in urine, most of the radioactivity is excreted in a low molecular fraction, and from the results of RP-HPLC shown in FIG. 8B, it can be understood that, in case of the ¹¹¹In-CDO3AEt-FGK-Fab, the major radioactivity in the low molecular fraction is from ¹¹¹In-CDO3AEt-Phe (a compound resulting from cleavage of the ¹¹¹In-CDO3AEt-FGK-Fab between the phenylalanine and the glycine).

In a similar manner to the above except that the $^{111}$In-CDO3AEt-FGK-Fab (derived from Rabbit serum IgG) was changed to $^{111}$In-CDOTA-Bn-CO-FGK-Fab (derived from anti-c-kit IgG) and the urine excreted by the time after the lapse of 6 hours from the administration was accumulated and analyzed, the radioactivity in urine was analyzed.

Figure 9:
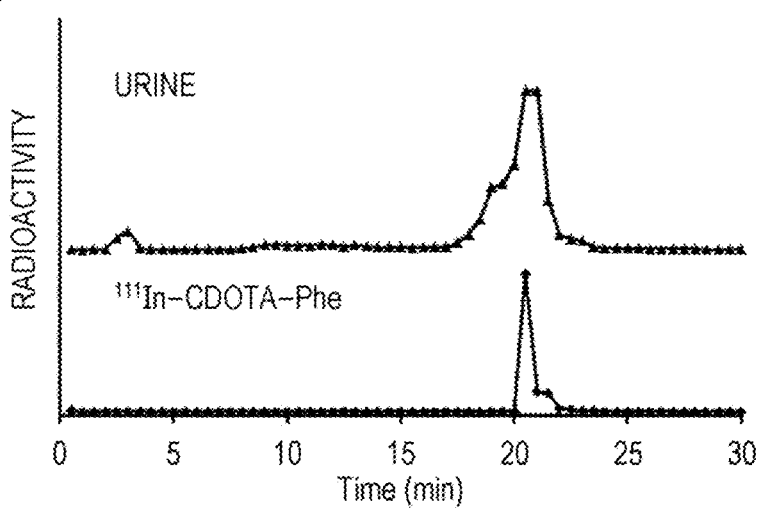
FIG. 9 shows results of analysis for chemical form with the radioactivity in the urine excreted by the time after the lapse of 6 hours from the administration of $^{111}$In-CDOTA-Bn-CO-FGK-Fab (derived from anti-c-kit IgG) to a mouse.

FIG. 9 shows analysis results of chemical forms of the radioactivity in the urine excreted by the time after the lapse of 6 hours from the administration of $^{111}$In-CDOTA-Bn-CO-FGK-Fab (derived from anti-c-kit IgG) to a mouse. From the results of RP-HPLC, it can be understood that, in the case of $^{111}$In-CDOTA-Bn-CO-FGK-Fab, the major radioactivity in the low molecular fraction is from $^{111}$In-CDOTA-Phe (a compound resulting from cleavage of the $^{111}$In-CDOTA-Bn-CO-FGK-Fab between the phenylalanine and the glycine).

In a similar manner to the above except that the $^{111}$In-CDO3AEt-FGK-Fab (derived from Rabbit serum IgG) was changed to $^{111}$In-DO3A-Bn-CO-FGK-Fab (derived from Rabbit serum IgG), the radioactivity in urine was analyzed.

Figure 10:
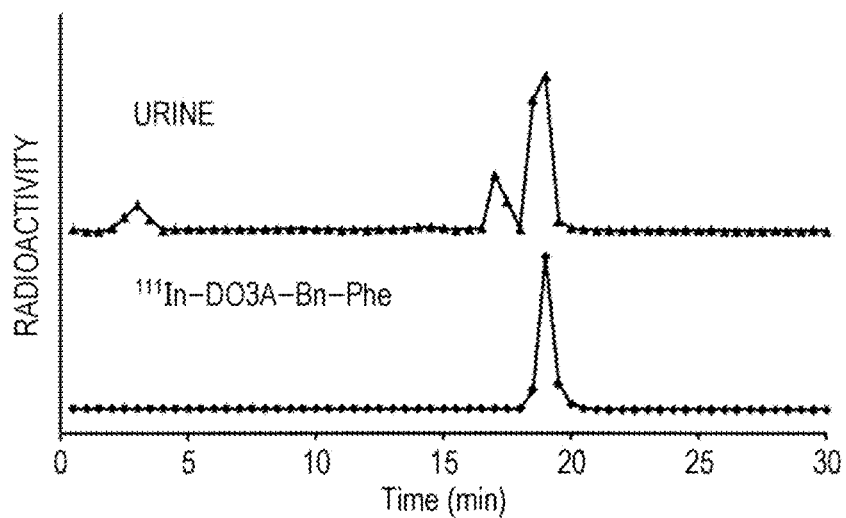
FIG. 10 shows results of analysis for chemical form with the radioactivity in the urine excreted by the time after the lapse of 24 hours from the administration of $^{111}$In-CDO3AEt-FGK-Fab (derived from Rabbit serum IgG) to a mouse.

FIG. 10 shows analysis results of chemical forms of the radioactivity in the urine excreted by the time after the lapse of 24 hours from the administration of $^{111}$In-DO3A-Bn-CO-FGK-Fab (derived from Rabbit serum IgG) to a mouse. From the results of RP-HPLC, it can be understood that, in case of the $^{111}$In-DO3A-Bn-CO-FGK-Fab, the major radioactivity in the low molecular fraction is from $^{111}$In-DO3A-Phe (a compound resulting from cleavage of the $^{111}$In-DO3A-Bn-CO-FGK-Fab between the phenylalanine and the glycine).

In a similar manner to the above except that the $^{111}$In-CDO3AEt-FGK-Fab (derived from Rabbit serum IgG) was changed to $^{111}$In-CDO3AiBu-FGK-Fab (derived from Rabbit serum IgG), the radioactivity in urine was analyzed.

Figure 11A:
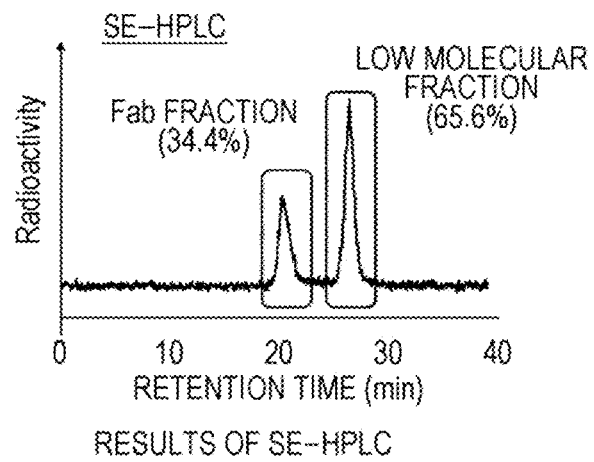
FIGS. 11A-11B show results of analysis for chemical form with the radioactivity in the urine excreted by the time after the lapse of 24 hours from the administration of $^{111}$In-CDO3AiBu-FGK-Fab (derived from Rabbit serum IgG) to a mouse.
Figure 11B:
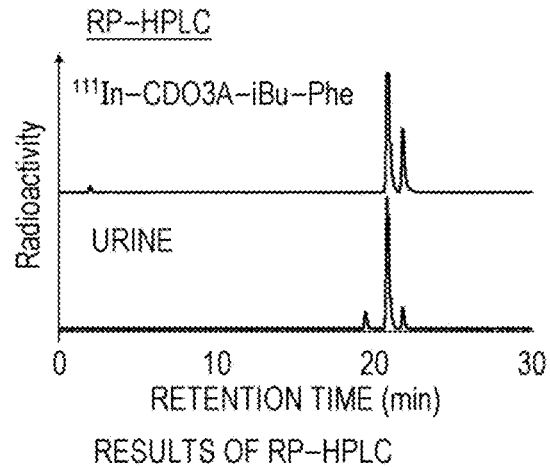

FIGS. 11A-11B show analysis results of chemical forms of the radioactivity in the urine excreted by the time after the lapse of 24 hours from the administration of $^{111}$In-CDO3AiBu-FGK-Fab (derived from Rabbit serum IgG) to a mouse. As described in the above, in the analysis by SE-HPLC shown in FIG. 11A by the analysis of the radioactivity in urine, most of the radioactivity is excreted as a low molecular fraction, and from the results of RP-HPLC shown in FIG. 11B, it can be understood that in case of the $^{111}$In-CDO3AiBu-FGK-Fab (derived from Rabbit serum IgG), the major radioactivity in the low molecular fraction is from $^{111}$In-CDO3AiBu-Phe (a compound resulting from cleavage of the $^{111}$In-CDO3AiBu-FGK-Fab between the phenylalanine and the glycine).

(SPECT/CT Imaging)

The $^{111}$In-CDO3AEt-FGK-Fab (derived from anti-c-kit IgG) prepared by the above-described method was diluted with D-PBS(−). A $^{111}$In-CDO3AEt-FGK-Fab solution (45 μCi/100 μL/mouse) adjusted to have a Fab concentration of 25 μg/100 μL was intravenously administered to each of the above-described SY subcutaneous tumor model mice via the tail vein thereof. Two mice in each group were imaged from the time after the lapse of 2.5 hours from the administration by using a SPECT/CT device (SPECT4CT, available from Trifoil Imaging, CA), under the conditions of 360-degree collection of a 5-pinhole collimator with an opening diameter of 1 mm, 16 projections, and 14 minutes/projection.

In a similar manner to the above except that the $^{111}$In-CDO3AEt-FGK-Fab (derived from anti-c-kit IgG) solution (45 μCi/100 μL/mouse) was changed to a $^{111}$In-DO3A-Bn-SCN-MVK-Fab (derived from anti-c-kit IgG) solution (14 μCi/100 μL/mouse), the $^{111}$In-DO3A-Bn-SCN-MVK-Fab was administered to each of SY subcutaneous tumor model mice via the tail vein thereof, and the images were taken from the time after the lapse of 2.5 hours from the administration.

Figure 12:
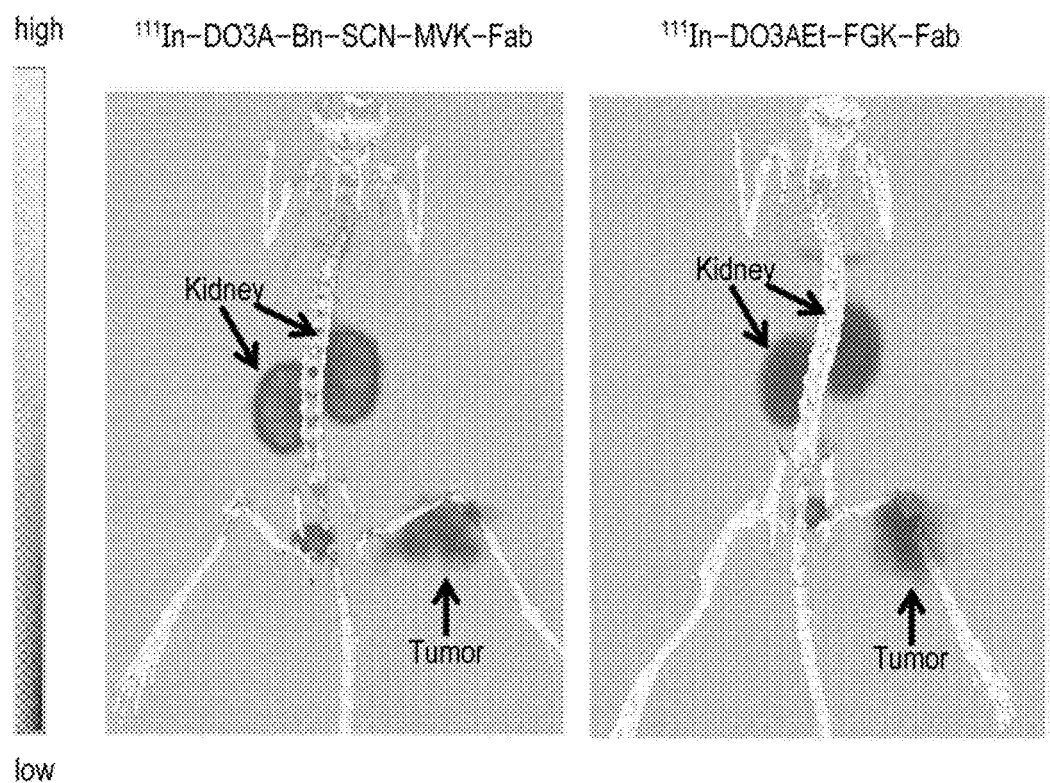
FIG. 12 shows single-photon emission computed tomography/computed tomography (SPECT/CT) images after the lapse of 2.5 hours from the administration of a $^{111}$In-DO3A-Bn-SCN-MVK-Fab (derived from anti-c-kit IgG) solution and a $^{111}$In-CDO3AEt-FGK-Fab (derived from anti-c-kit IgG) solution to SY subcutaneous tumor model mice, respectively.

FIG. 12 shows SPECT/CT images after the lapse of 2.5 hours from the administration of the $^{111}$In-DO3A-Bn-SCN-MVK-Fab (derived from anti-c-kit IgG) solution or the $^{111}$In-CDO3AEt-FGK-Fab (derived from anti-c-kit IgG) solution to each of the SY subcutaneous tumor model mice.

After the lapse of 2.5 hours from the administration, the $^{111}$In-CDO3AEt-FGK-Fab showed low accumulation in the kidney, and clearly imaged the tumor. On the other hand, the $^{111}$In-DO3A-Bn-SCN-MVK-Fab imaged the tumor, however, showed the high radioactivity in the kidney.

As described in the above, the radiolabeled drug achieves low accumulation in the kidney, and can enhance the sensitivity and accuracy of radiological imaging diagnosis.

The invention claimed is:

1. A compound of formula (1), or a pharmacologically acceptable salt thereof:

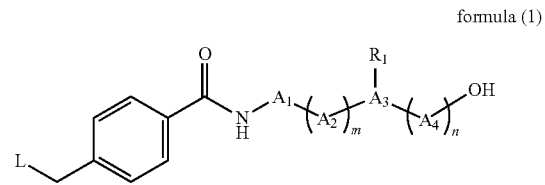

formula (1)

wherein
$A_1$ is a residue of phenylalanine, methionine, valine, leucine, isoleucine, proline, tyrosine, glycine, alanine, of tryptophan,
$A_2$ is a residue of glycine, phenylalanine, methionine, valine, leucine, isoleucine, proline, tyrosine, alanine, or tryptophan,
m is an integer of 0 to 3,
$A_3$ is an amino acid residue having an amino group or a carboxy group on a side chain thereof,
$A_4$ is an amino acid residue,
n is an integer of 0 to 3,
$R_1$ is a group binding to the amino group or the carboxy group on the side chain of $A_3$ and having a functional group capable of binding to a target molecule recognition element or a linking group thereof, the functional group is at least one selected from the group consisting of a carboxy group or an active ester thereof, a group having a C=C bond, a carbamoyl group, an isothiocyanate group and an amino group, or a hydrogen atom of the amino group or the carboxy group on the side chain of $A_3$, provided that $R_1$ optionally forms a heterocyclic group having 3 to 10 carbon atoms including a nitrogen atom of the amino group on the side chain of $A_3$ as a ring-constituting atom, and
L is formula (L1):

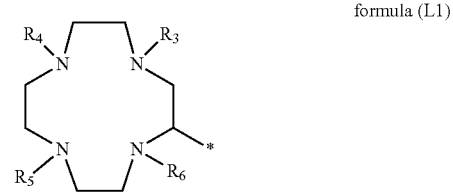

formula (L1)

wherein $R_3$, $R_4$, $R_5$, and $R_6$ each independently is a hydrogen atom, a —$CH_2COOR_{10}$ group, or a hydrocarbon group having 1 to 8 carbon atoms, $R_{10}$ is a hydrogen atom or a hydrocarbon group having 1 to 8 carbon atoms, and the symbol * represents a binding site, provided that at least three of $R_3$, $R_4$, $R_5$, and $R_6$ is a —$CH_2COOH$ group, or formula (L2):

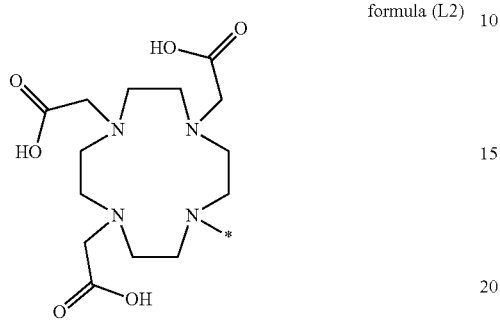

formula (L2)

wherein the symbol * represents a binding site.

2. The compound or pharmacologically acceptable salt thereof according to claim 1, wherein
an amino acid sequence of $A_1$ to $A_4$ is identical to a part of a renal brush border membrane enzyme substrate.

3. The compound or pharmacologically acceptable salt thereof according to claim 1, wherein
three of $R_3$, $R_4$, $R_5$, and $R_6$ each is a —$CH_2COOH$ group.

4. The compound or pharmacologically acceptable salt thereof according to claim 1, wherein
$A_3$ is a residue of lysine, ornithine, or arginine.

5. The compound or pharmacologically acceptable salt thereof according to claim 1, wherein
m is 1.

6. The compound or pharmacologically acceptable salt thereof according to claim 1, wherein
n is 0.

7. The compound or pharmacologically acceptable salt thereof according to claim 1, wherein
the compound is formula (1a):

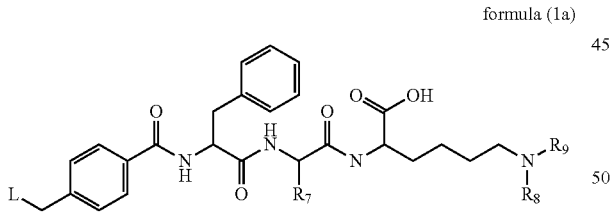

formula (1a)

wherein
is formula (L1):

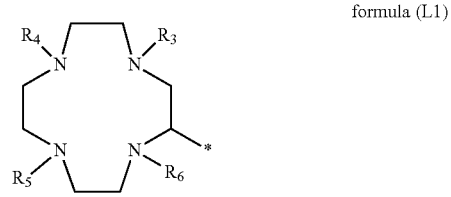

formula (L1)

wherein $R_3$, $R_4$, $R_5$, and $R_6$ each independently is a hydrogen atom, a —$CH_2COOR_{10}$ group, or a hydrocarbon group having 1 to 8 carbon atoms, $R_{10}$ is a hydrogen atom or a hydrocarbon group having 1 to 8 carbon atoms, and the symbol * represents a binding site, provided that at least three of $R_3$, $R_4$, $R_5$, and $R_6$ each is a —$CH_2COOH$ group, or formula (L2):

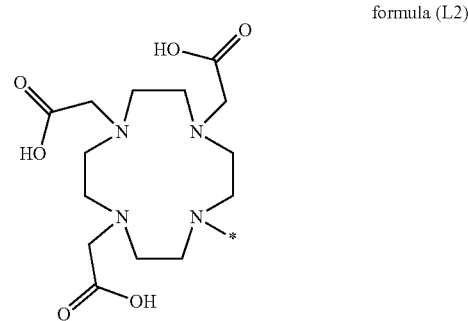 [SMILES: *N1CCN(CC(=O)O)CCN(CC(=O)O)CCN(CC(=O)O)CC1]

formula (L2)

wherein the symbol * represents a binding site,
$R_7$ is a hydrogen atom or a methyl group, and
$R_8$ and $R_9$ each independently is a hydrogen atom, or an acyl group having 2 to 20 carbon atoms in total and having a functional group, an alkyl group having 2 to 20 carbon atoms in total and having a functional group, an alkylcarbamoyl group having 2 to 20 carbon atoms in total and having a functional group, or an alkylthiocarbamoyl group having 2 to 20 carbon atoms in total and having a functional group, the functional group is at least one selected from the group consisting of a carboxy group or an active ester thereof, a group having a C=C bond, a carbamoyl group, an isothiocyanate group and an amino group,
provided that $R_8$ and $R_9$ optionally form a heterocyclic ring including the adjacent nitrogen atom, and in this case, a group

which is

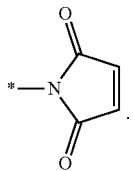 [SMILES: *N1C(=O)C=CC1=O]

8. The compound or pharmacologically acceptable salt thereof according to claim 1, wherein
L is formula (L1):

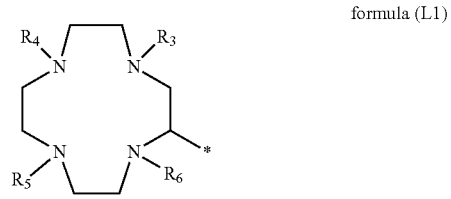

formula (L1)

wherein $R_3$, $R_4$, $R_5$, and $R_6$ each independently is a —$CH_2COOH$ group, or an isobutyl group, and the symbol * represents a binding site, provided that three of $R_3$, $R_4$, $R_5$, and $R_6$ each is a —$CH_2COOH$ group, and one of $R_3$, $R_4$, $R_5$, and $R_6$ is an isobutyl group.

9. A compound having a target molecule recognition element bound to the compound or pharmacologically acceptable salt thereof according to claim 1, or a pharmacologically acceptable salt thereof.

10. A metal complex compound comprising a metal selected from the group consisting of a radioactive metal and a radioactive atom-labeled metal; and the compound or pharmacologically acceptable salt thereof according to claim 9 coordinated to the metal, or a pharmacologically acceptable salt thereof.

11. The metal complex compound or pharmacologically acceptable salt thereof according to claim 10, wherein the metal is $^{111}$In, $^{223}$Ra, $^{67}$Ga, $^{68}$Ga, $^{44}$Sc, $^{90}$Y, $^{177}$Lu, $^{225}$Ac, $^{212}$Bi, $^{213}$Bi, $^{212}$Pb, $^{227}$Th, $^{64}$Cu, or $^{67}$Cu.

12. A drug for preparing a radioactive drug, comprising the compound or pharmacologically acceptable salt thereof according to claim 9 and one or two or more pharmaceutically acceptable carriers.

13. A radioactive drug, comprising the metal complex compound or pharmacologically acceptable salt thereof according to claim 10 and one or two or more pharmaceutically acceptable carriers.

14. A method of radiation therapy comprising administering an effective amount of a radiotherapeutic agent to a mammal, wherein the radiotherapeutic agent comprises the metal complex compound or pharmacologically acceptable salt thereof according to claim 10.

15. A method of radiological imaging comprising administering a radioactive diagnostic imaging agent to a mammal, wherein the radioactive diagnostic imaging agent comprises the metal complex compound or pharmacologically acceptable salt thereof according to claim 10.

16. A method of producing a metal complex compound or pharmacologically acceptable salt thereof comprising coordinating the compound or pharmacologically acceptable salt thereof according to claim 9 to a metal selected from the group consisting of a radioactive metal and a radioactive atom-labeled metal.

* * * * *

UNITED STATES PATENT AND TRADEMARK OFFICE
CERTIFICATE OF CORRECTION

PATENT NO. : 11,167,050 B2  
APPLICATION NO. : 16/648703  
DATED : November 9, 2021  
INVENTOR(S) : Arano et al.

Page 1 of 1

It is certified that error appears in the above-identified patent and that said Letters Patent is hereby corrected as shown below:

In the Claims

Column 82, Line 32 to Line 34:
"$A_1$ is a residue of phenylalanine, methionine, valine, leucine, isoleucine, proline, tyrosine, glycine, alanine, of tryptophan,"
Should read:
-- $A_1$ is a residue of phenylalanine, methionine, valine, leucine, isoleucine, proline, tyrosine, glycine, alanine, or tryptophan, --

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*